US006875743B1

(12) United States Patent
Lin et al.

(10) Patent No.: US 6,875,743 B1
(45) Date of Patent: Apr. 5, 2005

(54) CELL ADHESION INHIBITORS

(75) Inventors: Ko-Chung Lin, Lexington, MA (US); Steven P. Adams, Andover, MA (US); Alfredo C. Castro, Weburn, MA (US); Craig N. Zimmerman, Topsfield, MA (US); Julio Hernan Cuervo, Arlington, MA (US); Wen-Cherng Lee, Lexington, MA (US); Charles E. Hammond, Burlington, MA (US); Mary Beth Carter, Belmont, CA (US); Ronald G. Almquist, Lexington, MA (US)

(73) Assignee: Biogen, Inc., Cambridge, MA (US)

( * ) Notice: Subject to any disclaimer, the term of this patent is extended or adjusted under 35 U.S.C. 154(b) by 0 days.

(21) Appl. No.: 09/724,139

(22) Filed: Nov. 28, 2000

Related U.S. Application Data

(63) Continuation of application No. 08/983,391, filed as application No. PCT/US96/11570 on Jul. 11, 1996, now Pat. No. 6,239,108.

(51) Int. Cl.$^7$ .......................... A61K 38/00; C07K 5/00
(52) U.S. Cl. ............................ 514/15; 514/16; 514/17; 514/18; 530/326; 530/327; 530/328; 530/300; 424/185.1; 424/278.1
(58) Field of Search ........................... 514/15, 16, 17, 514/18, 2, 19; 530/326, 327, 328, 300; 424/185.1

(56) References Cited

U.S. PATENT DOCUMENTS

| | | | |
|---|---|---|---|
| 4,725,583 A | 2/1988 | Luly et al. |
| 4,826,815 A | 5/1989 | Luly et al. |
| 5,260,277 A | 11/1993 | McKenzie |
| 5,314,902 A | 5/1994 | Tjoeng et al. |
| 5,434,188 A | 7/1995 | Boschelli et al. |
| 5,770,573 A | 6/1998 | Arrhenius et al. |
| 6,239,108 B1 | 5/2001 | Lin et al. |
| 6,248,713 B1 | 6/2001 | Lin et al. |
| 6,596,687 B1 | 7/2003 | Lin et al. |

FOREIGN PATENT DOCUMENTS

| | | |
|---|---|---|
| DE | 43 09 867 | 9/1994 |
| EP | 0 021 234 | 1/1981 |
| EP | 0 460 679 | 12/1991 |
| EP | 0 519 748 | 12/1992 |
| EP | 0 565 896 | 10/1993 |
| WO | WO 89/09786 | 10/1989 |
| WO | WO 91/09837 | 7/1991 |
| WO | WO 92 00995 | 1/1992 |
| WO | WO 92/00995 | 1/1992 |
| WO | WO 92 08464 | 5/1992 |
| WO | WO 92/08464 | 5/1992 |
| WO | WO 93/08823 | 5/1993 |
| WO | WO 93/09795 | 5/1993 |
| WO | WO 93/12809 | 7/1993 |
| WO | WO 93 12809 | 7/1993 |
| WO | WO 94/02445 | 2/1994 |
| WO | WO 94/15958 | 7/1994 |
| WO | WO 94 23714 | 10/1994 |
| WO | WO 94/23714 | 10/1994 |
| WO | WO 95/15973 | 12/1994 |
| WO | WO 95/15973 | 6/1995 |

OTHER PUBLICATIONS

U.S. patent application No. 09/482,296; Jan. 13, 2000.
Abraham, W.M., et al., "I4–Intergrins Mediate Antigen–induced Late Bronchial Responses and Prolonged Airway Hyperresponsiveness in Sheep", Journal of Clinical Investigation, vol. 93, No. 2, pp. 776–787 (1994).
Bajusz, et al., "Design and synthesis of Peptide Inhibitors of Blood Coagulation", Folia Haematol, Leipzig, vol. 109 pp: 16–21 (1982).
Baldwin, J.E., et al., CA 108: 127408t, 1998.
Chen, S.T., et al., CA 115:159749r, 1991.
Chisholm, P.L., et al., "Monoclonal antibodies to the integrin α–4 subunit inhibit the murine contact hypersensitivity response", Eur. J. Immunol. vol. 23, pp. 682–688, (1993).
Elices, M.J., et al., "Expression and Functional Significance of Alternatively Spliced CS1 Fibronectin in Rheumatoid Arthritis Microvasculature,", Journal of Clinical Investigation, vol. 93, No. 1, pp. 405–416 (1994).
Ferguson, T.A., et al., "Two integrin–binding peptides abrogate T cell–mediated immune responses in vivo", Proc. Natl. Acad. Sci. USA, vol. 88, pp. 8072–8076 (1991).
Ferguson, T.A. et al., "Antigen–Independent Processes in Antigen–Specific Immunity", Journal of Immunology, vol. 150, No. 4, pp. 1172–1182 (1993).
Goodman, et al., "Synthesis and Conformation of Sequential Polypeptides of L–Alanine and J–Aminobutyric Acid", Macromolecules, vol. 9, No. 1, pp. 1–6, (1976).
Goodman & Gilman's, "The Pharmacological Basis of Therapeutics", 6$^{th}$ Edition, MacMillan Publishing, Inc., Appendix 3, pp: 1738–1740 (1980).
Greenstein et al., "Chemistry of the Amino Acids," John Wiley and Sons, Inc., vol. 2, pp 1162–1186.
Gruszecki, W., et al., "Diacylamines—perfekte Acylierungsmittel für die Peptidsynthesis", Liebigs Ann. Chem., pp 331–336, 1988.
Helmer, M.E., "VLA Proteins in the Integrin Family: Structures, Functions, and their Role in Leukocytes", Annual Review of Immunology, vol. 8, pp. 365–400 (1990).

(Continued)

Primary Examiner—Karen Cochrane Carlson
Assistant Examiner—Samuel Wei Lou
(74) Attorney, Agent, or Firm—Steptoe & Johnson LLP

(57) ABSTRACT

The present invention relates to novel compounds that are useful for inhibition and prevention of cell adhesion and cell adhesion-mediated pathologies. This invention also relates to pharmaceutical formulations comprising these compounds and methods of using them for inhibition and prevention of cell adhesion and cell adhesion-mediated pathologies. The compounds and pharmaceutical compositions of this invention can be used as therapeutic or prophylactic agents. They are particularly well-suited for treatment of many inflammatory and autoimmune diseases.

38 Claims, No Drawings

OTHER PUBLICATIONS

Jiang, J., et al., "Approaches Toward the Total Synthesis of Astins A, B, and C", Tetrahedron Letters, vol. 35, No. 14, pp 2121–2124, (1994).

Kim, et al., "Inhibition of $^{125}$I–Labeled Ristocetin Binding to *Micrococcus luteus* Cells by the Peptides Related to Bacterial Cell Wall Mucopeptide Precursors: Quantitative Structure–Activity Relationships", J. Med. Chem., vol. 32, No. 1, pp. 84–93 (1989).

Komoriya, A., et al., "The Minimal Essential Sequence for a Major Cell Type–specific Adhesion Site (CSI) within the Alternatively Spliced Type III Connecting Segment Domain of Fibronectin Is Leucine–Aspartic Acid–Valine", Journal of Biological Chemistry, vol. 266, No. 23, pp. 15075–15079 (1991).

Lampi, et al., CA 118; 73614t, 1993.

Lobb, R.R. and Hemler, M.E., "The Pathophysiologic Role of α4 Integrins In Vivo", The American Society for Clinical Investigation, Inc., vol. 94, pp. 1722–1728 (1994).

Molossi, S., et al., "Blockade of Very Late Antigen–4 Integrin Binding of Fibronectin with Connecting Segment–1 Peptide Reduces Accelerated Coronary Arteriopathy in Rabbit Cardiac Allografts", The American Society for Clinical Investigation, Inc., vol., 95, pp. 2601–2610 (1995).

Morales–Ducret, J., et al., "$α_4β_1$ Integrin (VLA–4) Ligands in Arthritis, Vascular Cell Adhesion Molecule–Expression in Synovium and on Fibroblast–Like Synoviocytes", Journal of Immunology, vol. 149, No. 4, pp. 1424–1431 (1992).

Narumiya, et al., "Pre–B Cells Adhere to Fibronectin Via Interactions of Intergrin α5/αv with RGDS as well as of Integrin α4 with two Distinct V Region Sequences at its Different Binding Sites", International Immunology, vol. 6, No. 1 pp: 139–147 (1994).

Nowlin, D.M., et al. "A Novel Cyclic Peptide Inhibits α4β1 and α5β1 Integrin–mediated Cell Adhesion", Journal of Biological Chemistry, vol. 268, No. 27, pp. 20352–20359 (1993).

Sawyer, "Peptidomimetic Design and Chemical Approaches to Peptide Metabolism", Peptide–Based Drug Design, American Chemical Society, Washington, DC, Chapter 17, pp. 387–410 (1995).

Subasinghe, et al., "Synthesis and Acyclic and Dehydroaspartic Acid Analogues of Ac–Asp–Glu–OH and Their Inhibition of Rat Brain N–Acetylated I–Linked Acidic Dipeptidase (NAALA Dipeptidase)", Journal of Medicinal Chemistry, vol. 33, No. 10, pp. 2734–2744 (1990).

Thierry et al., "Synthesis and Activity of NAcSerAspLysPro Analogues on Cellular Interactions between T–Cell and Erythrocytes in ROAette Formation," Journal of Medical Chemistry, 1990, vol. 33, pp. 2122–2127.

Wayner, E.A. and Kovach, N.L., "Activation–dependent recognition by Hematopoietic Cells of the LDV Sequence in the V Region of Fibronectin", The Journal of Cell Biology, vol. 116, No. 2, pp. 489–497 (1992).

Yednock, T.A., et al, "Prevention of Experimental Autoimmune Encephalomyelitis by Antibodies against α4β1 Integrin", Nature, vol. 356, No. 6364, pp. 63–66 (1992).

T.K. Sawyer; "Peptidomimetic Design and Chemical Approaches to Peptide Metabolism", Peptide–Based Drug Design, American Chemical Society, Washington DC, Chapter 17, pp. 387–410 (1995).

"Synthesis and Activity of NAcSerAspLysPro Analogues on Cellular Interactions between T–Cell and Erythrocytes in Rosette Formation," Thierry et al., Journal of Medical Chemistry, 1990, vol. 33, pp 2122–2127.

"Chemistry of the Amino Acids," Greenstein et al., John Wiley and Sons, Inc., vol. 2, pp 1162–1186.

"Inhibition of $^{125}$I–Labeled Ristocetin Binding to Micrococcus Luteus Cells by the Peptides Related to Bacterial Cell Wall Mucopeptide Precursors: Quantitative Structure–Activity Relationships," Journal Medical Chemistry, 1989, vol. 32, pp 85–93.

Abraham et al., "$α_4$–Integrins Mediate Antigen–induced Late Bronchial Responses and Prolonged Airway Hyperresponsiveness in Sheep", *The Journal of Clinical Investigation*, 93:776–787, 1994.

Bajusz et al., "Design and Synthesis of Peptide Inhibitors of Blood Coagulation", *Folia Haematol. Leipzig*, 109:16–21, 1982.

Baldwin et al., CA 108: 127408t, 1988.

Chen et al., AAPP 115: 159756r, 1991.

Chisholm et al., "Monoclonal antibodies to the integrin α–4 subunit inhibit the murine contact hypersensitivity response", *European Journal of Immunology*, 23:682–688, 1993.

Elices et al., "Expression and Functional Significance of Alternatively Spliced CS1 Fibronectin in Rheumatoid Arthritis Microvasculature", *The Journal of Clinical Investigation*, 93:405–416, 1994.

Ferguson et al., "Two integrin–binding peptides abrogate T cell–mediated immune responses in vivo", *Proceedings of the National Academy of Sciences USA*, 88:8072–8076, 1991.

Ferguson et al., "Antigen–Independent Processes in Antigen–Specific Immunity", *The Journal of Immunology*, 150:1172–1182, 1993.

Goodman et al., "Synthesis and Conformation of Sequential Polypeptides of L–alanine and beta–Aminobutyric Acid", *Macromolecules*, 9:1–6, 1976.

Goodman et al., "Drug Interactions", *The Pharmacological Basis of Therapeutics*, 1738–1740, 1980.

Gruszecki et al., "Diacylamine–perfekte Acylierungsmittel für die Peptidsynthese", *Liebigs Ann. Chem.*, pp. 331–336, 1988.

Hemler, "VLA Proteins in the Integrin Family: Structures. Functions. and Their Role on Leukocytes", *Annual Review of Immunology*, 8:365–400, 1990.

Jiang et al., "Approaches Toward the Total Synthesis of Astins A, B, And C", *Tetrahedron Letters*, 35:2121–4, 1994.

Komoriya et al., "The Minimal Essential Sequence for a Major Cell Type–specific Adhesion site (CSI) within the Alternatively Spliced . . . ", *Journal of Biological Chemistry*, 266:15075–15079, 1991.

Lampi et al., CA 118: 73614t, 1993.

Lobb et al., "The Pathophysiologic Role of α4 Integrins in Vivo", *The Journal of Clinical Investigation*, 94:1722–1728, 1994.

Molossi et al., "Blockade of Very Late Antigen–4 Integrin Binding to Fibronectin with Connecting Segment–1 Peptide Reduces Accelerated Coronary Arteriopathy . . . ", *Journal of Clinical Investigation*, 95:2601–2610, 1995.

Morales–Ducret et al., "$α_4β_1$ Integrin (VLA–4) Ligands in Arthritis Vascular Cell Adhesion Molecular–1 Expression in Synovium and on . . . ", *The Journal of Immunology*, 149:1424–1431, 1992.

Narumiya et al., "Pre–B cells adhere to fibronectin via interactions of integrin α5/αv with RGDS as well as of integrin α4 with two distinct V region sequences at its different . . . ", *Intl. Immun.*, 6:139–147, 1994.

Nowlin et al., "A Novel Cyclic Pentapeptide Inhibits α4β1 and α5β1 Integrin–mediated Cell Adhesion", *The Journal of Biological Chemistry*, 268:20352–20359, 1993.

Subasinghe et al., "Synthesis and Acyclic and Dehydroaspartic Acid Analogues of Ac–Asp–Glu–OH and Their Inhibition of Rat Brain N–Acetylated alpha–Linked Acidic Dipeptidase (NAALA Dipeptidase)", *Journal of Medical Chemistry*, 33:2734–44, 1990.

Wayner et al., "Activation–dependent Recognition by Hematopoietic Cells of the LDV Sequence in the V Region of Fibronectin", *The Journal of Cell Biology*, 116:489–497, 1992.

Yednock et al., "Prevention of experimental autoimmune encephalomyelitis by antibodies against α4β1 integrin", *Nature*, 356:63–66, 1992.

CELL ADHESION INHIBITORS

CROSS REFERENCE TO RELATED APPLICATIONS

This application is a continuation of U.S. application Ser. No. 08/983,391, filed on Aug. 10, 1998 now U.S. Pat. No. 6,239,108, which claims priority from PCT/US96/11570 filed on Jul. 11, 1996, and from U.S. application Ser. No. 08/498,237, filed on Jul. 11, 1995, each of which is incorporated by reference in its entirety.

TECHNICAL FIELD OF THE INVENTION

The present invention relates to novel compounds that are useful for inhibition and prevention of cell adhesion and cell adhesion-mediated pathologies. This invention also relates to pharmaceutical formulations comprising these compounds and methods of using them for inhibition and prevention of cell adhesion and cell adhesion-mediated pathologies. The compounds and pharmaceutical compositions of this invention can be used as therapeutic or prophylactic agents. They are particularly well-suited for treatment of many inflammatory and autoimmune diseases.

BACKGROUND OF THE INVENTION

Cell adhesion is a process by which cells associate with each other, migrate towards a specific target or localize within the extra-cellular matrix. As such, cell adhesion constitutes one of the fundamental mechanisms underlying numerous biological phenomena. For example, cell adhesion is responsible for the adhesion of hematopoietic cells to endothelial cells and the subsequent migration of those hemopoietic cells out of blood vessels and to the site of injury. As such, cell adhesion plays a role in pathologies such as inflammation and immune reactions in mammals.

Investigations into the molecular basis for cell adhesion have revealed that various cell-surface macromolecules—collectively known as cell adhesion molecules or receptors—mediate cell-cell and cell-matrix interactions. For example, proteins of the superfamily called "integrins" are key mediators in adhesive interactions between hematopoietic cells and their microenvironment (M. E. Hemler, "VLA Proteins in the Integrin Family: Structures, Functions, and Their Role on Leukocytes.", *Ann. Rev. Immunol.*, 8, p. 365 (1990)). Integrins are non-covalent heterodimeric complexes consisting of two subunits called α and β. There are at least 12 different α subunits (α1, α2, α3, α4, α5, α6, αL, αM, αX, αIIB, αV, and αE) and at least 9 different β (β1–β9) subunits. Based on the type of its α and β subunit components, each integrin molecule is categorized into a subfamily.

α4β1 integrin, also known as very late antigen-4 ("VLA-4") or CD49d/CD29, is a leukocyte cell surface receptor that participates in a wide variety of both cell-cell and cell-matrix adhesive interactions (M. E. Hemler, *Ann. Rev. Immunol.*, 8, p. 365 (1990)). It serves as a receptor for the cytokine-inducible endothelial cell surface protein, vascular cell adhesion molecule-1 ("VCAM-1"), as well as to the extracellular matrix protein fibronectin ("FN") (Ruegg et al., *J. Cell Biol.*, 177, p. 179 (1991); Wayner et al., *J. Cell Biol.*, 105, p. 1873 (1987); Kramer et al., *J. Biol. Chem.*, 264, p. 4684 (1989); Gehlsen et al. *Science*, 24, p. 1228 (1988)). Anti-VLA4 monoclonal antibodies ("mAb's") have been shown to inhibit VLA4-dependent adhesive interactions both in vitro and in vivo (Ferguson et al. *Proc. Natl. Acad. Sci.*, 88, p. 8072 (1991); Ferguson et al., *J. Immunol.*, 150, p. 1172 (1993)). Results of in vivo experiments suggest that this inhibition of VLA-4-dependent cell adhesion may prevent or inhibit several inflammatory and autoimmune pathologies (R. L. Lobb et al., "The Pathophysiologic Role of α4 Integrins In Vivo", *J. Clin. Invest.*, 94, pp. 1722–28 (1994)).

In order to identify the minimum active amino acid sequence necessary to bind VLA-4, Komoriya et al. ("The Minimal Essential Sequence for a Major Cell Type-Specific Adhesion Site (CS1) Within the Alternatively Spliced Type III Connecting Segment Domain of Fibronectin Is Leucine-Aspartic Acid-Valine", *J. Biol. Chem.*, 266 (23), pp. 15075–79 (1991)) synthesized a variety of overlapping peptides based on the amino acid sequence of the CS-1 region (the VLA-4 binding domain) of a particular species of fibronectin. They identified an 8-amino acid peptide, Glu-Ile-Leu-Asp-Val-Pro-Ser-Thr [SEQ ID NO: 1], as well as two smaller overlapping pentapeptides, Glu-Ile-Leu-Asp-Val [SEQ ID NO: 2] and Leu-Asp-Val-Pro-Ser [SEQ ID NO: 3], that possessed inhibitory activity against FN-dependent cell adhesion. These results suggested the tripeptide Leu-Asp-Val as a minimum sequence for cell-adhesion activity. It was later shown that Leu-Asp-Val binds only to lymphocytes that express an activated form of VLA-4, thus bringing into question the utility of such a peptide in vivo (E. A. Wayner et al., "Activation-Dependent Recognition by Hematopoietic Cells of the LDV Sequence in the V Region of Fibronectin", *J. Cell. Biol.*, 116(2), pp. 489–497 (1992)). However, certain larger peptides containing the LDV sequence were subsequently shown to be active in vivo [T. A. Ferguson et al., "Two Integrin Binding Peptides Abrogate T-cell-Mediated Immune Responses In Vivo", *Proc. Natl. Acad. Sci. USA*, 88, pp. 8072–76 (1991); and S. M. Wahl et al., "Synthetic Fibronectin Peptides Suppress Arthritis in Rats by Interrupting Leukocyte Adhesion and Recruitment", *J. Clin. Invest.*, 94, pp. 655–62 (1994)].

A cyclic pentapeptide, Arg-Cys-Asp-TPro-Cys (wherein TPro denotes 4-thioproline) (SEQ ID NO:5), which can inhibit both VLA-4 and VLA-5 adhesion to FN has also been described (D. M. Nowlin et al. "A Novel Cyclic Pentapeptide Inhibits α4β1 and α5β1 Integrin-mediated Cell Adhesion", *J. Biol. Chem.*, 268(27), pp. 20352–59 (1993); and PCT publication PCT/US91/04862). This peptide was based on the tripeptuide sequence Arg-Gly-Asp from FN which had been known as a common motif in the recognition site for several extracellular-matrix proteins.

Despite these advances, there remains a need for small, specific inhibitors of VLA-4-dependent cell adhesion. Ideally, such inhibitors would be semi-peptidic or non-peptidic so that they may be orally administered. Such compounds would provide useful agents for treatment, prevention or suppression of various pathologies mediated by cell adhesion and VLA-4 binding. co-pending/United States patent application 08/376,372 describes β-amino acid containing linear peptidyl compounds with cell adhesion inhibitory activity. International patent applications WO 94/15958 and WO 92/00995 describe cyclic peptide and peptidomimetic compounds with cell adhesion modulating activity. International patent applications WO 93/08823 and WO 92/08464 describe guanidinyl-, urea- and thiourea-containing cell adhesion modulating compounds. U.S. Pat. No. 5,260,277 describes guanidinyl cell adhesion modulation compounds.

SUMMARY OF THE INVENTION

The present invention solves this problem by providing novel semi-peptidic compounds that inhibit the binding of ligands to VLA-4. These compounds are useful for inhibition, prevention and suppression of VLA-4-mediated cell adhesion and pathologies associated with that adhesion, such as inflammation and immune reactions. The compounds of this invention may be used alone or in combination with other therapeutic or prophylactic agents to inhibit, prevent or suppress cell adhesion. This invention also provides pharmaceutical formulations containing these VLA-4-mediated cell adhesion inhibitors and methods of using the compounds and compositions of the invention for inhibition of cell adhesion.

According to one embodiment of this invention, these novel compounds, compositions and methods are advantageously used to treat inflammatory and immune diseases. The present invention also provides methods for preparing the compounds of this invention and intermediates useful in those methods.

DETAILED DESCRIPTION OF THE INVENTION

The following abbreviations are used in the description:

| Designation | Reagent or Fragment |
| --- | --- |
| Ac | acetyl |
| Bn | benzyl |
| Boc | tert-butoxycarbonyl |
| Bu | butyl |
| Cbz | carbobenzyloxy |
| Cy | cyclohexyl |
| CyM | cyclohexylmethyl |
| DIPEA | diisopropylethylamine |
| EDC | 1-(3-diethylaminopropyl)-3-ethylcarbodiimide |
| HOBT | 1-hydroxybenzotriazole hydrate |
| i-amyl | isoamyl |
| i-Pn | isopentyl |
| i-Pr | isopropyl |
| Me | methyl |
| 2-MPUBA | 4-(N'-(2-methylphenyl)urea)-phenylmethylamino |
| 2-MPUPA | 4-(N'-(2-methylphenyl)urea)-phenylacetyl |
| NMP | N-methylpyrrolidinone |
| NMM | N-methylmorpholine |
| Ph | phenyl |
| PUPA | 4-(N'-phenylurea)phenylacetyl |
| Su | succinimidyl |
| TBTU | 2-(1H-benzotriazol-1-yl)-1,1,3,3-tetramethyluronium tetrafluoroborate |
| TEA | triethylamine |
| TFA | trifluoroacetic acid |
| THAM | tris(hydroxy)methylaminomethane |

Definitions

As used herein, the term "alkyl", alone or in combination, refers to a straight-chain or branched-chain alkyl radical containing from 1 to 10, preferably from 1 to 6 and more preferably from 1 to 4, carbon atoms. Examples of such radicals include, but are not limited to, methyl, ethyl, n-propyl, isopropyl, n-butyl, isobutyl, sec-butyl, tert-butyl, pentyl, iso-amyl, hexyl, decyl and the like.

The term "alkenyl", alone or in combination, refers to a straight-chain or branched-chain alkenyl radical containing from 2 to 10, preferably from 2 to 6 and more preferably from 2 to 4, carbon atoms. Examples of such radicals include, but are not limited to, ethenyl, E- and Z-propenyl, isopropenyl, E- and Z-butenyl, E- and Z-isobutenyl, E- and Z-pentenyl, decenyl and the like.

The term "alkynyl", alone or in combination, refers to a straight-chain or branched-chain alkynyl radical containing from 2 to 10, preferably from 2 to 6 and more preferably from 2 to 4, carbon atoms. Examples of such radicals include, but are not limited to, ethynyl (acetylenyl), propynyl, propargyl, butynyl, hexynyl, decynyl and the like.

The term "cycloalkyl", alone or in combination, refers to a cyclic alkyl radical containing from 3–10, preferably from 3–8 and more preferably from 3–6, carbon atoms and may be optionally aryl-fused. Examples of such radicals include, but are not limited to, cyclopropyl, cyclobutyl, cyclopentyl, cyclohexyl and the like.

The term "cycloalkenyl", alone or in combination, refers to a cyclic carbocycle containing from 4 to 8, preferably 5 or 6, carbon atoms and one or more double bonds. Examples of such cycloalkenyl radicals include, but are not limited to, cyclopentenyl, cyclohexenyl, cyclopentadienyl and the like.

The term "aryl" refers to a carbocyclic aromatic group selected from the group consisting of phenyl, naphthyl, indenyl, indanyl, azulenyl, fluorenyl, and anthracenyl; or a heterocyclic aromatic group selected from the group consisting of furyl, thienyl, pyridyl, pyrrolyl, oxazolyly, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, pyrazolo[1,5-c]triazinyl and the like.

"Aryl", "cycloalkyl" and "cycloalkenyl" groups, as defined in this application may independently contain up to three substituents which are independently selected from the group consisting of halogen, hydroxyl, amino, nitro, trifluoromethyl, trifluoromethoxy, alkyl, alkenyl, alkynyl, cyano, carboxy, carboalkoxy, Ar'-substituted alkyl, Ar'-substituted alkenyl or alkynyl, 1,2-dioxymethylene, 1,2-dioxyethylene, alkoxy, alkenoxy or alkynoxy, Ar'-substituted alkoxy, Ar'-substituted alkenoxy or alkynoxy, alkylamino, alkenylamino or alkynylamino, Ar'-substituted alkylamino, Ar'-substituted alkenylamino or alkynylamino, Ar'-substituted carbonyloxy, alkylcarbonyloxy, aliphatic or aromatic acyl, Ar'-substituted acyl, Ar'-substituted alkylcarbonyloxy, Ar'-substituted carbonylamino, Ar'-substituted amino, Ar'-substituted oxy, Ar'-substituted carbonyl, alkylcarbonylamino, Ar'-substituted alkylcarbonylamino, alkoxy-carbonylamino, Ar'-substituted alkoxycarbonyl-amino, Ar'-oxycarbonylamino, alkylsulfonylamino, mono- or bis-(Ar'-sulfonyl)amino, Ar'-substituted alkyl-sulfonylamino, morpholinocarbonylamino, thiomorpholinocarbonylamino, N-alkyl guanidino, N-Ar' guanidino, N-N-(Ar',alkyl) guanidino, N,N-(Ar',Ar')guanidino, N,N-dialkyl guanidino, N,N,N-trialkyl guanidino, N-alkyl urea, N,N-dialkyl urea, N-Ar' urea, N,N-(Ar',alkyl) urea, N,N-(Ar')$_2$ urea, aralkyloxycarbonyl-substituted alkyl, aralkylaminocarbonyl, thioaryloxy and the like; wherein "Ar'" is defined similarly to aryl, but contains up to three substituents selected from the group consisting of halogen, hydroxyl, amino, nitro, trifluoromethyl, trifluoromethoxy, alkyl, alkenyl, alkynyl, 1,2-dioxymethylene, 1,2-dioxyethylene, alkoxy, alkenoxy, alkynoxy, alkylamino, alkenylamino or alkynylamino, alkylcarbonyloxy, aliphatic or aromatic acyl, alkylcarbonylamino, alkoxycarbonylamino, alkylsulfonylamino, N-alkyl or N,N-dialkyl urea.

The term "aralkyl", alone or in combination, refers to an aryl substituted alkyl radical, wherein the term "alkyl" and "aryl" are as defined above. Examples of suitable aralkyl radicals include, but are not limited to, phenylmethyl, phenethyl, phenylhexyl, diphenylmethyl, pyridylmethyl, tetrazolylmethyl, furylmethyl, imidazolylmethyl, indolylmethyl, thienylpropyl and the like.

The term "alkoxy", alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkenoxy", alone or in combination, refers to a radical of formula alkenyl-O—, wherein the term "alkenyl" is as defined above provided that the radical is not an enol ether. Examples of suitable alkenoxy radicals include, but are not limited to, allyloxy, E- and Z-3-methyl-2-propenoxy and the like.

The term "alkynyloxy", alone or in combination, refers to a radical of formula alkynyl-O—, wherein the term "alkynyl" is as defined above provided that the radical is not an ynol ether. Examples of suitable alkynoxy radicals include, but are not limited to, propargyloxy, 2-butynyloxy and the like.

The term "thioalkoxy" refers to a thioether radical of formula alkyl-S—, wherein alkyl is as defined above.

The term "alkylamino", alone or in combination, refers to a mono- or di-alkyl-substituted amino radical (i.e., a radical of formula alkyl-NH— or (alkyl)$_2$-N—), wherein the term "alkyl" is as defined above. Examples of suitable alkylamino radicals include, but are not limited to, methylamino, ethylamino, propylamino, isopropylamino, t-butylamino, N,N-diethylamino and the like.

The term "alkenylamino", alone or in combination, refers to a radical of formula alkenyl-NH— or (alkenyl)$_2$N—, wherein the term "alkenyl" is as defined above, provided that the radical is not an enamine. An example of such alkenylamino radicals is the allylamino radical.

The term "alkynylamino", alone or in combination, refers to a radical of formula alkynyl-NH— or (alkynyl)$_2$N—, wherein the term "alkynyl" is as defined above, provided that the radical is not an ynamine. An example of such alkynylamino radicals is the propargyl amino radical.

The term "aryloxy", alone or in combination, refers to a radical of formula aryl-O—, wherein aryl is as defined above. Examples of aryloxy radicals include, but are not limited to, phenoxy, naphthoxy, pyridyloxy and the like.

The term "arylamino", alone or in combination, refers to a radical of formula aryl-NH—, wherein aryl is as defined above. Examples of arylamino radicals include, but are not limited to, phenylamino (anilido), naphthylamino, 2-, 3- and 4-pyridylamino and the like.

The term "biaryl", alone or in combination, refers to a radical of formula aryl-aryl-, wherein the term "aryl" is as defined above.

The term "thioaryl", alone or in combination, refers to a radical of formula aryl-S—, wherein the term "aryl" is as defined above. An example of a thioaryl radical is the thiophenyl radical.

The term "aryl-fused cycloalkyl", alone or in combination, refers to a cycloalkyl radical which shares two adjacent atoms with an aryl radical, wherein the terms "cycloalkyl" and "aryl" are as defined above. An example of an aryl-fused cycloalkyl radical is the benzo-fused cyclobutyl radical.

The term "aliphatic acyl", alone or in combination, refers to radicals of formula alkyl-CO—, alkenyl-CO— and alkynyl-CO— derived from an alkane-, alkene- or alkyn-carboxylic acid, wherein the terms "alkyl", "alkenyl" and "alkynyl" are as defined above. Examples of such aliphatic acyl radicals include, but are not limited to, acetyl, propionyl, butyryl, valeryl, 4-methylvaleryl, acryloyl, crotyl, propiolyl, methylpropiolyl and the like.

The terms "aromatic acyl" or "aroyl", alone or in combination, refers to a radical of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl and the like.

The term "heterocycloyl", alone or in combination, refers to radicals of formula heterocycle-CO—, wherein the term "heterocycle" is as defined below. Examples of suitable heterocycloyl radicals include but are not limited to, tetrahydrofuranylcarbonyl, piperidinylcarbonyl, tetrahydrothiophenecarbonyl and the like.

The terms "morpholinocarbonyl" and "thiomorpholinocarbonyl", alone or in combination with other terms, refer to an N-carbonylated morpholino and an N-carbonylated thiomorpholino radical, respectively.

The term "alkylcarbonylamino", alone or in combination, refers to a radical of formula alkyl-CONH, wherein the term "alkyl" is as defined above.

The term "alkoxycarbonylamino", alone or in combination, refers to a radical of formula alkyl-OCONH—, wherein the term "alkyl" is as defined above.

The term "alkylsulfonylamino", alone or in combination, refers to a radical of formula alkyl-SO$_2$NH—, wherein the term "alkyl" is as defined above.

The term "arylsulfonylamino", alone or in combination, refers to a radical of formula aryl-SO$_2$NH—, wherein the term "aryl" is as defined above.

The term "N-alkylurea", alone or in combination, refers to a radical of formula alkyl-NH—CO—NH—, wherein the term "alkyl" is as defined above.

The term "N-arylurea", alone or in combination, refers to a radical of formula aryl-NH—CO—NH—, wherein the term "aryl" is as defined above.

The term "halogen" means fluorine, chlorine, bromine and iodine.

The terms "heterocycle" and "heterocyclic ring", alone or in combination, refer to a non-aromatic 3- to 10-membered ring containing at least one endocyclic N, O or S atom. The heterocycle may optionally be aryl-fused. The heterocycle may also be optionally substituted with one to three substituents which are independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, Ar'-substituted alkyl, Ar'-substituted alkenyl or alkynyl, 1,2-dioxymethylene, 1,2-dioxyethylene, alkoxy, alkenoxy or alkynoxy, Ar'-substituted alkoxy, Ar'-substituted alkenoxy or alkynoxy, alkylamino, alkenylamino or alkynylamino, Ar'-substituted alkylamino, Ar'-substituted alkenylamino or alkynylamino, Ar'-substituted carbonyloxy, alkylcarbonyloxy, aliphatic or aromatic acyl, Ar'-substituted acyl, Ar'-substituted alkylcarbonyloxy, Ar'-substituted carbonylamino, Ar'-substituted amino, Ar'-substituted oxy, Ar'-substituted carbonyl, alkylcarbonylamino, Ar'-substituted alkylcarbonylamino, alkoxy-carbonylamino, Ar'-substituted alkoxycarbonyl-amino, Ar'-oxycarbonylamino, alkylsulfonylamino, mono- or bis-(Ar'-sulfonyl)amino, Ar'-substituted alkyl-sulfonylamino, morpholinocarbonylamino, thiomorpholinocarbonylamino, N-alkyl guanidino, N-Ar' guanidino, N-N-(Ar',alkyl) guanidino, N,N-(Ar',Ar')guanidino, N,N-dialkyl guanidino, N,N,N-trialkyl guanidino, N-alkyl urea, N,N-dialkyl urea, N-Ar' urea, N,N-(Ar',alkyl) urea, N,N-(Ar')$_2$ urea, aralkoxycarbonyl-substituted alkyl, carboxyalkyl, oxo, arylsulfonyl and aralkylaminocarbonyl.

The term "leaving group" generally refers to groups readily displaceable by a nucleophile, such as an amine, and alcohol or a thiol nucleophile. Such leaving groups are well known and include carboxylates, N-hydroxysuccinimide, N-hydroxybenzotriazole, halogen (halides), triflates, tosylates, mesylates, alkoxy, thioalkoxy and the like.

The term "hydrophobic group" refers to a group which is resistant to uniting with or absorbing water. Examples of such hydrophobic groups include, but are not limited to, methyl, ethyl, propy, butyl, pentyl, hexyl, phenyl, benzyl, naphthyl, N-benzylimidazolyl, methylthioethyl and the like.

The term "acidic functional group" refers to a group which has an acidic hydrogen within it. Examples of such groups include, but are not limited to, carboxylic acid, tetrazole, imidazole, hydroxyl, mercapto, hydroxylaminocarbonyl, sulfonic acid, sulfinic acid, phosphoric acid and phosphonic acid.

The terms "activated derivative of a suitably protected α-amino acid" and "activated substituted-phenylacetic acid derivative" refer to derivatives of carboxylic acids wherein the —OH group is replaced by a superior leaving group. Examples of activated acid derivatives include, but are not limited to, the corresponding acyl halides (e.g. acid fluoride, acid chloride and acid bromide), corresponding activated esters (e.g. nitrophenyl ester, the ester of 1-hydroxybenzotriazole, HOBT, or the ester of hydroxysuccinimide, HOSu), and other conventional derivatives within the skill of the art.

The terms "protected" or "protecting group" refer to a suitable chemical group which may be attached to a functional group of a molecule, then removed at a later stage to reveal the intact functional group and molecule. Examples of suitable protecting groups for various functional groups are described in T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995).

The compounds of this invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are envisioned as part of the invention. Although amino acids and amino acid side chains may be depicted in a particular configuration, both natural and unnatural forms are envisioned as part of the invention.

In view of the above definitions, other chemical terms used throughout this application can be easily understood by those of skill in the art. Terms may be used alone or in any combination thereof. The preferred and more preferred chain lengths of the radicals apply to all such combinations.

This invention provides compounds which are capable of inhibiting VLA-4-mediated cell adhesion by inhibiting the binding of ligands to that receptor. These compounds are represented by formula (I):

$$Z—(Y^1)—(Y^2)—(Y^3)—X \quad (I)$$

and pharmaceutically acceptable derivatives thereof; wherein:

Z is selected from the group consisting of alkyl; aliphatic acyl optionally substituted with N-alkyl- or N-arylamido; aroyl; heterocycloyl; alkyl- or arylsulfonyl; aralkylcarbonyl optionally substituted with aryl; heterocycloalkylcarbonyl; alkoxycarbonyl; aralkyloxycarbonyl; cycloalkylcarbonyl optionally fused with aryl; heterocycloalkoxycarbonyl; alkylaminocarbonyl; arylamino carbonyl and aralkylaminocarbonyl optionally substituted with bis(alkylsulfonyl)amino, alkoxycarbonylamino or alkenyl; alkylsulfonyl; aralkylsulfonyl; arylsulfonyl; cycloalkylsulfonyl optionally fused with aryl; heterocyclylsulfonyl; heterocyclylalkylsulfonyl; aralkoxycarbonyl; aryloxycarbonyl; cycloalkyloxycarbonyl; heterocyclyloxycarbonyl; heterocyclylalkoxycarbonyl; mono- or di-alkylaminocarbonyl optionally substituted with aryl; (alkyl) (aralkyl)aminocarbonyl; mono- or di-aralkylaminocarbonyl; mono- or di-arylaminocarbonyl; (aryl) (alkyl)aminocarbonyl; mono- or di-cycloalkylaminocarbonyl; heterocyclylaminocarbonyl; heterocyclylalkylaminocarbonyl; (alkyl) (heterocyclyl) aminocarbonyl; (alkyl) (heterocyclylalkyl)aminocarbonyl; (aralkyl) (heterocyclyl)aminocarbonyl; (aralkyl) (heterocyclylalkyl)aminocarbonyl; alkenoyl optionally substituted with aryl; alkenylsulfonyl optionally substituted with aryl; alkynoyl optionally substituted with aryl; alkynylsulfonyl optionally substituted with aryl; cycloalkenylcarbonyl; cycloalkenylsulfonyl; cycloalkylalkanoyl; cycloalkylalkylsulfonyl; arylaroyl; biarylsulfonyl; alkoxysulfonyl; aralkoxysulfonyl; alkylaminosulfonyl; aryloxysulfonyl; arylaminosulfonyl; N-arylurea-substituted alkanoyl; N-arylurea-substituted alkylsulfonyl; cycloalkenyl-substituted carbonyl; cycloalkenyl-substituted sulfonyl; alkenoxycarbonyl optionally substituted with aryl; alkenoxysulfonyl optionally substituted with aryl; alkynoxycarbonyl optionally substituted with aryl; alkynoxysulfonyl optionally substituted with aryl; alkenyl- or alkynylaminocarbonyl optionally substituted with aryl; alkenyl- or alkynyl-aminosulfonyl optionally substituted with aryl; acylamino-substituted alkanoyl; acylamino-substituted alkylsulfonyl; aminocarbonyl-substituted alkanoyl; carbamoyl-substituted alkanoyl; carbamoyl-substituted alkylsulfonyl; heterocyclylalkanoyl; heterocyclylaminosulfonyl; carboxyalkyl-substituted aralkoyl; carboxyalkyl-substituted aralkylsulfonyl; oxocarbocyclyl-fused aroyl; oxocarbocyclyl-fused arylsulfonyl; heterocyclylalkanoyl; N',N'-alkyl, arylhydrazinocarbonyl; aryloxy-substituted alkanoyl and heterocyclylalkylsulfonyl.

$Y^1$ is —N(R$^1$)—C(R$^2$)(A$^1$)—C(O)—;

$Y^2$ is —N(R$^1$)—C(R$^2$)(A$^2$)—C(O)—;

each $Y^3$ is represented by the formula —N(R$^1$)—C(R$^2$)(A$^3$)—C(O)—;

each R$^1$ is independently selected from the group consisting of hydrogen, alkyl, and aralkyl; alkenyl; alkynyl; cycloalkyl; cycloalkenyl; cycloalkylalkyl; aryl; aminoalkyl; mono- or di-alkyl-substituted aminoalkyl; mono- or di-aralkyl-substituted aminoalkyl; hydroxyalkyl; alkoxyalkyl; mercaptoalkyl; thioalkoxyalkyl A$^1$ is selected from the group consisting of amino acid side chains and corresponding protected derivatives; cycloalkyl; and alkyl optionally substituted with amino, acylamino, amino-substituted acylamino, alkoxycarbonylamino, aryl, cycloalkyl, carboxy, alkoxy, aralkyloxy, alkoxycarbonyl, aralkoxycarbonyl, aminocarbonyl, alkylaminocarbonyl, dialkylaminocarbonyl, (alkyl) (aralkyl)aminocarbonyl, aralkylaminocarbonyl, diaralkylaminocarbonyl, hydroxyl, carboxyalkylaminocarbonyl, hydroxylaminocarbonyl, mercapto, thioalkoxy or heterocycle;

$A^2$ is selected from the group consisting of acidic functional groups and alkyl optionally substituted with an acidic functional group, protected acidic functional group or aryl;

each $A^3$ is independently selected from the group consisting of amino acid side chains and corresponding protected derivatives; aryl; cycloalkyl; and alkyl optionally substituted with amino, acylamino, amino-substituted acylamino, aryl, cycloalkyl, carboxy, alkoxy, aralkyloxy, alkoxycarbonyl, aralkoxycarbonyl, aminocarbonyl, alkylaminocarbonyl, dialkylaminocarbonyl, (alkyl) (aralkyl) aminocarbonyl, aralkylaminocarbonyl, diaralkylaminocarbonyl, hydroxyl, carboxyalkylaminocarbonyl, hydroxylaminocarbonyl, mercapto, thioalkoxy or heterocycle;

or $R^1$ and any A are taken together with the atoms to which they are attached form a 3- to 6-membered ring heterocycle;

each $R^2$ is independently selected from the group consisting of hydrogen and alkyl;

n is an integer from 0 to 8; and

X is selected from the group consisting of alkoxy; aryloxy; aralkyloxy; hydroxyl; amino; alkylamino optionally substituted with hydroxy, aminocarbonyl, N-alkylaminocarbonyl, carboxy or alkoxycarbonyl; dialkylamino; cycloalkylamino; dicycloalkylamino; cycloalkyla-lkylamino; (alkyl) (aryl)amino; aralkylamino optionally substituted with carboxy; diaralkylamino; arylamino; heterocycle; and (mono- or bis-carboxylic acid)-substituted alkylamine; heterocyclylamino; heterocyclyl-substituted alkylamino and wherein the compound of formula I is expressly not N'-carboxymethyl-N-(phenylacetyl-L-leucyl-L-aspartyl-L-phenylalanyl-L-prolyl)piperazine (i.e., when Z=phenylacetyl, $Y^1$=L, $Y^2$=D, $Y^3$=F/P, n=2, and X=4-carboxymethylpiperazinyl) and expressly not phenylacetyl-L-leucyl-L-aspartyl-L-phenylalanyl-D-proline amide (i.e., when Z=phenylacetyl, $Y^1$=L, $y^2$=D, $Y^3$=F/p, n=2, and X=$NH_2$).

A "pharmaceutically acceptable derivative" denotes any pharmaceutically acceptable salt, ester, salt of such ester, amide or salt of such amide of a compound of this invention. The invention also includes any other compound which, upon administration to a patient, is capable of providing (directly or indirectly) a compound of this invention (e.g. a prodrug). The invention also includes metabolites or residues of a compound of this invention characterized by the ability to inhibit, prevent or suppress cell adhesion and cell adhesion-mediated pathologies.

In a preferred embodiment of this invention, Al is selected from the group consisting of cycloalkyl; heterocyclic ring (when $A^1$ and $R^1$ are taken together); and alkyl optionally substituted with amino, acylamino, amino-substituted acylamino, aryl, carboxy, cycloalkyl, hydroxy, alkoxy, aralkyloxy, alkoxycarbonyl, aralkoxycarbonyl, aminocarbonyl, alkylaminocarbonyl, dialkylaminocarbonyl, (alkyl)(aralkyl)aminocarbonyl, aralkylaminocarbonyl, diaralkylaminocarbonyl, alkoxycarbonylamino, mercapto, thioalkoxy or heterocycle.

More preferably, $A^1$ is selected from the group consisting of aminocarbonylethyl, benzyl, n-butyl, isobutyl, carboxyethyl, cyclohexyl, 1-hydroxyethyl, hydroxymethyl, mercaptomethyl, 1-methylpropyl, methylthioethyl, n-propyl, isopropyl, methoxycarbonylaminobutyl, 6-aminohexanoylaminobutyl and (when $A^1$ and $R^1$ are taken together) azetidine, aziridine, pyrrolidine, and piperidine.

Even more preferably, $A^1$ is selected from the group consisting of benzyl, n-butyl, isobutyl, methylthioethyl, cyclohexyl, 1-methylpropyl, n-propyl and isopropyl. An alternate preferred $A^1$ is (when $A^1$ and $R^1$ are taken together) pyrrolidine.

In an alternate preferred embodiment, $A^2$ is selected from the group consisting of alkyl optionally substituted with amino, aminocarbonyl, aryl, alkoxycarbonyl, aralkyloxycarbonyl, hydroxylaminocarbonyl, carboxy, NH-containing heterocycle, hydroxy, or mercapto; aralkyl optionally substituted with amino, aminocarbonyl, carboxy, NH-containing heterocycle, hydroxy, or mercapto; and heterocyclic ring (when $A^2$ and $R^1$ are taken together).

More preferably, $A^2$ is selected from the group consisting of carboxymethyl, 2-carboxyethyl, 1-carboxyethyl, hydroxylaminocarbonylmethyl, hydroxymethyl, mercaptomethyl, imidazolylmethyl, N-Bn-imidazolylmethyl, phenyl, carbomethoxymethyl, carbobenzyloxymethyl, and (when $A^2$ and $R^1$ are taken together) azetidine, aziridine, pyrrolidine, and piperidine.

Even more preferably, $A^2$ is selected from the group consisting of carboxymethyl, 2-carboxyethyl, 1-carboxyethyl, hydroxylaminocarbonylmethyl, hydroxymethyl, mercaptomethyl and imidazolylmethyl.

According to another preferred embodiment, $A^3$ is independently selected from the group consisting of amino acid side chains and corresponding protected derivatives; cycloalkyl; and alkyl optionally substituted with aryl, cycloalkyl, carboxy, hydroxylaminocarbonyl, alkoxy, aralkyloxy, mercapto, N-containing heterocycle, carboxy-alkylaminocarbonyl or amino-substituted acylamino.

More preferably, $A^3$ is independently selected from the group consisting of amino acid side chains and corresponding protected derivatives; cyclohexyl; and alkyl optionally substituted with phenyl, cyclohexyl, carboxy, hydroxylaminocarbonyl, methoxy, benzyloxy, mercapto, N-benzylimidazolyl, biotinyl, tetrazolyl, valinyl-N-carbonyl or 6-aminohexanoylamino.

According to another preferred embodiment, each $Y^3$ is independently selected from the group consisting of amino acids and corresponding protected derivatives.

According to another preferred embodiment, $Y^1$ is leucinyl ($R^1$=H, $R^2$=H, $A^1$=i-Bu); $Y^2$ is aspartyl ($R^1$=H, $R^2$=H, $A^2$=carboxymethyl); n=2; and $Y^3$ is valinylprolinyl ($R^1$=H, $R^2$=H, $A^3$=i-Pr)/($R^2$=H, $R^1$ with $A^3$=proline).

In another preferred embodiment, X is selected from the group consisting of alkoxy; aryloxy; aralkyloxy; hydroxyl; amino; mono- and dialkylamino optionally substituted with hydroxy, aminocarbonyl, N-alkylaminocarbonyl, carboxy or alkoxycarbonyl; dialkylamino; cycloalkylamino; cycloalky-lalkylamino; dicycloalkylamino; (alkyl)(aryl)amino; aralkylamino optionally substituted with carboxy; diaralkylamino; arylamino; N-containing heterocycle; bis-carboxylic acid-substituted alkylamine and (mono- or bis-carboxy) methylaminocarbonyl-substituted-N-containing heterocycle.

More preferably, X is selected from the group consisting of amino, methylamino, isopropylamino, isobutylamino, n-butylamino, t-butylamino, isoamylamino, isopentylamino, hexylamino, cyclohexylamino, cyclohexylmethylamino, methylphenylamino, phenylmethylamino, phenylamino, 4-methoxyphenylmethylamino, dimethylamino, diisopropylamino, diisobutylamino, hydroxy, methoxy, n-butoxy, t-butoxy, benzyloxy, 2-piperidinecarboxylic acid, N'-(α,α'-bis-carboxymethyl)-2-piperidinecarboxamide, N'-carboxymethyl-2-piperidinecarboxamide, 1-hydroxymethyl-2-methylpropylamino, 1-N'-methylamido-1-methylethylamino, 3,3-dimethylbutylamino, 1-N'-methylamidobutylamino, 1-amido-2-methylbutylamino, 1-carbomethoxy-2-methylbutylamino, 1-N'-methylamido-2-methylbutylamino, 1-carboxy-1-phenylmethylamino, morpholino, piperidinyl, N-phenylpiperazinyl, pipecolinyl, and piperazinyl.

According to another preferred embodiment, Z is selected from the group consisting of aliphatic acyl, aroyl, aralkylcarbonyl, heterocycloyl, alkoxycarbonyl, aralkyloxycarbonyl and heterocycloalkylcarbonyl. More preferably, Z is a (N-Ar'-urea)-para-substituted aralkylcarbonyl group and even more preferably, Z is a (N-Ar'-urea)-para-substituted phenylmethylcarbonyl group or (N-Ar'-urea)-para-substituted pyridylmethylcarbonyl group. Even more preferably, Z is a (N-ortho-substituted-Ar'urea)-para-substituted phenylmethylcarbonyl group or (N-meta-substituted-Ar'urea)-para-substituted phenylmethylcarbonyl group.

Examples of some specific preferred compounds of this invention are provided in Table 1.

TABLE 1

$Z-(Y^1)-(Y^2)-(Y^3)-X$   (I)
wherein
$Y^1$ is $-N(R^1)-C(R^2)$ $(A^1)-C(O)-$;
$Y^2$ is $-N(R^1)-C(R^2)$ $(A^2)-C(O)-$;
each $Y^3$ is represented by the formula
$-N(R^1)-C(R^2)$ $(A^3)-C(O)-$;
For $A^1$, $A^2$ and $A^3$, a single letter code refers to the side chain of the corresponding amino acid designated by that letter. A capital letter (e.q., A) indicates the L-amino acid while a small letter (e.g., a) indicates the D-amino acid. Both capital and small letters (e.g., L(l)) indicates a mixture.
Unless expressly noted to the contrary; compounds in this table have $R^1$ and $R^2$ as hydrogen.

| Cmpd # | Z | $A^1$ | $A^2$ | $(A^3)n$ | X |
|---|---|---|---|---|---|
| 1 | 3-methoxy-4-(N'-phenyl urea)phenylacetyl | L | D | V/P | OH |
| 2 | 3-methoxy-4-(N'-phenyl urea)phenylacetyl | M | D | V/P | OH |
| 3 | 6-methoxy-5-(N'-(2-methylphenyl)-urea)-2-pyridylacetyl | L | D | V | NH$_2$ |
| 4 | 6-methoxy-5-(N'-(2-methylphenyl)-urea)-2-pyridylacetyl | L | D | V | OH |
| 5 | 3-isoquinolinecarbonyl | L | E | V | OH |
| 6 | 3-isoquinolinecarbonyl | L | hydroxyl-aminocarb-onylmethyl | V | OH |
| 7 | 3-isoquinolinecarbonyl | L | S | V | OH |
| 8 | 3-isoquinolinecarbonyl | L | (N-Bn)-H | V | OH |
| 9 | 3-isoquinolinecarbonyl | L | C | V | OH |
| 10 | 3-isoquinolinecarbonyl | L | tetrazol-5-yl-methyl | V | OH |
| 11 | 3-isoquinolinecarbonyl | L | D | — | NH-CyM |
| 12 | 3-isoquinolinecarbonyl | L | D | — | OH |
| 13 | 3-(4-hydroxyphenyl)propionyl | L ($R^2$ = Me) | D | V | OMe |
| 14 | 3-(4-hydroxyphenyl)propionyl | L | D | — | NH-CyM |
| 15 | 3-(4-hydroxyphenyl)propionyl | L | d | — | NHi-Bu |
| 16 | 3-(4-hydroxyphenyl)propionyl | I | d | — | NHi-Bu |
| 17 | 3-(4-hydroxyphenyl)propionyl | I | D | — | NHi-Bu |
| 18 | 3-(4-hydroxyphenyl)propionyl | (N-Me)-L | D | V | OMe |
| 19 | 3-(4-hydroxyphenyl)propionyl | L | D | V | OMe |
| 20 | 3-(4-hydroxyphenyl)propionyl | L | D | (N-Me)-V | OMe |
| 21 | 3-(4-hydroxyphenyl)propionyl | L | 1-carboxy-ethyl | V | OMe |
| 22 | 3-(4-hydroxyphenyl)propionyl | L | (N-Me)-D | V | OMe |
| 23 | tetrahydro-3-isoquinolinecarbonyl | L | D | — | OH |
| 24 | 3-phenylpropionyl | L | D | — | NH-CyM |
| 25 | 4-phenylbutyryl | L | D | — | NH-CyM |
| 26 | 5-phenylpentanoyl | L | D | — | NH-CyM |
| 27 | tetrahydro-3-isoquinolinecarbonyl | L | (N-Bn)-H | V | OH |
| 28 | acetyl | (N-Bn)-L | D | V | OMe |
| 29 | acetyl | (N-phen-ethyl)-L | D | V | OMe |
| 30 | 3-phenylpropionyl | (N-phen-ethyl)-L | D | V | OMe |
| 31 | tetrahydro-3-isoquinolinecarbonyl | L | E | V | OH |
| 32 | 3-isoquinolinecarbonyl | L | D | V/P | OH |
| 33 | tetrahydro-3-isoquinolinecarbonyl | L | D | V/P | OH |

TABLE 1-continued $$Z-(Y^1)-(Y^2)-(Y^3)-X \quad (I)$$
wherein
$Y^1$ is $-N(R^1)-C(R^2)(A^1)-C(O)-$;
$Y^2$ is $-N(R^1)-C(R^2)(A^2)-C(O)-$;
each $Y^3$ is represented by the formula
$-N(R^1)-C(R^2)(A^3)-C(O)-$;
For $A^1$, $A^2$ and $A^3$, a single letter code
refers to the side chain of the corresponding amino acid
designated by that letter. A capital letter (e.q., A) indicates
the L-amino acid while a small letter (e.g., a) indicates
the D-amino acid. Both capital and small letters (e.g., L(l))
indicates a mixture.
Unless expressly noted to the contrary; compounds
in this table have $R^1$ and $R^2$ as hydrogen.

| Cmpd # | Z | $A^1$ | $A^2$ | $(A^3)n$ | X |
|---|---|---|---|---|---|
| 34 | phenylacetyl | L | D | V/P | OH |
| 35 | phenylacetyl | L | D | V/P | OMe |
| 36 | 3-phenylpropionyl | L | D | V/P | OH |
| 37 | 3-phenylpropionyl | L | D | V/P | OMe |
| 38 | 3-(4-hydroxyphenyl)propionyl | L | D | V/P | OH |
| 39 | 3-(4-hydroxyphenyl)propionyl | L | D | V/P | OMe |
| 40 | Boc | L | D | V/P | OMe |
| 41 | 2-quinolinecarbonyl | L | D | V/P | OMe |
| 42 | phenylacetyl | L | D | V/pipecolinyl | OH |
| 43 | phenylacetyl | L | D | V/n-butyl | OH |
| 44 | 2-quinolinecarbonyl | L | D | V/n-butyl | OH |
| 45 | 4-methoxyphenylacetyl | (N-Me)-L | D | V | NHMe |
| 46 | 3-(4-hydroxyphenyl)propionyl | (N-Me)-L | D | V | NHMe |
| 47 | benzylaminocarbonyl | L | D | V | NHMe |
| 48 | p-tolylaminocarbonyl | L | D | V | NHMe |
| 49 | phenylacetyl | n-propyl | D | V | NHMe |
| 50 | phenylacetyl | L | D | V | NHNaP |
| 51 | phenylacetyl | L | D | n-propyl | NHMe |
| 52 | 2-quinolinecarbonyl | L | D | n-propyl | NHMe |
| 53 | phenylacetyl | L | D | 2-butyl | $NH_2$ |
| 54 | phenylacetyl | L | D | 2-butyl | OMe |
| 55 | phenylacetyl | L | D | 2-butyl | NHMe |
| 56 | 2-quinolinecarbonyl | L | D | 2-butyl | OMe |
| 57 | 2-quinolinecarbonyl | L | D | 2-butyl | NHMe |
| 58 | 1,2,3,4-tetrahydro-2-quinolinecarbonyl | L | D | 2-butyl | NHMe |
| 59 | 2-quinolinecarbonyl | L | D | (O-Me)-T | NHMe |
| 60 | 2-quinolinecarbonyl | L | D | T | NHt-Bu |
| 61 | 2-quinolinecarbonyl | L | D | T | morpholino |
| 62 | Boc | L | D | T | NHt-Bu |
| 63 | 2-N-Boc-amino-1,2,3,4-tetrahydro-2-naphthoyl | L | D | V | OH |
| 64 | 3-phenylpropionyl | L | D | V | OH |
| 65 | 3-(4-hydroxyphenyl)-2-bis-(methylsulfonyl)aminopropionyl | L | D | V | OH |
| 66 | 3-(4-hydroxyphenyl)-2-N-Boc-aminopropionyl | L | D | V | OH |
| 67 | 2-amino-1,2,3,4-tetrahydro-2-naphthoyl TFA salt | L | D | V | OH |
| 68 | Boc | D | V | — | OH |
| 69 | 3-isoquinolinecarbonyl | L | D | V | OH |
| 70 | 3-isoquinolinecarbonyl | D | V | — | OH |
| 71 | 1,2,3,4-tetrahydro-3-isoquinolinecarbonyl | D | V | — | OH |
| 72 | naphthoyl | L | D | V | OH |
| 73 | 1,2,3,4-tetrahydro-2-naphthoyl | L | D | V | OH |
| 74 | naphthoyl | D | V | — | OH |
| 75 | 1,2,3,4-tetrahydro-2-naphthoyl | D | V | — | OH |
| 76 | 5-phenylpentanoyl | D | V | — | OH |
| 77 | 2-pyridinecarbonyl | L | D | V | OH |
| 78 | 2-pyridinecarbonyl | D | V | — | OH |
| 79 | 3-tetrahydrofurancarbonyl | L | D | V | OH |
| 80 | 2-tetrahydrofurancarbonyl | L | D | V | OH |
| 81 | 3-isoquinolinecarbonyl | F | D | V | OH |
| 82 | 3-isoquinolinecarbonyl | A ($R^2$ = Me) | D | V | OH |
| 83 | 3-isoquinolinecarbonyl | cyclohexyl | D | V | OH |
| 84 | 1,2,3,4-tetrahydro-3-isoquinolinecarbonyl | cyclohexyl | D | V | OH |

TABLE 1-continued

Z-(Y$^1$)—(Y$^2$)—(Y$^3$)—X  (I)
wherein
Y$^1$ is —N(R$^1$)—C(R$^2$) (A$^1$)-C(O)—;
Y$^2$ is —N(R$^1$)—C(R$^2$) (A$^2$)-C(O)—;
each Y$^3$ is represented by the formula
—N(R$^1$)—C(R$^2$) (A$^3$)-C(O)—;
For A$^1$, A$^2$ and A$^3$, a single letter code
refers to the side chain of the corresponding amino acid
designated by that letter. A capital letter (e.q., A) indicates
the L-amino acid while a small letter (e.g., a) indicates
the D-amino acid. Both capital and small letters (e.g., L(l))
indicates a mixture.
Unless expressly noted to the contrary; compounds
in this table have R$^1$ and R$^2$ as hydrogen.

| Cmpd # | Z | A$^1$ | A$^2$ | (A$^3$)n | X |
|---|---|---|---|---|---|
| 85 | 3-isoquinolinecarbonyl | cyclohexyl-methyl | D | V | OH |
| 86 | 1,2,3,4-tetrahydro-3-isoquinolinecarbonyl | cyclohexyl-methyl | D | V | OH |
| 87 | 3-isoquinolinecarbonyl | D | F | — | OH |
| 88 | 1,2,3,4-tetrahydro-3-isoquinolinecarbonyl | D | L | — | OH |
| 89 | 3-isoquinolinecarbonyl | D | L | — | OH |
| 90 | 1,2,3,4-tetrahydro-3-isoquinolinecarbonyl | L | D | L | OH |
| 91 | 3-isoquinolinecarbonyl | L | D | L | OH |
| 92 | 1,2,3,4-tetrahydro-3-isoquinolinecarbonyl | L | D | F | OH |
| 93 | 3-isoquinolinecarbonyl | L | D | F | OH |
| 94 | 2-quinolinecarbonyl | L | D | V | OH |
| 95 | 3,3-diphenylpropionyl | L | D | V | OH |
| 96 | 1,2,3,4-tetrahydro-3-isoquinolinecarbonyl | A | D | V | OH |
| 97 | 3-isoquinolinecarbonyl | A | D | V | OH |
| 98 | 5-phenylpentanoyl | L | D | V | OH |
| 99 | indole-2-carbonyl | L | D | V | OH |
| 100 | 3-(4-hydroxy)phenylpropionyl | L | D | — | NHi-Bu |
| 101 | benzoyl | L | D | — | NHi-Bu |
| 102 | 5-phenylpentanoyl | L | D | — | NHi-amyl |
| 103 | 3-(4-hydroxy)phenylpropionyl | L | D | — | NHi-amyl |
| 104 | 6-phenylhexanoyl | L | D | V | OH |
| 105 | benzoyl | L | D | V | OH |
| 106 | 5-phenylpentanoyl | L | D | — | NHi-Bu |
| 107 | N-phenylsuccinamoyl | L | D | V | OH |
| 108 | N-4-fluorophenylsuccinamoyl | L | D | V | OH |
| 109 | N-methyl-N-phenylsuccinamoyl | L | D | V | OH |
| 110 | 1,2,3,4-tetrahydro-2-quinolinecarbonyl | L | D | — | NHi-amyl |
| 111 | N-phenylsuccinamoyl | L | D | — | NHi-Bu |
| 112 | 3-phenylpropyl | (N-Me)-L | (O-Me)-D | V | OMe |
| 113 | benzoyl | (N-Me)-L | D | V | OH |
| 114 | 1,2,3,4-tetrahydro-2-quinolinecarbonyl | L | D | V | NHHex |
| 115 | 1,2,3,4-tetrahydro-2-quinolinecarbonyl | L | D | V | 4-phenyl-piperidine |
| 116 | 3-(4-hydroxy)phenylpropionyl | L | D | — | NHHex |
| 117 | 3-(4-hydroxy)phenylpropionyl | L | D | — | N(iBu)$_2$ |
| 118 | 3-(4-hydroxy)phenylpropionyl | L | D | — | N(iBu)$_2$ |
| 119 | 3-(4-hydroxy)phenylpropionyl | L | D | V | NHHex |
| 120 | 1,2,3,4-tetrahydro-2-quinolinecarbonyl | L | D | V | NMePh |
| 121 | 2-quinolinecarbonyl | L | D | V | NMePh |
| 122 | 1,2,3,4-tetrahydro-2-quinolinecarbonyl | L | D | V | NH-4-fluoro-phenyl |
| 123 | 2-quinolinecarbonyl | L | D | V | NH-4-fluoro-phenyl |
| 124 | 1,2,3,4-tetrahydro-2-quinolinecarbonyl | L | D | V | NHPh |
| 125 | 2-quinolinecarbonyl | L | D | V | NHPh |
| 126 | 2-pyridinecarbonyl | (N-Me)-L | D | V | NHMe |
| 127 | 2-quinolinecarbonyl | L | D | V | 4-phenyl-piper-azinyl |
| 128 | 4-methoxybenzoyl | (N-Me)-L | D | V | NHMe |
| 129 | phenylacetyl | Y | D | V | NHMe |
| 130 | phenylacetyl | P | D | V | NHMe |

TABLE 1-continued

Z-(Y$^1$)—(Y$^2$)—(Y$^3$)—X    (I)
wherein
Y$^1$ is —N(R$^1$)—C(R$^2$) (A$^1$)-C(O)—;
Y$^2$ is —N(R$^1$)—C(R$^2$) (A$^2$)-C(O)—;
each Y$^3$ is represented by the formula
—N(R$^1$)—C(R$^2$) (A$^3$)-C(O)—;
For A$^1$, A$^2$ and A$^3$, a single letter code
refers to the side chain of the corresponding amino acid
designated by that letter. A capital letter (e.q., A) indicates
the L-amino acid while a small letter (e.g., a) indicates
the D-amino acid. Both capital and small letters (e.g., L(l))
indicates a mixture.
Unless expressly noted to the contrary; compounds
in this table have R$^1$ and R$^2$ as hydrogen.

| Cmpd # | Z | A$^1$ | A$^2$ | (A$^3$)n | X |
|---|---|---|---|---|---|
| 131 | phenylecetyl | R | D | V | NHMe |
| 132 | phenylacetyl | N | D | V | NHMe |
| 133 | 2-N-Boc-amino-1,2,3,4-tetrahydro-2-naphthoyl | D | V | — | NHMe |
| 134 | 2-N-phenylacetylamino-1,2,3,4-tetrahydro-2-naphthoyl | D | V | — | NHMe |
| 135 | Boc | D | P | G | OH |
| 136 | phenylacetyl | D | P | G | OH |
| 137 | phenylacetyl | L | D | — | N-[bis-(carboxy)-methyl]-pipecolin-amido |
| 138 | phenylacetyl | L | D | P | NH-[bis-(carboxy)-methyl] |
| 139 | phenylacetyl | L | D | — | N-[carboxy-methyl]-pipecolin-amide |
| 140 | 3-phenylpropionyl | (N-Me)-L | D | V | OMe |
| 141 | 4-hydroxyphenylacetyl | (N-Me)-L | D | V | OMe |
| 142 | 2-quinolinecarbonyl | (N-Me)-L | D | V | OMe |
| 143 | 4-phenylbutyryl | (N-Me)-L | D | V | OMe |
| 144 | 4-(N'-2-hydroxy-phenylurea)phenylacetyl | L | D | V/P | OH |
| 145 | PUPA | L | D | V/P | OH |
| 146 | 4-(N'-2-hydroxy-phenylurea)phenylacetyl | M | D | V/P | OH |
| 147 | 3-methoxy-4-N'-phenylurea)phenylacetyl | L | D | V/P | NH$_2$ |
| 148 | 2-MPUPA | L | D | V/P | NH$_2$ |
| 149 | Boc | D | V | P | OH |
| 150 | 5-phenylpentanoyl | D | V | P | OH |
| 151 | 2-allyl-4-phenylbutyryl | V | P | — | OH |
| 152 | acetyl | F | L | D/V | OH |
| 153 | benzoyl | F | L | D/V | OH |
| 154 | 1,2,3,4-tetrahydro-3-isoquinolinecarbonyl | L | D | V | OMe |
| 155 | 4-phenylbutyryl | L | D | V | OH |
| 156 | 3-isoquinolinecarbonyl | L | D | V | OMe |
| 157 | 3-isoquinolinecarbonyl | L | D | — | NHi-Bu |
| 158 | 2-quinolinecarbonyl | L | D | V | Ot-Bu |
| 159 | 2-quinolinecarbonyl | L | (O-Bn)-D | V | OH |
| 160 | 2-quinolinecarbonyl | L | D | D | OH |
| 161 | 4-phenylbutyryl | L | D | — | NHi-Bu |
| 162 | 3-phenylpropionyl | L | D | — | NHi-B |
| 163 | benzoyl | G | L | D | NHi-Bu |
| 164 | 2-quinolinecarbonyl | L | D | V | NHMe |
| 165 | 4-methoxybenzoyl | L | D | — | NHi-Bu |
| 166 | 4-phenylbutylyl | L | D | V | OMe |
| 167 | Boc | L | D | V/M | OMe |
| 168 | 2-quinolinecarbonyl | L | D | V/M | OMe |
| 169 | N-n-butylaminocarbonyl | D | V | — | OMe |
| 170 | 2-quinolinecarbonyl | L | D | T | OMe |
| 171 | N-t-butylaminocarbonyl | L | D | — | NHi-Bu |
| 172 | benzoyl | G | D | V | OMe |
| 173 | benzoyl | G | (O-Me)-D | V | OMe |
| 174 | 2-quinolinecarbonyl | L | D | — | NH(1-hydroxy- |

TABLE 1-continued

Z-(Y¹)—(Y²)—(Y³)—X   (I)
wherein
Y¹ is —N(R¹)—C(R²) (A¹)-C(O)—;
Y² is —N(R¹)—C(R²) (A²)-C(O)—;
each Y³ is represented by the formula
—N(R¹)—C(R²) (A³)-C(O)—;
For A¹, A² and A³, a single letter code
refers to the side chain of the corresponding amino acid
designated by that letter. A capital letter (e.q., A) indicates
the L-amino acid while a small letter (e.g., a) indicates
the D-amino acid. Both capital and small letters (e.g., L(l))
indicates a mixture.
Unless expressly noted to the contrary; compounds
in this table have R¹ and R² as hydrogen.

| Cmpd # | Z | A¹ | A² | (A³)n | X |
|---|---|---|---|---|---|
| 175 | 2-quinolinecarbonyl | L | D | V | methyl-2-methyl-propyl) morpholino |
| 176 | 4-methoxyphenylacetyl | L | D | T | OMe |
| 177 | 4-methoxyphenylsulfonyl | L | D | T | OMe |
| 178 | 2-quinolinecarbonyl | L | D | V | NH₂ |
| 179 | 2-quinolinecarbonyl | (N-Me)-L | D | V | NHMe |
| 180 | phenylacetyl | (N-Me)-L | D | V | NHMe |
| 181 | phenylacetyl | L | D | V | NHMe |
| 182 | 3-phenylpropionyl | (N-Me)-L | D | V | NHMe |
| 183 | phenylacetyl | M | D | V | NHMe |
| 184 | 3-phenylpropionyl | (N-Me)-L | D | V | NHMe |
| 185 | 2-quinolinecarbonyl | L | D | A (R² = Me) | NHMe |
| 186 | 2-quinolinecarbonyl | L | D | V/M | OH |
| 187 | phenylaminocarbonyl | L | D | V | NHMe |
| 188 | 4-hydroxyphenylacetyl | (N-Me)-L | D | V | NHMe |
| 189 | phenylsulfonyl | L | D | V | NHMe |
| 190 | phenylacetyl | L | D | (O-Me)-T | OMe |
| 191 | phenylacetyl | L | D | T | OMe |
| 192 | phenylacetyl | L | D | (O-Bn)-T | OMe |
| 193 | phenylacetyl | L | D | (O-Ac)-T | OMe |
| 194 | phenylacetyl | V | D | V | NHMe |
| 195 | 2-quinolinecarbonyl | L | D | T | On-Bu |
| 196 | phenylacetyl | L | D | V | On-Bu |
| 197 | 2-quinolinecarbonyl | L | D | T | NH(4-methoxy-benzyl) |
| 198 | 2-quinolinecarbonyl | L | D | — | NH(3,3-dimethyl-n-butyl) |
| 199 | PUPA | l | D | V/P | NH₂ |
| 200 | PUPA | L | d | V/P | NH₂ |
| 201 | PUPA | L | D | V/P | NH₂ |
| 202 | 2-MPUPA | (N-6-amino-hexanoyl)-K | D | V/P | OH |
| 203 | PUPA | L | D | V | OH |
| 204 | PUPA | L | D | V | NHMe |
| 205 | PUPA | L | D | V | NHi-Bu |
| 206 | 2-MPUPA | L | D | V/P | OH |
| 207 | 2-MPUPA | L | D | phenyl | OH |
| 208 | PUPA | L | D | V/P | NH₂ |
| 209 | PUPA | l | D | V/P | NH₂ |
| 210 | PUPA | L | d | V/P | NH₂ |
| 211 | PUPA | L | D | v/P | NH₂ |
| 212 | PUPA | l | d | v/p | NH₂ |
| 213 | PUPA | L | D | — | NHBn |
| 214 | PUPA | L | D | — | morpholino |
| 215 | PUPA | L | D | — | NHi-Pr |
| 216 | PUPA | L | D | — | NHCy |
| 217 | PUPA | L | D | — | NHi-Bu |
| 218 | PUPA | L | D | — | piperidinyl |
| 219 | 2-MPUPA | M | D | D | NH₂ |
| 220 | 2-MPUPA | M | D | L | NH₂ |
| 221 | 2-MPUPA | M | D | V | NH₂ |
| 222 | 2-MPUPA | M | D | l | NH₂ |
| 223 | 2-MPUPA | M | D | E | NH₂ |

TABLE 1-continued

Z-(Y$^1$)—(Y$^2$)—(Y$^3$)—X  (I)
wherein
Y$^1$ is —N(R$^1$)—C(R$^2$) (A$^1$)-C(O)—;
Y$^2$ is —N(R$^1$)—C(R$^2$) (A$^2$)-C(O)—;
each Y$^3$ is represented by the formula
—N(R$^1$)—C(R$^2$) (A$^3$)-C(O)—;
For A$^1$, A$^2$ and A$^3$, a single letter code
refers to the side chain of the corresponding amino acid
designated by that letter. A capital letter (e.q., A) indicates
the L-amino acid while a small letter (e.g., a) indicates
the D-amino acid. Both capital and small letters (e.g., L(l))
indicates a mixture.
Unless expressly noted to the contrary; compounds
in this table have R$^1$ and R$^2$ as hydrogen.

| Cmpd # | Z | A$^1$ | A$^2$ | (A$^3$)n | X |
|---|---|---|---|---|---|
| 224 | 2-MPUPA | M | D | T | NH$_2$ |
| 225 | 2-MPUPA | M | D | M | NH$_2$ |
| 226 | 2-MPUPA | M | D | n | NH$_2$ |
| 227 | 2-MPUPA | M | D | e | NH$_2$ |
| 228 | 2-MPUPA | M | D | W | NH$_2$ |
| 229 | 2-MPUPA | M | D | s | NH$_2$ |
| 230 | 2-MPUPA | L | D | D | NH$_2$ |
| 231 | 2-MPUPA | L | D | L | NH$_2$ |
| 232 | 2-MPUPA | L | D | V | NH$_2$ |
| 233 | 2-MPUPA | L | D | l | NH$_2$ |
| 234 | 2-MPUPA | L | D | E | NH$_2$ |
| 235 | 2-MPUPA | L | D | T | NH$_2$ |
| 236 | 2-MPUPA | L | D | M | NH$_2$ |
| 237 | 2-MPUPA | L | D | n | NH$_2$ |
| 238 | 2-MPUPA | L | D | e | NH$_2$ |
| 239 | 2-MPUPA | L | D | W | NH$_2$ |
| 240 | 2-MPUPA | L | D | s | NH$_2$ |
| 241 | 2-MPUPA | P | D | D | NH$_2$ |
| 242 | 2-MPUPA | P | D | L | NH$_2$ |
| 243 | 2-MPUPA | P | D | V | NH$_2$ |
| 244 | 2-MPUPA | P | D | l | NH$_2$ |
| 245 | 2-MPUPA | P | D | E | NH$_2$ |
| 246 | 2-MPUPA | P | D | T | NH$_2$ |
| 247 | 2-MPUPA | P | D | M | NH$_2$ |
| 248 | 2-MPUPA | P | D | n | NH$_2$ |
| 249 | 2-MPUPA | P | D | e | NH$_2$ |
| 250 | 2-MPUPA | P | D | W | NH$_2$ |
| 251 | 2-MPUPA | P | D | s | NH$_2$ |
| 252 | 2-MPUPA | T | D | D | NH$_2$ |
| 253 | 2-MPUPA | T | D | L | NH$_2$ |
| 254 | 2-MPUPA | T | D | V | NH$_2$ |
| 255 | 2-MPUPA | T | D | l | NH$_2$ |
| 256 | 2-MPUPA | T | D | E | NH$_2$ |
| 257 | 2-MPUPA | T | D | T | NH$_2$ |
| 258 | 2-MPUPA | T | D | M | NH$_2$ |
| 259 | 2-MPUPA | T | D | n | NH$_2$ |
| 260 | 2-MPUPA | T | D | e | NH$_2$ |
| 261 | 2-MPUPA | T | D | W | NH |
| 262 | 2-MPUPA | T | D | s | NH$_2$ |
| 263 | 2-MPUPA | E | D | D | NH$_2$ |
| 264 | 2-MPUPA | E | D | L | NH$_2$ |
| 265 | 2-MPUPA | E | D | V | NH$_2$ |
| 266 | 2-MPUPA | E | D | l | NH$_2$ |
| 267 | 2-MPUPA | E | D | E | NH$_2$ |
| 268 | 2-MPUPA | E | D | T | NH$_2$ |
| 269 | 2-MPUPA | E | D | M | NH$_2$ |
| 270 | 2-MPUPA | E | D | n | NH$_2$ |
| 271 | 2-MPUPA | E | D | e | NH$_2$ |
| 272 | 2-MPUPA | E | D | W | NH$_2$ |
| 273 | 2-MPUPA | E | D | s | NH$_2$ |
| 274 | 2-MPUPA | C | D | V | NH$_2$ |
| 275 | 2-MPUPA | S | D | D | NH$_2$ |
| 276 | 2-MPUPA | S | D | L | NH$_2$ |
| 277 | 2-MPUPA | S | D | V | NH$_2$ |
| 278 | 2-MPUPA | S | D | l | NH$_2$ |
| 279 | 2-MPUPA | S | D | E | NH$_2$ |
| 280 | 2-MPUPA | S | D | T | NH$_2$ |
| 281 | 2-MPUPA | S | D | M | NH$_2$ |
| 282 | 2-MPUPA | S | D | n | NH$_2$ |
| 283 | 2-MPUPA | S | D | e | NH$_2$ |
| 284 | 2-MPUPA | S | D | W | NH$_2$ |

TABLE 1-continued $$Z-(Y^1)-(Y^2)-(Y^3)-X \quad (I)$$
wherein
$Y^1$ is $-N(R^1)-C(R^2)(A^1)-C(O)-$;
$Y^2$ is $-N(R^1)-C(R^2)(A^2)-C(O)-$;
each $Y^3$ is represented by the formula
$-N(R^1)-C(R^2)(A^3)-C(O)-$;
For $A^1$, $A^2$ and $A^3$, a single letter code
refers to the side chain of the corresponding amino acid
designated by that letter. A capital letter (e.q., A) indicates
the L-amino acid while a small letter (e.g., a) indicates
the D-amino acid. Both capital and small letters (e.g., L(l))
indicates a mixture.
Unless expressly noted to the contrary; compounds
in this table have $R^1$ and $R^2$ as hydrogen.

| Cmpd # | Z | $A^1$ | $A^2$ | $(A^3)n$ | X |
|---|---|---|---|---|---|
| 285 | 2-MPUPA | S | D | s | NH$_2$ |
| 286 | 2-MPUPA | l | D | D | NH$_2$ |
| 287 | 2-MPUPA | l | D | L | NH$_2$ |
| 288 | 2-MPUPA | l | D | V | NH$_2$ |
| 289 | 2-MPUPA | l | D | l | NH$_2$ |
| 290 | 2-MPUPA | l | D | E | NH$_2$ |
| 291 | 2-MPUPA | l | D | T | NH$_2$ |
| 292 | 2-MPUPA | l | D | M | NH$_2$ |
| 293 | 2-MPUPA | l | D | n | NH$_2$ |
| 294 | 2-MPUPA | l | D | e | NH$_2$ |
| 295 | 2-MPUPA | l | D | W | NH$_2$ |
| 296 | 2-MPUPA | l | D | s | NH$_2$ |
| 297 | 2-MPUPA | Q | D | D | NH$_2$ |
| 298 | 2-MPUPA | Q | D | L | NH$_2$ |
| 299 | 2-MPUPA | Q | D | V | NH$_2$ |
| 300 | 2-MPUPA | Q | D | l | NH$_2$ |
| 301 | 2-MPUPA | Q | D | E | NH$_2$ |
| 302 | 2-MPUPA | Q | D | T | NH$_2$ |
| 303 | 2-MPUPA | Q | D | M | NH$_2$ |
| 304 | 2-MPUPA | Q | D | n | NH$_2$ |
| 305 | 2-MPUPA | Q | D | e | NH$_2$ |
| 306 | 2-MPUPA | Q | D | W | NH$_2$ |
| 307 | 2-MPUPA | Q | D | s | NH$_2$ |
| 308 | 2-MPUPA | M | E | D | NH$_2$ |
| 309 | 2-MPUPA | M | E | V | NH$_2$ |
| 310 | 2-MPUPA | L | E | D | NH$_2$ |
| 311 | 2-MPUPA | L | E | V | NH$_2$ |
| 312 | 2-MPUPA | P | E | D | NH$_2$ |
| 313 | 2-MPUPA | P | E | V | NH$_2$ |
| 314 | 2-MPUPA | T | E | D | NH$_2$ |
| 315 | 2-MPUPA | M | D | V/P | OH |
| 316 | 4-(N'-2-pyridylurea)phenylacetyl | L | D | V/P | OH |
| 317 | 3-methoxy-4-(N'-2-methylphenyl)-urea)phenylacetyl | L | D | V/P | NH$_2$ |
| 318 | PUPA | L | D | V | morpholino |
| 319 | PUPA | L | D | V | NHi-Pr |
| 320 | PUPA | L | D | V | NHCy |
| 321 | PUPA | L | D | V | NHBn |
| 322 | PUPA | L | D | V | piperidinyl |
| 323 | PUPA | L | D | V | NHi-Bu |
| 324 | PUPA | L | D | V/P | NHCy |
| 325 | PUPA | L | D | V/P | piperidinyl |
| 326 | PUPA | L | D | V/P | NHBn |
| 327 | PUPA | L | D | V/P | NHi-Pr |
| 328 | PUPA | L | D | V/P | NHi-Bu |
| 329 | 2-MPUPA | L | D | V | morpholino |
| 330 | 3-(4-hydroxyphenyl) | pipecolyl | D | — | NHi-Bu |
| 331 | 3-(4-hydroxyphenyl)-propionyl | P | D | — | NHi-Bu |
| 332 | 3-isoquinolinecarbonyl | L | (N-3-methyl-2-butyroyl)-N | — | OH |
| 333 | 4-methylpentanoyl | D | — | — | NHCyM |
| 334 | Cbz | —CH$_2$CH$_2$— (N of $A^2$) | (N—CH$_2$CH$_2$— (C of $A^1$)-D | V | OMe |
| 335 | 3-(4-hydroxyphenyl)propionyl | —CH$_2$CH$_2$— (N of $A^2$) | (N—CH$_2$CH$_2$— (C of $A^1$)-D | V | OMe |

TABLE 1-continued

Z-(Y$^1$)—(Y$^2$)—(Y$^3$)—X   (I)
wherein
Y$^1$ is —N(R$^1$)—C(R$^2$) (A$^1$)-C(O)—;
Y$^2$ is —N(R$^1$)—C(R$^2$) (A$^2$)-C(O)—;
each Y$^3$ is represented by the formula
—N(R$^1$)—C(R$^2$) (A$^3$)-C(O)—;
For A$^1$, A$^2$ and A$^3$, a single letter code
refers to the side chain of the corresponding amino acid
designated by that letter. A capital letter (e.q., A) indicates
the L-amino acid while a small letter (e.g., a) indicates
the D-amino acid. Both capital and small letters (e.g., L(l))
indicates a mixture.
Unless expressly noted to the contrary; compounds
in this table have R$^1$ and R$^2$ as hydrogen.

| Cmpd # | Z | A$^1$ | A$^2$ | (A$^3$)n | X |
|---|---|---|---|---|---|
| 336 | 4-(2-fluorophenyl-urea)phenylacetyl | L | D | V/P | OH |
| 337 | 2-MPUPA | L | D | V/P/S | OH |
| 338 | 2-MPUPA | L | D | V/P/S/T | OH |
| 339 | 2-MPUPA | V | L | P/D | OH |
| 340 | 2-MPUPA | v | I | p/d | OH |
| 341 | 2-MPUPA | L | P | V/D | OH |
| 342 | 2-MPUPA | P | D | — | OH |
| 343 | hydrogen | p | v | d/I | 2-MPUBA |
| 344 | hydrogen | v | d | I | 2-MPUBA |
| 345 | 2-MPUPA | L | D | I | OH |
| 346 | 4-(N-(6-methyl-2-pyridyl)urea)phenylacetyl | L | D | V/P | OH |
| 347 | 4-(N-2-fluorophenyl-urea)phenylacetyl | L | D | V/P | OH |
| 348 | 4-phenylbutyroyl | (N-Me)-L | D | V | NHMe |
| 349 | phenylacetyl | S | D | V | NHMe |
| 350 | phenylacetyl | K | D | V | NHMe |
| 351 | phenylacetyl | L | D | A (R$^2$ = Me) | NHMe |
| 352 | phenylacetyl | L | D | (O-Bn)-S | NHMe |
| 353 | 2-quinolinecarbonyl | L | D | (O-Bn)-S | NHMe |
| 354 | Boc | L | D | T | NHBu |
| 355 | Boc | L | D | V/P | OH |
| 356 | 2-quinolinecarbonyl | L | D | V/P | OH |
| 357 | 4-(N'-2-pyridylurea)phenylacetyl | L | D | V/P | NH$_2$ |
| 358 | 2-MPUPA | L | D*THAM | V/P | OTHAM |
| 359 | 2-MPUPA | L | D*Na | V/P | ONa |
| 360 | 2-MPUPA | L(l) | Het$^1$ | — | — |
| 361 | 2-MPUPA | I | Het$^1$ | — | — |
| 362 | 2-MPUPA | L(l) | Het$^2$ | — | — |
| 363 | 2-MPUPA | L(l) | Het$^3$ | — | — |
| 364 | 2-MPUPA | L(l) | Het$^4$ | — | — |
| 365 | 2-MPUPA | L(l) | Het$^5$ | — | — |
| 366 | 9-fluorenylmethoxycarbonyl | L | D | V | OH |
| 367 | 3-methoxyphenylacetyl | L | D | V | OH |
| 368 | 3-(3-methylindolyl)propionyl | L | D | V | OH |
| 369 | 2-phenyl-3-methyl-pyrazol-4-ylcarbonyl | L | D | V | OH |
| 370 | 6-methylbenzpyrimidon-2-ylcarbonyl | L | D | V | OH |
| 371 | 4-oxo-4,5,6,7-tetrahydrobenzo-[b]furan-3-ylcarbonyl | L | D | V | OH |
| 372 | 3-(5-(phenylacetylenyl)pyri-dinecarbonyl | L | D | V | OH |
| 373 | 3-(2-phenylthio)-pyridinecarbonyl | L | D | V | OH |
| 374 | 4-propylbenzoyl | L | D | V | OH |
| 375 | 4-(2-(3-pyridiyl))thiazolecarbonyl | L | D | V | OH |
| 376 | 4-(2-(4-pyridinyl)thiazolecarbonyl | L | D | V | OH |
| 377 | 5-(2-(3-pyridinyl))thio-phenesulfonyl | L | D | V | OH |
| 378 | 5-(2-(1-pyrrolyl))pyridinecarbonyl | L | D | V | OH |
| 379 | N,N-(4-trifloromethylpyridin-2-yl)methylhydraziocarbonyl | L | D | V | OH |
| 380 | 2-quinoxalinylaminocarbonyl | L | D | V | OH |
| 381 | N-(4-trifluoromethylpyridin-2-yl)piperazinocarbonyl | L | D | V | OH |
| 382 | S-(2-(2-trifluoromethyl)-phenylsulfonyl)-tetrahydrothiophenesulfonyl | L | D | V | OH |
| 383 | 1-(4-chlorophenylmethyl)pyr- | L | D | V | OH |

TABLE 1-continued

Z-(Y$^1$)—(Y$^2$)—(Y$^3$)—X  (I)
wherein
Y$^1$ is —N(R$^1$)—C(R$^2$) (A$^1$)-C(O)—;
Y$^2$ is —N(R$^1$)—C(R$^2$) (A$^2$)-C(O)—;
each Y$^3$ is represented by the formula
—N(R$^1$)—C(R$^2$) (A$^3$)-C(O)—;
For A$^1$, A$^2$ and A$^3$, a single letter code
refers to the side chain of the corresponding amino acid
designated by that letter. A capital letter (e.q., A) indicates
the L-amino acid while a small letter (e.g., a) indicates
the D-amino acid. Both capital and small letters (e.g., L(l))
indicates a mixture.
Unless expressly noted to the contrary; compounds
in this table have R$^1$ and R$^2$ as hydrogen.

| Cmpd # | Z | A$^1$ | A$^2$ | (A$^3$)n | X |
|---|---|---|---|---|---|
|  | rolidin-2-on-4-yl-carbonyl |  |  |  |  |
| 384 | 1-(2-furanylmethy)lpyr-rolidin-2-on-4-ylcarbonyl | L | D | V | OH |
| 385 | 2(1-pyrrolyl)benzoyl | L | D | V | OH |
| 386 | 6-chlorochroman-3-ylcarbonyl | L | D | V | OH |
| 387 | 2,3-dihydrobenzofuran-5-ylcarbonyl | L | D | V | OH |
| 388 | 4,6-dimethylpyrazolo[1,5-c]triazin-3-ylcarbonyl | L | D | V | OH |
| 389 | 3,4-benzocyclohexanoyl | L | D | V | OH |
| 390 | norbonylacetyl | L | D | V | OH |
| 391 | 1,2,3,4-tetrahyro-9-acridinylcarbonyl | L | D | V | OH |
| 392 | 5,6,7,8-tetrahydronaphthyl-aminocarbonyl | L | D | V | OH |
| 393 | 3-(2-(4-methylthiophenoxy))-pyridinecarbonyl | L | D | V | OH |
| 394 | 2-(6-methoxynaphth-2-yl)propionyl | L | D | V | OH |
| 395 | (2-naphthyloxy)acetyl | L | D | V | OH |
| 396 | 3-quinuclidinylaminocarbonyl | L | D | V | OH |
| 397 | 2-(1,2,3,4-tetra-hydroisoquinoline)carbonyl | L | D | V | OH |
| 398 | adamantan-2-ylcarbonyl | L | D | V | OH |
| 399 | (2-pyridyl)acetyl | L | D | V | OH |
| 400 | 6-methylcyclohexen-2-ylcarbonyl | L | D | V | OH |
| 401 | (3-quinolinyl)acetyl | L | D | V | OH |
| 402 | 4-(2-butyl)phenylaminocarbonyl | L | D | V | OH |
| 403 | 1,4-dihydro-1-ethyl-7-methyl-4-oxo-1,8-naphthyrdin-3-ylcarbonyl | L | D | V | OH |
| 404 | (2-thienyl)acetyl | L | D | V | OH |
| 405 | 4-(2-propyl)benzoyl | L | D | V | OH |
| 406 | 3,4-methylenedoxybenzoyl | L | D | V | OH |
| 407 | 2-(5-(2-pyridyl))thiophenecarbonyl | L | D | V | OH |
| 408 | N-iminodibenzylcarbonyl | L | D | V | OH |
| 409 | 2-MPUPA | P | D | 1 | NHMe |
| 410 | 2-MPUPA | P | D | 1 | OMe |
| 411 | 2-MPUPA | P | D | 1 | OH |
| 412 | 2-MPUPA | —CH$_2$CH$_2$— (N of R$^1$) | D | 1 | OH |
| 413 | 2-MPUPA | P | E | — | NMe |
| 414 | 2-MPUPA | P | E | 1 | NMe |
| 415 | 2-MPUPA | P | E | 1 | OH |
| 416 | 2-MPUPA | P | E | — | OH | where Het$^1$, Het$^2$, Het$^3$, Het$^4$, and Het$^5$ in Table 1 are defined below:

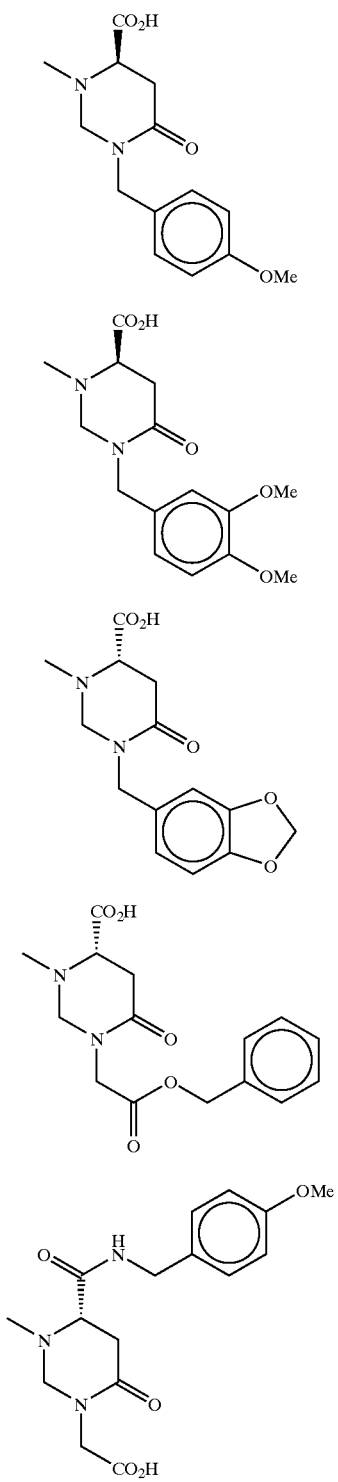

The more preferred compounds of formula (I) are selected from the group consisting of compound numbers 1, 2, 4, 144, 145, 146, 147, 148, 206, 315, 316, 317, 337, 338, 345, 346, 347, 357, 358 and 359 as identified in Table 1. Even more preferred compounds of formula (I) are selected from the group consisting of compound numbers 1, 206, 316, 358 and 359 as identified in Table 1. The most preferred compounds of formula (I) are selected from the group consisting of compound numbers 358 and 359 as identified in Table 1.

Other compounds of this invention are compounds of formula II:

$$K-(Y^1)-(Y^2)-(Y^3)_n-J \qquad (II)$$

and pharmaceutically acceptable derivatives thereof, wherein;

K is selected from the group consisting of hydrogen, alkyl, aliphatic acyl, aroyl, aralkylcarbonyl, heterocycloyl, sulfonyl, aralkylcarbonyl, heterocycloalkylcarbonyl, alkoxycarbonyl, aralkyloxycarbonyl, heterocycloalkoxycarbonyl, alkylaminocarbonyl and aralkylaminocarbonyl;

J is selected from the group consisting of alkoxy; aryloxy; aralkyloxy; hydroxyl; amino; alkylamino optionally substituted with hydroxy, aminocarbonyl, N-alkylaminocarbonyl, carboxy or alkoxycarbonyl; dialkylamino; cycloalkylamino; dicycloalkylamino; (alkyl)(aryl)amino; aralkylamino optionally substituted with carboxy; diaralkylamino; arylamino; and (mono- or bis-carboxylic acid)-substituted alkylamine; and each Y, $Y^2$, $Y^3$, $R^1$, $A^1$, $A^2$, $A^3$, $R^2$, and n is independently as defined in formula I above.

Compounds of this invention may be synthesized using any conventional technique. Preferably, these compounds are chemically synthesized from readily available starting materials, such as α-amino acids and their functional equivalents. Modular and convergent methods for the synthesis of these compounds are also preferred. In a convergent approach, for example, large sections of the final product are brought together in the last stages of the synthesis, rather than by incremental addition of small pieces to a growing molecular chain.

According to one embodiment, compounds of the present invention may be synthesized in the following manner. A protected amino acid or functional equivalent is coupled to an appropriate activated ester moiety. The coupled product, if suitably functionalized, may be further reacted with yet another activated ester moiety. This material can be further manipulated to give the desired compounds of the invention. At each step of the above sequence, the ester can be hydrolyzed to the corresponding acid to give another compound of the invention. This acid may also be converted to a corresponding acid derivative by standard methods.

Alternatively, the activated ester moieties mentioned above can be attached together first, then the resulting compound can be attached to additional amino acids or their functional group equivalents. At this point the final manipulations and/or necessary deprotection steps can be performed.

In another embodiment, under suitable conditions the desired functionalities can be incorporated (protected or unprotected) in one of the activated ester moieties. That ester is then coupled with an amino acid derivative or a moiety consisting of an amino acid derivative previously coupled to an activated ester. The resulting product can then be subjected to any deprotection steps, If necessary, to give compounds of the invention.

Alternatively, the compounds of this invention may be synthesized using solid support techniques. The core amino acid or their functional equivalent groups are assembled using standard reiterative coupling methodology on a resin. When the desired core is complete, the resulting fragment can be coupled with an activated ester moiety and/or the tethered end of the fragment may be further derivatized to give the desired product. Appropiate protection/deprotection methods may be used at any point during the synthetic sequence.

The compounds of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion. Examples of these modifications include, but are not limited to, esterification with polyethylene glycols, derivatization with pivolates or fatty acid substituents, conversion to carbamates, hydroxylation of aromatic rings, and heteroatom-substitution in aromatic rings.

As used throughout this application, the term "patient" refers to mammals, including humans. And the term "cell" refers to mammalian cells, including human cells.

Once synthesized, the activities and VLA-4 specificities of the compounds according to this invention may be determined using in vitro and in vivo assays.

For example, the cell adhesion inhibitory activity of these compounds may be measured by determining the concentration of inhibitor required to block the binding of VLA-4-expressing cells to fibronectin- or CS1-coated plates. In this assay microtiter wells are coated with either fibronectin (containing the CS-1 sequence) or CS-1. If CS-1 is used, it must be conjugated to a carrier protein, such as bovine serum albumin, in order to bind to the wells. Once the wells are coated, varying concentrations of the test compound are then added together with appropriately labelled, VLA-4-expressing cells. Alternatively, the test compound may be added first and allowed to incubate with the coated wells prior to the addition of the cells. The cells are allowed to incubate in the wells for at least 30 minutes. Following incubation, the wells are emptied and washed. Inhibition of binding is measured by quantitating the fluorescence or radioactivity bound to the plate for each of the various concentrations of test compound, as well as for controls containing no test compound.

VLA-4-expressing cells that may be utilized in this assay include Ramos cells, Jurkat cells, A375 melanoma cells, as well as human peripheral blood lymophocytes (PBLs). The cells used in this assay may be fluorescently or radioactively labelled.

A direct binding assay may also be employed to quantitate the inhibitory activity of the compounds of this invention. In this assay, a VCAM-IgG fusion protein containing the first two immunoglobulin domains of VCAM (D1D2) attached above the hinge region of an IgG1 molecule ("VCAM 2D-IgG"), is conjugated to a marker enzyme, such as alkaline phosphatase ("AP"). The synthesis of this VCAM-IgG fusion is described in PCT publication WO 90/13300, the disclosure of which is herein incorporated by reference. The conjugation of that fusion to a marker enzyme is achieved by cross-linking methods well-known in the art.

The VCAM-IgG enzyme conjugate is then placed in the wells of a multi-well filtration plate, such as that contained in the Millipore Multiscreen Assay System (Millipore Corp., Bedford, Mass.). Varying concentrations of the test inhibitory compound are then added to the wells followed by addition of VLA-4-expressing cells. The cells, compound and VCAM-IgG enzyme conjugate are mixed together and allowed to incubate at room temperature.

Following incubation, the wells are vacuum drained, leaving behind the cells and any bound VCAM. Quantitation of bound VCAM is determined by adding an appropriate calorimetric substrate for the enzyme conjugated to VCAM-IgG and determining the amount of reaction product. Decreased reaction product indicates increased binding inhibitory activity.

In order to assess the VLA-4 inhibitory specificity of the compounds of this invention, assays for other major groups of integrins, i.e., β2 and β3, as well as other β1 integrins, such as VLA-5, VLA-6 and α4β7 are performed. These assays may be similar to the adhesion inhibition and direct binding assays described above, substituting the appropriate integrin-expressing cell and corresponding ligand. For example, polymorphonuclear cells (PMNs) express β2 integrins on their surface and bind to ICAM. β3 integrins are involved in platelet aggregation and inhibition may be measured in a standard platelet aggregation assay. VLA-5 binds specifically to Arg-Gly-Asp sequences, while VLA-6 binds to laminin. α4β7 is a recently discovered homologue of VLA-4, which also binds fibronectin and VCAM. Specificity with respect to α4β7 is determined in a binding assay that utilizes the above-described VCAM-IgG-enzyme marker conjugate and a cell line that expresses α4β7, but not VLA-4, such as RPMI-8866 cells.

Once VLA-4-specific inhibitors are identified, they may be further characterized in vivo assays. One such assay tests the inhibition of contact hypersensitivity in an animal, such as described by P. L. Chisholm et al., "Monoclonal Antibodies to the Integrin α-4 Subunit Inhibit the Murine Contact Hypersensitivity Response", *Eur. J. Immunol.*, 23, pp. 682–688 (1993) and in "Current Protocols in Immunology", J. E. Coligan, et al., Eds., John Wiley & Sons, New York, 1, pp. 4.2.1–4.2.5 (1991), the disclosures of which is herein incorporated by reference. In this assay, the skin of the animal is sensitized by exposure to an irritant, such as dinitrofluorobenzene, followed by light physical irritation, such as scratching the skin lightly with a sharp edge. Following a recovery period, the animals are re-sensitized following the same procedure. Several days after sensitization, one ear of the animal is exposed to the chemical irritant, while the other ear is treated with a non-irritant control solution. Shortly after treating the ears, the animals are given various doses of the VLA-4 inhibitor by subcutaneous injection. In vivo inhibition of cell adhesion-associated inflammation is assessed by measuring the ear swelling response of the animal in the treated versus untreated ear. Swelling is measured using calipers or other suitable instrument to measure ear thickness. In this manner, one may identify those inhibitors of this invention which are best suited for inhibiting inflammation.

Another in vivo assay that may be employed to test the inhibitors of this invention is the sheep asthma assay. This assay is performed essentially as described in W. M. Abraham et al., "α-Integrins Mediate Antigen-induced Late Bronchial Responses and Prolonged Airway Hyperresponsiveness in Sheep", *J. Clin. Invest.*, 93, pp. 776–87 (1994), the disclosure of which is herein incorporated by reference. This assay measures inhibition of Ascaris antigen-induced late phase airway responses and airway hyperresponsiveness in asthmatic sheep.

The compounds of the present invention may be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, tris(hydroxymethyl) methylamine and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds of the present invention may be formulated into pharmaceutical compositions that may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The pharmaceutical compositions of this invention comprise any of the compounds of the present invention, or pharmaceutically acceptable derivatives thereof, together with any pharmaceutically acceptable carrier. The term "carrier" as used herein includes acceptable adjuvants and vehicles. Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

The dosage and dose rate of the compounds of this invention effective to prevent, suppress or inhibit cell adhesion will depend on a variety of factors, such as the nature of the inhibitor, the size of the patient, the goal of the treatment, the nature of the pathology to be treated, the specific pharmaceutical composition used, and the judgment of the treating physician. Dosage levels of between about 0.001 and about 100 mg/kg body weight per day, preferably between about 0.1 and about 10 mg/kg body weight per day of the active ingredient compound are useful.

According to another embodiment compositions containing a compound of this invention may also comprise an additional agent selected from the group consisting of corticosteroids, bronchodilators, antiasthmatics (mast cell stabilizers), antiinflammatories, antirheumatics, immunosuppressants, antimetabolites, immunonodulators, antipsoriatics and antidiabetics. Specific compounds within each of these classes may be selected from any of those listed under the appropriate group headings in "Comprehensive Medicinal Chemistry", Pergamon Press, Oxford, England, pp. 970–986 (1990), the disclosure of which is herein incorporated by reference. Also included within this group are compounds such as theophylline, sulfasalazine and aminosalicylates (antiinflammatories); cyclosporin, FK-506, and rapamycin (immunosuppressants); cyclophosphamide and methotrexate (antimetabolites); and interferons (immunomodulators).

According to other embodiments, the invention provides methods for preventing, inhibiting or suppressing cell adhesion-associated inflammation and cell adhesion-associated immune or autoimmune responses. VLA4-associated cell adhesion plays a central role in a variety of inflammation, immune and autoimmune diseases. Thus, inhibition of cell adhesion by the compounds of this invention may be utilized in methods of treating or preventing inflammatory, immune and autoimmune diseases. Preferably the diseases to be treated with the methods of this invention are selected from asthma, arthritis, psoriasis, transplantation rejection, multiple sclerosis, diabetes and inflammatory bowel disease.

These methods may employ the compounds of this invention in a monotherapy or in combination with an anti-inflammatory or immunosuppressive agent. Such combination therapies include administration of the agents in a single dosage form or in multiple dosage forms administered at the same time or at different times.

In order that this invention may be more fully understood, the following examples are set forth. These examples are for the purpose of illustration only and are not to be construed as limiting the scope of the invention in any way.

EXAMPLES

General Procedures for Amide Bond Formation in Solution:

Procedure A: Coupling with EDC/HOBt

A solution of carboxylic acid (1.2 eq.) in DMF at 0° C. was treated with HOBT (1.8 eq.) and EDC (1.4 eq.). The mixture was stirred at 0° C. for 1 to 2 h and then the free amine (1.0 eq., neutralized with TEA or DIPEA) was added. After stirring at RT for more than 3 h, the reaction mixture was diluted with ethyl acetate, washed with water (1×), 5% aqueous citric acid (2×), sat. $NaHCO_3$ (2×), and brine (1×), dried ($Na_2SO_4$ or $MgSO_4$), and concentrated in vacuo.

Procedure B: Coupling using Activated Ester (N-hydroxysuccinate or Chloride)

A solution of free amine (1–1.2 eq., neutralized with TEA or DIPEA) in $CH_2Cl_2$ was treated with activated ester or acyl halide (1 eq.) at 0° C. or RT. After stirring at RT for over 1 h, the reaction mixture was washed with 5% aqueous citric acid (2×), sat. $NaHCO_3$ (2×), and brine (1×), dried ($Na_2SO_4$ or $MgSO_4$), and concentrated in vacuo.

General Procedure for Urea Formation in Solution:

Procedure C: Formation of Urea with Isocyanate and Amine.

A solution of amine (1 eq.) and TEA (1 eq.) in $CH_2Cl_2$ was treated with an isocyanate (1 eq.) and was stirred at RT for over 0.5 h. After concentration in vacuo, the product was either used as is or purified by chromatography.

General Procedures for Deprotection in Solution:

Procedure D: Removal of BOC with TFA

A solution of tBuOC(O)NH—R (where R is alkyl optionally substituted with any number of suitable functional groups) in $CH_2Cl_2$ at 0° C. was treated with trifluoroacetic acid. The reaction was allowed to warm to RT and stirred for 1 to 2 h. After concentration in vacuo the resulting amine/TFA salt was stored and neutralized with TEA or DIPEA prior to use.

Procedure E: Removal of BOC with HCl

A solution of tBuOC(O)NH—R (where R is alkyl optionally substituted with any number of suitable functional groups) in dioxane at 0° C. was treated with 4N HCl in dioxane. The reaction was allowed to warm to RT and stirred for 1 to 2 h. After concentration in vacuo the resulting amine/HCl salt was stored and neutralized with TEA or DIPEA prior to use.

Procedure F: Hydrogenation

A mixture of starting material and 10% Pd/C in methanol, water, ethyl acetate, and/or DMF was vigorously stirred under hydrogen (40 to 50 psi) for more than 2 h at RT. The resulting mixture was filtered through a plug of Celite and the filtrate concentrated in vacuo.

General Procedures for Amide Bond Formation on Solid Support:

Procedure G: Coupling with DCC/HOBt

A mixture of resin (see below for preparation of resin MCB1), tBuOC(O)NH—$AA_x$—$CO_2H$ (where AA is an amino acid or functional equivalent) or $R_2$—$CO_2H$ (10 eq.), HOBt (10 eq.), DCC (10 eq) and N-methylmorpholine (3 eq) in NMP was shaken for over 0.5 h at RT. The resin was then washed with NMP (2×) and $CH_2Cl_2$ (3×).

Procedure H: Displacement from Resin with Amine

A mixture of resin and amine (xs) in DMF was shaken for 6 h at RT. The resin was then washed with methanol (3×) and the combined solutions concentrated in vacuo.

General Procedures for Deprotection on Solid Support:

Procedure I: Removal of BOC with TFA/$CH_2Cl_2$

A mixture of resin and 50% TFA/$CH_2Cl_2$ was shaken for over 0.5 h at RT. The resin was then washed with $CH_2Cl_2$ (2×), isopropanol (1×), and $CH_2Cl_2$ (3×).

Procedure J: HF with Scavengers

The protected product was treated with HF at −10 to 0° C. for over 1.5 h in the presence of anisole or thioanisole as scavenger. The HF was removed with a stream of nitrogen gas at 0° C.

Example 1

Synthesis of Common Intermediates

Succinimidyl 3-Isoquinolinecarboxylate (iQn-OSu):

A solution of 3-isoquinolinecarboxylic acid (1.2 eq) in DMF at 0° C. was treated with EDC (1.4 eq.). The mixture was stirred at 0° C. for 1 to 2 h and then N-hydroxysuccinimide (1.0 eq.) was added. After stirring at RT for more than 3 h, the reaction mixture was poured into 60% sat. NaHCO$_3$ and the product filtered: $^1$H NMR (CDCl$_3$, 300 MHz, ppm) 9.35 (s, 1H), 8.67 (s, 1H), 8.09 (m, 1H), 7.96 (m, 1H), 7.82 (m, 2H), 2.94 (s, 4H).

Succinimidyl 2-Quinolinecarboxylate (Qn-OSu):

A solution of 2-quinoline carboxylic acid (1.2 eq.) in DMF at 0° C. was treated with EDC (1.4 eq.). The mixture was stirred at 0° C. for 1 to 2 h and then N-hydroxysuccinimide (1.0 eq.) was added. After stirring at RT for more than 3 h, the reaction mixture was poured into 60% sat. NaHCO$_3$ and the product filtered: $^1$H NMR (CDCl$_3$, 300 MHz, ppm) 8.35 (d, 1H), 8.27 (d, 1H), 8.19 (d, 1H), 7.87 (d, 1H), 7.80 (m, 1H), 7.68 (m, 1H), 2.91 (s, 4H).

Methyl 4-Isocyanatophenylacetate (KCl):

A well-stirred cold solution of methyl p-aminophenylacetate (9.8 g, 59.4 mmol) in CH$_2$Cl$_2$ (200 mL) and TEA (25 mL, 18 g, 178.2 mmol) was treated with COCl$_2$ (96 mL of 1.9 M solution in toluene) over 1 h. The reaction mixture was stirred at 0° C. for an additional 1 h. The reaction mixture was concentrated and 3:1 ether/pet ether (125 mL) was added. The mixture was filtered and the filtrate concentrated to give KCl as a brown liquid. The crude product was purified by distillation (118–120° C./1.0 mm) to afford pure KCl (8.5 g, 75%) as a colorless liquid: $^1$H NMR (CDCl$_3$, 300 MHz, ppm) 7.20 (d, J=8.4 Hz), 7.02 (d, J=8.4 Hz), 3.69 (s, 3H), 3.48 (s, 2H).

4-Phenylureidophenylacetic acid:

4-Phenylureidophenylacetic acid was prepared using procedure C with 4-amino-phenylacetic acid and phenyl isocyanate: $^1$H NMR (CD$_3$SOCD$_3$, 300 MHz, ppm) 8.72–8.64 (m, 2H), 7.44 (d, 2H), 7.36 (d, 2H), 7.28 (d, 2H), 7.16 (d, 2H), 6.96 (t, 1H), 3.52 (s, 2H); m/z 272.

4-o-Tolylureidophenylacetic acid:

4-o-Tolylureidophenylacetic acid was prepared using procedure C with 4-amino-phenylacetic acid and o-tolyl isocyanate: $^1$H NMR (CD$_3$SOCD$_3$, 300 MHz, ppm) 8.97 (s, 1H), 7.88 (s, 1H), 7.83 (d, 1H), 7.38 (d, 2H), 7.17–7.09 (m, 4H), 6.92 (t, 1H), 3.48 (s, 2H), 2.23 (s, 3H); m/z 285.

4-(2-Fluorophenyl)ureidophenylacetic acid:

4-(2-Fluorophenyl)ureidophenylacetic acid was prepared using procedure C with 2-fluoroaniline and KCl: $^1$H NMR (CD$_3$SOCD$_3$, 300 MHz, ppm) 9.00 (s, 1H), 8.51 (d, 2.4 Hz, 1H), 8.14 (dd, 8.3 Hz, 1.5 Hz, 1H), 7.37 (d, 8.5 Hz, 2H), 7.07–7.25 (m, 4H), 6.99 (m, 1H), 3.48 (s, 2H).

4-(2-Hydroxyphenylureido)phenylacetic acid:

4-(2-Hydroxyphenylureido)phenylacetic acid was prepared using procedure C with 2-hydroxyaniline and KCl: $^1$H NMR (CD$_3$SOCD$_3$, 300 MHz, ppm) 9.90 (s, 1H), 9.25 (s, 1H), 8.12 (s, 1H), 8.02 (bd, 1H), 7.37 (d, 2H), 7.13 (d, 2H), 6.70–6.97 (m, 3H), 3.48 (s, 2H).

N-Succinimidyl 4-(2-(3-methylpyridylureido) phenylacetate:

Prepared in three steps as follows:

Procedure C with 2-amino-3-methylpyridine and KCl to give methyl 4-(2-(3-methylpyridylureido)phenylacetate.

A solution of methyl 4-(2-(3-methylpyridylureido) phehylacetate (1 eq.) in methanol was treated with 1 N NaOH (2 eq.). The reaction was stirred for 16 h, then acidified carefully with 1 N HCl to pH 7 then with acetic acid to pH 3. The product was filtered and washed with methanol then ether to give 4-(2-(3-methylpyridylureido) phenylacetic acid: $^1$H NMR (CD$_3$SOCD$_3$, 300 MHz, ppm) 11.97 (s, 1H), 8.64 (brs, 1H), 8.31 (s, 1H), 7.69 (m, 1H), 7.62 (d, 8.4 Hz, 2H), 7.33 (d, 8.4 Hz, 2H), 7.09 (m, 1H), 3.62 (s, 2H), 2.38 (s, 3H); m/z 286.

A solution of 4-(2-(3-methylpyridylureido)phenylacetic acid (1 eq.), N-hydroxysuccinimide (1.2 eq.) and EDC (1.2 eq.) in DMF was made basic (pH 10) with TEA. After stirring at RT for over 12 h, the reaction was poured into 60% sat NaHCO$_3$ and the product filtered: $^1$H NMR (CD$_3$SOCD$_3$, 300 MHz, ppm) 12.04 (s, 1H), 8.84 (s, 1H), 8.31 (s, 1H), 7.72 (m, 3H), 7.42 (m, 2H), 7.10 (m, 1H), 4.18 (s, 2H), 2.98 (3, 4H), 2.38 (s, 3H); m/z 383.

N-Succinimidyl 4-(2-pyridylureido)phenylacetate:

Prepared in three steps as follows:

Procedure-C with 2-aminopyridine and KCl to give methyl 4-(2-pyridylureido)phenylacetate: $^1$H NMR (CDCl$_3$, 300 MHz, ppm) 8.20 (s, 2H), 7.62–7.51 (m, 3H), 7.33 (d, 2H), 7.01 (d, 2H), 6.89–6.85 (m, 1H), 3.70 (s, 3H), 3.59 (s, 2H).

A solution of methyl 4-(2-pyridylureido)phenylacetate (5.7 g, 20.0 mmol) in methanol (20 mL) was treated with 1 N NaOH (40 mL). The reaction was stirred for 16 h, then acidified carefully with 1 N HCl to pH 7 then with acetic acid to pH 3. The product was filtered and washed with methanol then ether to give 4-(2-pyridyl)ureidophenylacetic acid (4.7 g, 87%) as a white powder: $^1$H NMR (CD$_3$SOCD$_3$, 300 MHz, ppm) 10.62 (bs, 1H), 9.53 (bs, 1H), 8.39 (d, 1H), 7.82 (t, 1H), 7.63–7.55 (m, 1H), 7.33–7.27 (d, 2H), 7.14–7.08 (m, 1H), 3.62 (s, 3H).

A solution of 4-(2-pyridyl)ureidophenylacetic acid (1 eq.), N-hydroxysuccinimide (1.2 eq.) and EDC (1.2 eq.) in DMF was made basic (pH 10) with TEA. After stirring at RT for over 12 h, the reaction was poured into 60% sat. NaHCO$_3$ and the product filtered: $^1$H NMR (CD$_3$SOCD$_3$, 300 MHz, ppm) 10.08 (s, 1H), 9.57 (s, 1H), 8.39 (m, 1H), 7.86 (m, 1H), 7.62 (m, 3H), 7.38 (d, 2H), 7.12 (m, 1H), 4.15 (s, 2H), 2.91 (s, 4H); m/z 369.

3-Methoxy-4-phenylureidophenylacetic acid:

Prepared in six steps from 3-methoxy-4-nitrobenzoic acid as follows:

A mixture of 3-methoxy-4-nitrobenzoic acid (2.01 g, 10.2 mmol) and thionyl chloride (2.3 mL, 31.5 mmol) was stirred at 80–90° C. for 1.5 h. The reaction was concentrated and the residue diluted with ether. The organic solution was washed with sat. aq. NaHCO$_3$ (2×), H$_2$O, then sat. aq. NaCl, dried (MgSO$_4$) and concentrated to afford 3-methoxy-4-nitrobenzoyl chloride (1.92 g, 87%) as a white solid: $^1$H NMR (CDCl3, 300 MHz, ppm) 7.95–7.70 (m, 3H), 4.06 (s, 3H).

A cold (0° C.) solution of TMSCHN$_2$ (2 M in hexane, 1.5 mL, 3.0 mmol) and triethylamine (420 μL, 3.0 mmol) was treated with a solution of 3-methoxy-4-nitrobenzoyl chloride (0.52 g, 2.4 mmol) in acetonitrile (8.5 mL). The reaction was stirred at 0° C. for 24 h and then concentrated. The residue was slurried with sat. aq. NaHCO$_3$ and the mixture extracted with ether (3×). The combined ether washes were washed with water, then sat. aq. NaCl, dried (MgSO$_4$) and concentrated to afford ω-diazo-3-methoxy-4-nitroacetophenone (0.53 g, 100%) as a yellow foam: $^1$H NMR (CDCl$_3$, 300 MHz, ppm) 7.88 (d, 10 Hz, 1H), 7.61 (s, 1H), 7.27 (d, 10 Hz, 1H), 5.97 (s, 1H), 4.02 (s, 3H).

A refluxing solution of ω-diazo-3-methoxy-4-nitroacetophenone (7.95 g, 35.9 mmol) in t-BuOH (100 mL) was treated with a filtered solution of silver benzoate (2.50 g, 10.9 mmol) in triethylamine (15 mL) dropwise over 1 h. After refluxing for 45 min, decolorizing carbon was added and the hot mixture filtered through a pad of Celite. The filtrate was concentrated and the residue diluted with ethyl acetate. The organic solution was washed with 5% aq. NaHCO$_3$ (2×), H$_2$O, 5% aq. citric acid, H$_2$O, then sat. aq. NaCl, dried (MgSO$_4$) and concentrated to afford t-butyl 3-methoxy-4-nitrophenylacetate (8.92 g, 93%) as a brown oil: $^1$H NMR (CDCl$_3$, 300 MHz, ppm) 7.83 (d, 8.3 Hz, 1H), 7.03 (s, 1H), 6.93 (d, 8.3 Hz, 1H), 3.97 (s, 3H), 3.58 (s, 2H), 1.45 (s, 9H).

A mixture of t-butyl 3-methoxy-4-nitrophenylacetate (0.144 g, 0.539 mmol) and 10% Pd on carbon (0.155 g) in ethyl acetate (8 mL) and methanol (2 mL) was stirred under H$_2$ (40–60 psi) for 2 h. The mixture was filtered through Celite and the filtrate concentrated to afford t-butyl 4-amino-3-methoxyphenylacetate (0.123 g, 96%) as a light yellow oil: $^1$H NMR (CDCl$_3$, 300 MHz, ppm) 6.70 (m, 3H), 4.04 (bs, 2H), 3.84 (s, 3H), 3.42 (s, 2H), 1.43 (s, 9H).

Procedure C with t-butyl 4-amino-3-methoxyphenylacetate and phenyl isocyanate gave t-butyl 3-methoxy-4-phenylureidophenylacetate: $^1$H NMR (CDCl$_3$, 300 MHz, ppm) 8.00 (d, 11 Hz, 1H) 7.65–6.94 (m, 7H), 6.80 (d, 9.0 Hz, 1H), 6.74 (s, 1H), 3.68 (s, 3H), 3.45 (s, 2H), 1.44 (s, 9H).

A solution of t-butyl 3-methoxy-4-phenylureidophenylacetate (0.108 g, 0.303 mmol) in trifluoroacetic acid (5.0 mL) was stirred for 30 min. The reaction was concentrated and the residue coevaporated with methylene chloride (2×) then ether to afford 3-methoxy-4-phenylureidophenylacetic acid (0.090 g, 99%) as a white foam: $^1$H NMR (CD$_3$SOCD$_3$, 300 MHz, ppm) 9.28 (s, 1H), 8.18 (s, 1H), 8.02 (d, 7.5 Hz, 1H), 7.58–7.15 (m, 5H), 6.91 (bm, 2H), 6.77 (d, 7.5 Hz, 1H), 3.85 (s, 3H), 3.49 (s, 2H).
N-Succinimidyl 3-methoxy-4-phenylureidophenylacetate:

A solution of 3-methoxy-4-phenylureidophenylacetic acid (1 eq.) in DMF at 0° C. was treated with EDC (1.1 eq.). The mixture was stirred at 0° C. for 1 to 2 h and then N-hydroxysuccinimide (1.1 eq.) was added. After stirring at RT for more than 3 h, the reaction mixture was poured into 60% sat. NaHCO$_3$ and the N-succinimidyl 3-methoxy-4-phenylureidophenylacetate filtered.
N-Succinimidyl 6-(2-methoxy-3-o-tolylureido) pyridylacetate:
Prepared in six steps from 2,6-dichloro-3-nitropyridine as follows:

A slurry of 2,6-dichloro-3-nitropyridine (92%, 9.9 g, 47 mmol) and K$_2$CO$_3$ powder (6.5 g, 47 mmol) in methanol (100 mL) was stirred for a week at RT. The reaction was filtered and concentrated. The residue was partitioned in ethyl acetate and 60% sat. aq. NaHCO$_3$. The organic solution was washed with 60% sat. aq. NaHCO$_3$ (2×), H$_2$O, then sat. aq. NaCl, dried (MgSO$_4$) and concentrated to afford 2-chloro-6-methoxy-5-nitropyridine and 2-chloro-6-methoxy-3-nitropyridine (8.9 g, 100%) as a light yellow solid: $^1$H NMR (CDCl$_3$, 300 MHz, ppm) 8.31 (d, 8.3 Hz, 1H), 8.28 (d, 8.9 Hz, 1H), 7.10 (d, 8.3 Hz, 1H), 6.82 (d, 8.9 Hz, 1H), 4.15 (s, 3H), 4.06 (s, 3H).

A mixture of 2-chloro-6-methoxy-5-nitropyridine and 2-chloro-6-methoxy-3-nitropyridine (8.9 g, 47 mmol), t-butyl methyl malonate (10 mL, 60 mmol), and NaH (95%, 3.1 g, 120 mmol) in THF (250 mL) was stirred at RT for 24 h. The reaction was concentrated and the residue treated with trifluoroacetic acid (200 mL) for 2 h. The reaction was concentrated and the product separated by flash chromatography (silica gel, 95:5 hexane-ethyl acetate) to afford methyl 6-(2-methoxy-3-nitro)pyridylacetate (3.3 g, 62%) as a yellow oil: $^1$H NMR (CDCl$_3$, 300 MHz, ppm) 8.27 (d, 8.0 Hz, 1H), 7.04 (d, 8.0 Hz, 1H), 4.09 (s, 3H), 3.85 (s, 2H), 3.75 (s, 3H).

A mixture of methyl 6-(2-methoxy-3-nitro)pyridylacetate (0.047 g, 0.21 mmol) and 10% Pd on carbon (0.063 g) in ethyl acetate (2 mL) and ethanol (1 mL) was stirred under H$_2$ (40–50 psi) for 6 h. The mixture was filtered through Celite and the filtrate concentrated to afford methyl 6-(2-methoxy-3amino)pyridylacetate (0.041 g, 100%) as a light yellow oil: $^1$H NMR (CDCl$_3$, 300 MHz, ppm) 6.82 (d, 7.6 Hz, 1H), 6.65 (d, 7.6 Hz, 1H), 3.94 (s, 3H), 3.70 (s, 3H), 3.65 (s, 2H).

Procedure C with methyl 6-(2-methoxy-3-amino) pyridylacetate and o-tolyl isocyanate to give methyl 6-(2-methoxy-3-o-tolylureido)pyridylacetate: $^1$H NMR (CDCl$_3$, 300 MHz, ppm) 8.33 (d, 7.9 Hz, 1H), 7.51 (d, 7.8 Hz, 1H), 7.41 (s, 1H), 7.17 (m, 2H), 7.08 (m, 2H), 6.77 (d, 7.9 Hz, 1H), 3.81 (s, 3H), 3.71 (s, 3H), 3.67 (s, 2H), 2.20 (s, 3H).

A solution of methyl 6-(2-methoxy-3-o-tolylureido) pyridylacetate (0.023 g, 0.070 mmol) in methanol (1.0 mL) was treated with 2 M LiOH (90 μL, 0.18 mmol). The reaction was stirred for 18 h, diluted with H$_2$O (5.0 mL) and washed with ether (2×). The aqueous solution was then acidified with 5% aq. citric acid. The product was filtered and washed with H$_2$O then ether to give 6-(2-methoxy-3-o-tolylureido)pyridylacetic acid (0.014 g, 64%) as a white solid: $^1$H NMR (CD$_3$OD, 300 MHz, ppm) 8.50–8.25 (m, 3H), 7.60 (bd, 1H), 7.28–7.00 (m, 3H), 4.01 (s, 3H), 3.69 (s, 2H), 2.30 (s, 3H); MS, m/z 316.

A solution of 6-(2-methoxy-3-o-tolylureido)pyridylacetic acid (1.61 g, 5.10 mmol) in DMF at 0° C. was treated with EDC (1.00 g, 5.2 mmol). The mixture was stirred at 0° C. for 1 to 2 h and then N-hydroxysuccinimide (0.60 g, 5.2 mmol) was added. After stirring at RT for more than 3 h, the reaction mixture was poured into 60% sat. NaHCO$_3$ and the N-succinimidyl 6-(2-methoxy-3-o-tolylureido) pyridylacetate filtered.
H-LD(OBn)V-NHCH$_3$:

H-LD(OBn)V-NHCH$_3$ was prepared by sequentially using procedure B with BOC-Val-OSu and methylamine, procedure D, procedure B with BOC-Asp(OBn)-OSu, procedure D, procedure B with BOC-Leu-OSu, then procedure D.
H-LD(OBn)V-OCH$_3$:

H-LD(OBn)V-OCH$_3$ was prepared by sequentially using procedure B with BOC-Asp(OBn)-OSu and H-Val-OMe, procedure D, procedure B with BOC-Leu-OSu, then procedure D.
H-LD(OBn)V-OBn:

H-LD(OBn)V-OBn was prepared by sequentially using procedure B with BOC-Asp(OBn)-OSu and H-Val-OBn, procedure D, procedure B with BOC-Leu-OSu, then procedure D.
H-LD(OBn)VP-OBn:

H-LD(OBn)VP-OBn was prepared by sequentially using procedure B with BOC-Val-OSu and H-Pro-OBn, procedure D, procedure B with BOC-Asp(OBn)-OSu, procedure D, procedure B with BOC-Leu-OSu, then procedure D.
H-LD(OBn)VP-OMe:

H-LD(OBn)VP-OMe was prepared by sequentially using procedure A with BOC-Val-OH and H-Pro-OMe, procedure, D, procedure B with BOC-Asp(OBn)-OSu, procedure D, procedure B with BOC-Leu-OSu, then procedure D.
H-LDVP-OH:

H-LDVP-OH was prepared by sequentially using procedure B with BOC-Val-OSu and H-Pro-OBn, procedure D, procedure B with BOC-Asp(OBn)-OSu, procedure D, procedure B with BOC-Leu-OSu, procedure F, then procedure D.
H-MD (OBn)VP-OBn:

H-MD(OBn)VP-OBn was prepared by sequentially using procedure B with BOC-Val-OSu and H-Pro-OBn, procedure D, procedure B with BOC-Asp(OBn)-OSu, procedure D, procedure B with BOC-Met-OSu, then procedure D.
H-LD(OBn)VP-NH$_2$:

H-LD(OBn)VP-NH$_2$ was prepared by sequentially using procedure B with BOC-Val-OSu and H-Pro-NH$_2$, procedure D, procedure B with BOC-Asp(OBn)-OSu, procedure D, procedure B with BOC-Leu-OSu, then procedure D.

Resin (MBC1):

Modified resin MBC1 (0.437 mmol/g) was synthesized according to the literature procedure (see: Richter, L. S., et al., *Tetrahedron Lett*. 35, p. 5547 (1994)). MBC1 was treated with 50% TFA/CH$_2$Cl$_2$ and triethylsilane for 2 h at RT then washed with CH$_2$Cl$_2$ (2×), isopropanol (1×), and CH$_2$Cl$_2$ (3×) before use.

MBC2:

MBC2 was prepared by sequentially using procedure G with BOC-Asp(OBn)-OH, procedure I, procedure G with BOC-Leu-OH, procedure I, then procedure G with 4-phenylureidophenylacetic acid.

MBC3:

MBC3 was prepared by sequentially using procedure G with BOC-Val-OH, procedure I, procedure G with BOC-Asp(OBn)-OH, procedure I, procedure G with BOC-Leu-OH, procedure I, then procedure G with 4-phenylureidophenylacetic acid.

MBC4:

MBC4 was prepared by sequentially using procedure G with BOC-Pro-OH, procedure I, procedure G with BOC-Val-OH, procedure I, procedure G with BOC-Asp(OBn)-OH, procedure I, procedure G with BOC-Leu-OH, procedure I, then procedure G with 4-phenylureidophenylacetic acid.

Example 2

Compound 77:

Compound 77 was prepared by using procedure A with picolinic acid and H-LD(OBn)V-OBn then procedure F. Purification by HPLC gave the title compound: m/z 451.

Example 3

Compound 64:

Compound 64 was prepared by using procedure A with hydrocinnamic acid and H-LD(OBn)V-OBn then procedure F. Purification by HPLC gave the title compound: m/z 478.

Example 4

Compound 155:

Compound 155 was prepared by using procedure B with chloro 4-phenylbutyrate and H-LD(OBn)V-OBn then procedure F. Purification by HPLC gave the title compound: m/z 492.

Example 5

Compound 157:

Compound 157 was prepared by using procedure B with BOC-Asp(OBn)-OSu and isobutylamine, procedure D, procedure B with BOC-Leu-OSu, procedure D, procedure B with iQn-OSu, then procedure F. Purification by HPLC gave the title compound: m/z 457.

Example 6

Compound 164:

Compound 164 was prepared by using procedure B with Qn-OSu and H-LD(OBn)V-NHCH$_3$ then procedure F. Purification by HPLC gave the title compound: m/z 514.

Example 7

Compound 174:

Compound 174 was prepared by using procedure B with BOC-Asp(OBn)-OSu and valinol, procedure D, procedure B with BOC-Leu-OSu, procedure D, procedure B with Qn-OSu, then procedure F. Purification by HPLC gave the title compound: m/z 487.

Example 8

Compound 177:

Compound 177 was prepared by using procedure B with BOC-Asp(OBn)-OSu and H-Thr-OCH$_3$, procedure D, procedure B with BOC-Leu-OSu, procedure D, procedure B with 4-methoxybenzenesulfonyl chloride, then procedure F. Purification by HPLC gave the title compound: m/z 532.

Example 9

Compound 180:

Compound 180 was prepared by using procedure B with BOC-Val-OSu and methylamine, procedure D, procedure B with BOC-Asp(OBn)-OSu, procedure D, procedure B with BOC-N-MeLeu-OSu, procedure D, procedure B with phenylacetyl chloride, then procedure F. Purification by HPLC gave the title compound: m/z 491.

Example 10

Compound 189:

Compound 189 was prepared by using procedure B with BOC-Val-OSu and methylamine, procedure D, procedure B with BOC-Asp(OBn)-OSu, procedure D, procedure B with BOC-Leu-OSu, procedure D, procedure B with phenylsulfonyl chloride, then procedure F. Purification by HPLC gave the title compound: m/z 499.

Example 11

Compound 345:

Compound 345 was prepared by using procedure A with 4-o-tolylureidophenylacetic acid and H-LD(OBn)V-OBn then procedure F. Purification by HPLC gave the title compound: m/z 606.

Example 12

Compound 206:

Compound 206 was prepared by using procedure A with 4-o-tolylureidophenylacetic acid and H-LD(OBn)VP-OBn then procedure F. Purification by HPLC gave the title compound: m/z 709.

Example 13

Compound 144:

Compoound 144 was prepared by using procedure A with 4-(2-hydroxyphenylureido) phenylacetic acid and H-LD(OBn)VP-OBn then procedure F. Purification by HPLC gave the title compound: m/z 711, 24.6 min (gradient 8).

Example 14

Compound 145:

Compound 145 was prepared by using procedure A with 4-phenylureidophenylacetic acid and H-LD(OBn)VP-OBn then procedure F. Purification by HPLC gave the title compound: m/z 695, 26.8 min (gradient 8).

Example 15

Compound 146:

Compound 146 was prepared by using procedure A with 4-(2-hydroxyphenylureido) phenylacetic acid and H-MD(OBn)VP-OBn then procedure F. Purification by HPLC gave the title compound: m/z 729, 22.4 m in (gradient 8).

Example 16

Compound 1:

Compound 1 was prepared by using procedure A with 3-methoxy-4-phenylureidophenylacetic acid and H-LD (OBn)VP-OBn then procedure F. Purification by HPLC gave the title compound: m/z 725, 28.5 min (gradient 8).

Example 17
Compound 2:

Compound 2 was prepared by using procedure A with 3-methoxy-4-phenylureidophenylacetic acid and H-MD(OBn)VP-OBn then procedure F. Purification by HPLC gave the title compound: m/z 743, 27.0 min (gradient 8).

Example 18
Compound 315:

Compound 315 was prepared by using procedure A with 4-o-tolylureidophenylacetic acid and H-MD(OBn)VP-OBn then procedure F. Purification by HPLC gave the title compound: m/z 727.

Example 19
Compound 346:

Compound 346 was prepared by using procedure B with N-Hydroxysuccinimidyl 4-(2-(3-methylpyridylureido) phenylacetate and H-LDVP-OH. Purification by HPLC gave Compound 346: m/z 710.

Example 20
Compound 316:

Compound 316 was prepared by using procedure B with N-hydroxysuccinyimidyl 4-(2-pyridylureido)phenylacetate and H-LDVP-OH. Purification by HPLC gave the title compound: m/z 696.

Example 21
Compound 4:

Compound 4 was prepared by using procedure B with N-hydroxysuccinimidyl 6-(2-methoxy-3-o-tolylureido) pyridylacetate and H-LDVP-OH. Purification by HPLC gave the title compound: m/z 740, 30.7 min (gradient 8).

Example 22
Compound 147:

Compound 147 was prepared by using procedure B with N-hydroxysuccinimidyl 3-methoxy-4-phenylureidophenylacetate and H-LD(OBn)VP-NH$_2$ then procedure F. Purification by HPLC gave the title compound: m/z 724, 26.7 min (gradient 8).

Example 23
Compound 148:

Compound 148 was prepared by using procedure A with 4-o-tolylureidophenylacetic acid and H-LD(OBn)VP-NH$_2$ then procedure F. Purification by HPLC gave the title compound: m/z 708, 26.0 min (gradient 8).

Example 24
Compound 317:

Compound 317 was prepared by using procedure B with N-hydroxysuccinimidyl 6-(2-methoxy-3-o-tolylureido) pyridylacetate and H-LD(OBn)VP-NH$_2$ then procedure F. Purification by HPLC gave the title compound: m/z 739, 28.0 min (gradient 8).

Example 25
Compound 336:

Compound 336 was prepared by using procedure A with 4-(2-fluorophenyl)ureidophenylacetic acid and H-LD(OBn)VP-OBn then procedure F. Purification by HPLC gave the title compound: m/z 713.

Example 26
Compound 32:

Compound 32 was prepared by using procedure B with iQn-OSu and H-LD(OBn)VP-OBn then procedure F. Purification by HPLC gave the title compound: m/z 598, 24.7 min (gradient 8).

Example 27
Compound 34:

Compound 34 was prepared by using procedure B with phenylacetyl chloride and H-LD(OBn)VP-OBn then procedure F. Purification by HPLC gave the title compound: m/z 561, 23.7 min (gradient 8).

Example 28
Compound 39:

Compound 39 was prepared by using procedure A with 3-(-4-hydroxyphenyl)propionic acid and H-LD(OBn)VP-OMe then procedure F. Purification by HPLC gave Compound 39: m/z 591, 21.5 min (gradient 8).

Example 29
Compound 42:

Crude compound 42 was prepared by sequentially using procedure A with BOC-Val-OH and H-homoPro-OBn, procedure D, procedure B with BOC-Asp(OBn)-OSu, procedure D, procedure B with BOC-Leu-OSu, procedure D, procedure B with phenyl acetyl chloride then procedure F. Purification by HPLC gave the title compound: m/z 575, 26.4 min (gradient 8).

Example 30
Compound 52:

Compound 52 was prepared by sequentially using procedure A with BOC-norVal-OH and methylamine, procedure D, procedure B with BOC-Asp(OBn)-OSu, procedure D, procedure B with BOC-Leu-OSu, procedure D, procedure B with Qn-OSu then procedure F. Purification by HPLC gave the title compound: m/z 518, 30.2 min (gradient 8).

Example 31
Compound 46:

Compound 46 was prepared by sequentially using procedure A with BOC-Val-OH and methylamine, procedure D, procedure B with BOC-Asp(OBn)-OSu, procedure D, procedure A with BOC-N-MeLeu-OH, procedure D, procedure A with 3-(4-hydroxyphenyl)propionic acid then procedure F. Purification by HPLC gave the title compound: m/z 521, 18.7 min (gradient 8).

Example 32
Compound 61:

Compound 61 was prepared by sequentially using procedure B with BOC-Thr-OSu and morpholine, procedure D, procedure B with BOC-Asp(OBn)-OSu, procedure D, procedure B with BOC-Leu-OSu, procedure D, procedure B with Qn-OSu then procedure F. Purification by HPLC gave the title compound: m/z 572, 24.0 min (gradient 8).

Example 33
Compound 213:

Compound 213 was prepared by using procedure H with MBC2 and benzyamine then procedure J: m/z 588.

Example 34
Compound 214:

Compound 214 was prepared by using procedure H with MBC2 and morpholine then procedure J: m/z 568.

Example 35
Compound 215:
Compound 215 was prepared by using procedure H with MBC2 and isopropylamine then procedure J: m/z 540.

Example 36
Compound 216:
Compound 216 was prepared by using procedure H with MBC2 and cyclohexylamine then procedure J: m/z 580.

Example 37
Compound 217:
Compound 217 was prepared by using procedure H with MBC2 and isobutylamine then procedure J: m/z 554.

Example 38
Compound 218:
Compound 218 was prepared by using procedure H with MBC2 and piperdine then procedure J: m/z 566.

Example 39
Compound 318:
Compound 318 was prepared by using procedure H with MBC3 and morpholine then procedure J: m/z 667.

Example 40
Compound 319:
Compound 319 was prepared by using procedure H with MBC3 and isopropylamine then procedure J: m/z 640.

Example 41
Compound 320:
Compound 320 was prepared by using procedure H with MBC3 and cyclohexylamine then procedure J: m/z 679.

Example 42
Compound 321:
Compound 321 was prepared by using procedure H with MBC3 and benzylamine then procedure J: m/z 687.

Example 43
Compound 322:
Compound 322 was prepared by using procedure H with MBC3 and piperidine then procedure J: m/z 665.

Example 44
Compound 323:
Compound 323 was prepared by using procedure H with MBC3 and isobutylamine then procedure J: m/z 653.

Example 45
Compound 324:
Compound 324 was prepared by using procedure H with MBC4 and cyclohexylamine then procedure J: m/z 777.

Example 46
Compound 325:
Compound 325 was prepared by using procedure H with MBC4 and piperdine then procedure J: m/z 763.

Example 47
Compound 326:
Compound 326 was prepared by using procedure H with MBC4 and benzylamine then procedure J: m/z 785.

Example 48
Compound 327:
Compound 327 was prepared by using procedure H with MBC4 and isopropylamine then procedure J: m/z 736.

Example 49
Compound 328:
Compound 328 was prepared by using procedure H with MBC4 and isobutylamine then procedure J: m/z 750.

Example 50
Compound 363

A. A mixture of o-tolylureidophenylacetic acid (3.53 g, 12.4 mmol), H-Leu-OtBu.HCl (2.78 g, 12.4 mmol), TBTU (3.98 g, 12.4 mmol), and iPr$_2$NEt (4.32 mL, 24.8 mmmol) in DMF (25 mL) was stirred overnight at RT. The product was precipitated by addition of H2O (10 mL). The solids were collected by filtration on a medium frit, washing with 2:1 DMF/H$_2$O (35 mL), H$_2$O (25 mL), and Et$_2$O (2×25 mL), and dried on the filter (4.18 g, 74%). All of this product was suspended in CH$_2$Cl$_2$ (16 mL) and treated with TFA (16 mL) and stirred at RT 2 hr. The reaction was concentrated to a syrup which was evaporated from CH$_2$Cl$_2$ (2×20 mL). The residue was triturated with Et$_2$O (100 mL) at RT for 2 hr. The solids were collected by filtration on a medium frit, washing with Et$_2$O (50 mL), and dried on the filter (3.40 g, 93%): MS (FAB) 398.

B. A mixture of DCC (0.206 g, 1.0 mmol) and HOBT (0.135 g, 1.0 mmol) in EtOAc (6 mL) was stirred at RT 20 min until homogeneous. Fmoc-Asp-OtBu (0.411 g, 1.0 mmol), piperonylamine (0.12 mL, 1.0 mmol) and N-methylmorpholine (0.22 mL, 2.0 mmol) were added. After stirring overnight, the reaction was filtered to remove solids and the cake washed with fresh EtOAc (10 mL). The filtrate was washed with H$_2$O (2×), 5% citric acid (1×), 5% NaHCO$_3$ (1×), and brine (1×), and dried (MgSO$_4$). Flash column chromatography on SiO$_2$ eluting with 100% CHCl$_3$ to 2% MeOH/CHCl$_3$ provided 0.54 g (100%) of pure product as a solid: mp=128–130° C.; TLC(2% MeOH/CHCl$_3$) R$_f$=0.10; MS (FAB) 545; $^1$H NMR (CDCl$_3$, 300 MHz, ppm) 7.75–7.72 (m, 2H), 7.59–7.56 (m, 2H), 7.40–7.34 (m, 2H), 7.30–7.25 (m, 2H), 6.71–6.66 (m, 3H), 6.13–6.10 (m, 2H), 5.84 (s, 2H), 4.46 (m, 1H), 4.38–4.16 (m, 5H), 2.86 (dd, 1H, J=4.7, 15.6 Hz), 2.72 (dd, 1H, J=4.16, 15.6 Hz), 1.45 (s, 9H).

C. The product from Example 50B (0.25 g, 0.46 mmol), piperidine (0.45 mL, 4.6 mmol), and CH$_2$Cl$_2$ (0.45 mL) were stirred at RT for 90 min. The reaction was evaporated to a solid residue. Flash column chromatography on SiO$_2$ using a MeOH/EtOAc gradient provided product (0.138 g, 93%) as a colorless oil: MS (FAB) 323; TLC(10% MeOH/EtOAc) R$_f$=0.15; $^1$H NMR (CDCl$_3$, 300 MHz, ppm) 7.63 (br s, 1H), 6.75–6.68 (m, 3H), 5.90 (s, 2H), 4.34 (dd, 1H, J=5.7, 14.7 Hz), 4.28 (dd, 1H, J=5.7, 14.7 Hz), 3.65 (dd, 1H, J=3.4, 9.3 Hz), 2.62 (dd, 1H, J=3.4, 15.7 Hz), 2.38 (dd, 1H, J=9.3, 15.7 Hz), 1.74 (s, 2H), 1.42 (s, 9H).

D. The product from Example 50C (2.55 g, 7.91 mmol) and Eschenmoser's salt (1.61 g, 8.70 mmol) were refluxed in MeCN (80 mL) under an inert atmosphere for 42 hr. The reaction was cooled to RT and evaporated to dryness. The residue was diluted with 5% NaHCO$_3$ and extracted with EtOAc (3×). The combined organic extracts were washed with 5% NaHCO$_3$ (1×), H$_2$O (1×), and brine (1×), and dried (MgSO$_4$). The crude product was dissolved in Et$_2$O (250 mL) and passed through a short pad of SiO$_2$, eluting with Et$_2$O followed by EtOAc. The slightly impure product thus obtained was further purified by trituration with ice cold Et$_2$O (30 mL) and collected by filtration to give a white solid (0.904 g, 34%): mp=121–123° C.; TLC (10% MeOH/CHCl$_3$) R$_f$=0.59; $^1$H NMR (CDCl$_3$, 300 MHz, ppm) 6.75–6.66 (m, 3H), 5.92 (s, 2H), 4.66 (A of AB, 1H, J=14.7 Hz), 4.23 (B of AB, 1H, J=14.7 Hz), 4.15 (ABq, 2H, J=11.9 Hz), 3.68 (dd, dd, 1H, J=5.2, 10.9 Hz), 2.72 (dd, 1H, J=5.2, 17.3 Hz), 2.41 (dd, 1H, J=10.9, 17.3 Hz), 1.45 (s, 9H); C,H,N for $C_{17}H_{22}N_2O_5$, theory—C: 61.07, H: 6.63, N: 8.38, found—C: 60.80, H: 6.59, N: 8.22.

E. The product from Example 50D (0.50 g, 1.5 mmol), the product from Example 50A (0.596 g, 1.5 mmol), and EDC (0.314 q, 1.64 mmol) were stirred in NMP (3 mL) at RT for 48 hr. The reaction was poured into EtOAc (60 mL), washed with $H_2O$ (8×6 mL), brine (1×), and dried ($MgSO_4$). Flash column chromatography on $SiO_2$ eluting with 100% $CHCl_3$ to 30% $EtOAc/CHCl_3$ provided product (0.94 g, 88%) as a pale yellow oil: MS (FAB) 714; TLC (10% $MeOH/CHCl_3$) $R_f$=0.40; $^1H$ NMR ($CDCl_3$, 300 MHz, ppm) consistent with structure and indicative of diastereomers.

F. The product from Example 50E (0.94 g, 1.32 mmol) was stirred in TFA (10 mL) at RT for 3 hr. The reaction was concentrated to dryness and the residue evaporated from $CH_2Cl_2$ (3×10 mL). The crude product was triturated with $Et_2O$ at RT, collected by filtration and dried on the filter (0.733 g, 84%): MS (FAB) 658 (M+H), 680 (M+Na); TLC (5% HOAc/EtOAc) $R_f$=0.15; $^1H$ NMR ($d^6$-DMSO, 300 MHz, ppm) consistent with structure and indicative of diastereomers.

Example 51

Compound 364:

A. In the same manner as described in Example 50B, Fmoc-Asp-OtBu (8.23 g, 20.0 mmol) was reacted with H-Gly-OBn.HCl (4.03 g, 20.0 mmol). Flash column chromatography on $SiO_2$, using an EtOAc/hexane gradient provided product (9.8 g, 88%) as a waxy solid: MS (FAB) 559; TLC (10% $MeOH/CHCl_3$) $R_f$=0.71;

$^1H$ NMR ($CDCl_3$, 300 MHz, ppm) 7.73 (d, 2H, J=7.5 Hz), 7.59 (d, 2H, J=7.4 Hz), 7.40–7.26 (m, 9H), 6.44 (br s, 1H), 6.09 (d, 1H, J=8.3 Hz), 5.13 (s, 2H), 4.52–4.49 (m, 1H), 4.41–4.29 (m, 2H), 4.21 (t, 1H, J=7.1 Hz), 4.04 (d, 2H, J=5.2 Hz), 2.95 (dd, 1H, J=4.6, 15.7 Hz), 2.79 (dd, 1H, J=4.3, 15.7 Hz), 1.46 (s, 9H).

B. The product of Example 51A (9.8 g, 17.54 mmol) was deprotected in the manner described in Example 50C. Filtration through a pad of $SiO_2$ with 100% EtOAc followed by 5% $MeOH/CHCl_3$ provided product (4.24 g, 72%) as an oil: MS (FAB) 337; TLC (3% MeOH/EtOAc) $R_f$=0.15; $^1H$ NMR ($CDCl_3$, 300 MHz, ppm) 8.00 (t, 1H, J=5.4 Hz), 7.30–7.21 (m, 5H), 5.07 (s, 2H), 3.98 (AB of ABX, 2H, J=5.4, 18.1 Hz), 3.60 (dd, 1H, J=3.4, 9.2 Hz), 2.60 (dd, 1H, J=3.4, 5.4 Hz), 2.38 (dd, 1H, J=9.2, 15.4 Hz), 1.79 (br s, 2H), 1.36 (s, 9H).

C. The product of Example 51B (4.24 g, 12.60 mmol) was cyclized in the manner described in Example 50D. Flash column chromatography using an $EtOAc/CHCl_3$gradient provided product as a syrup (1.4 g, 32%): MS (FAB) 349; TLC (1:1 $EtOAc/CHCl_3$) $R_f$=0.53; $^1H$ NMR ($CDCl_3$, 300 MHz, ppm) 7.35–7.25 (m, 5H), 5.11 (s, 2H), 4.21 (A of AB, 1H, J=17.5 Hz), 3.95 (B of AB, 1H, J=17.5 Hz), 3.71 (dd, 1H, J=5.1, 11.2 Hz), 2.68 (dd, 1H, J=5.1, 17.2 Hz), 2.36 (dd, 1H, J=11.2, 17.2 Hz), 1.43 (s, 9H).

D. The product of Example 51C (1.40 g, 4.02 mmol) was coupled with the product of Example 50A using the procedure of Example 50E. Flash column chromatography using a $CHCl_3$/EtOAc gradient provided product as a brittle, pale yellow foam (2.21 g, 76%): MS (FAB) 728; TLC (1:1 $CHCl_3$/EtOAc) $R_f$=0.28; $^1H$ NMR ($CDCl_3$, 300 MHz, ppm) consistent with structure and indicative of diastereomers.

E. The product of Example 51D (0.15 g, 0.21 mmol) was deprotected and purified as described in Example 50F. The product was obtained as an off-white solid (0.127 g, 90%): MS (FAB) 672 (M+H), 695 (M+Na); TLC (9:1:0.1 $CHCl_3$/MeOH/AcOH) Rf=0.54; $^1H$ NMR ($d^6$-DMSO, 300 MHz, ppm) consistent with structure and indicative of diastereomers.

Example 52

Compound 365

A. The product from Example 51E (0.100 g, 0.15 mmol), 4-methoxybenzylamine (20 μL, 0.15 mmol), and TBTU (0.0482 g, 0.15 mmol) in NMP (0.3 mL) were treated with $iPr_2NEt$ (78 μL, 0.45 mmol). After stirring overnight at RT, the reaction was diluted with EtOAc (10 mL), washed with $H_2O$ (5×2 mL), 5% citric acid (2×2 mL), 5% $NaHCO_3$ (2×2 mL) and brine (1×2 mL) and dried ($MgSO_4$). Filtration through a short pad of $SiO_2$, eluting with 2% $MeOH/CHCl_3$ followed by 4% $MeOH/CHCl_3$, provided product as a foam (0.087 g, 73%): MS (FAB) 792; TLC (9:1 $CHCl_3$/MeOH) $R_f$=0.41; $^1H$ NMR ($CDCl_3$, 300 MHz, ppm) consistent with structure and indicative of diastereomers.

B. A suspension of the product of Example 52A (0.087 g, 0.11 mmol) and Degussa type E101 NE/W 10% Pd/C (0.017 g) in MeOH (10 mL) was hydrogenated under 25 psi $H_2$ for 18 hr. The reaction was filtered through Celite, rinsing with MeOH. The filtrate was evaporated to dryness. The residue was triturated with $Et_2O$ and the resultant beige solids collected by filtration (36.1 mg, 47%): MS (FAB) 701 (M+H), 723 (M+Na); $^1H$ NMR ($d^6$-DMSO, 300 MHz, ppm) consistent with structure and indicative of diastereomers.

Example 53

Inhibition of VLA4-dependent Adhesion to BSA-CS1

This assay was used to assess the potency of VLA4-directed inhibitory compounds of this invention.

1. Conjugation of CS1 to BSA

We dissolved BSA-SMCC (Pierce Chemical, Rockford, Ill.; Catalog #77115) in $H_2O$ at a concentration of 10 mg/mL. [SEQ ID NO:4]: Cys-Tyr-Asp-Glu-Leu-Pro-Gln-Leu-Val-Thr-Leu-Pro-His-Pro-Asn-Leu-His-Gly-Pro-Glu-Ile-Leu-Asp-Val-Pro-Ser-Thr ("Cys-Tyr-CS1 peptide"), which we synthesized by conventional solid phase chemistry and purified by HPLC, was dissolved in 10 mM HEPES pH 5, 50 mM NaCl and 0.1 mM EDTA also at a concentration of 10 mg/mL. We then mixed 500 μL of BSA-SMCC, 250 μL of Cys-Tyr-CS1 peptide and 75 μL of 1 mM HEPES pH 7.5 and allowed the conjugation reaction to proceed for 30 minutes. We stopped the reaction by adding 1 μL of beta-mercaptoethanol. Samples were analyzed for cross-linking by SDS-PAGE. This reaction produced multiple molecules of the Cys-Tyr-CS1 peptide conjugate to each BSA molecule.

2. Preparation of Plates for Adhesion Assay

We coated the wells of a Linbro titertek polystyrene 96-well flat bottom plate (Flow Laboratories, Maclean, Va.; catalog #76-231-05) with 100 μL of the above-described BSA-CS1 solution diluted to 1 μg/mL in 0.05 M $NaHCO_3$ (15 mM $NaHCO_3$, 35 mM $Na_2CO_3$) pH 9.2. Some wells were not coated with CS1 in order to assess non-specific cell binding (NSB). The plate was then incubated overnight at 4° C.

Following this incubation, the contents of the wells were removed by inverting and blotting the plate. All of the wells were then blocked with 100 μL of 1% BSA in PBS, 0.02% $NaN_3$, for a minimum of one hour at room temperature.

3. Preparation of Fluorescently Labelled Ramos Cells

Ramos cells are grown, maintained and labelled in RPMI 1640 culture medium containing 1% BSA. Just prior to running the assay, we added 2',7'-bis-(2-carboxyethyl)-5 (and -6) carboxyfluorescein acetoxymethyl ester ("BCECF-AM"; Molecular Probes Inc., Eugene, Oreg.; catalog #B-1150) to a final concentration of 2 μM to a culture of Ramos cells (4×10⁶ cells/mL). We incubated the cells for 20 minutes at 37° C.

Following labelling, the cells were washed twice in assay buffer (24 mM TRIS, 137 mM NaCl, 2.7 mM KCl, pH 7.4, containing 0.1% BSA and 2 mM glucose) to remove any cations originating from the culture medium. The cells were then resuspended in assay buffer to 4×10⁶ cells/mL and 2 mM $MnCl_2$ was added to upregulate VLA4 on the surface of the cells.

4. Running the Assay

Immediately prior to running the assay, we removed the BSA blocking solution from the 96-well plates and washed the wells with 100 μL of assay buffer. We then added to each well 25 μL of test cell adhesion inhibitory compound at 2× the final concentration and 25 μL of the labelled Ramos cells. Final concentrations were selected across a range of anticipated IC50s, usually between 0.01 nM–10 μM. Each concentration of compound was tested in triplicate. The compound and cells are allowed to incubate for 30 minutes at room temperature.

We then emptied the contents of the plate and washed the wells 4 times with assay buffer. Using a light microscope, we examined the NSB wells. If more than a few cells are bound to those wells, we washed the plate once more to remove the excess non-specifically bound cells.

Binding of the Ramos cells to the CS1 peptide-coated wells was measured by adding 100 μL of assay buffer to each well and quantitating fluorescence in a Millipore Cytofluor 2300 System plate reader set at 485 nm excitation and 530 nm emission. Binding was expressed as an IC50—the concentration of inhibitor at which 50% of control binding occurs. Percent binding is calculated by the formula:

$$[(F_{TB}-F_{NS})-(F_I-F_{NS})]/[(F_{TB}-F_{NS})\times 100=\% \text{ binding,}$$

where $F_{TB}$ is total fluorescence bound to CS1-containing wells without added inhibitor; $F_{NS}$ is fluorescence bound in wells lacking CS1; and $F_I$ is fluorescence bound in wells containing an inhibitor of this invention.

Other compounds according to this invention were similarly assayed. The IC50 range for each of these compounds is indicated in the table below:

| Cmpd # | IC$_{50}$ |
|---|---|
| 1 | A |
| 2 | A |
| 3 | A |
| 4 | A |
| 5 | C |
| 6 | C |
| 7 | C |
| 8 | C |
| 9 | C |
| 10 | C |
| 11 | C |
| 12 | C |
| 13 | B |
| 14 | C |
| 15 | C |
| 16 | C |
| 17 | C |
| 18 | B |
| 19 | C |
| 20 | C |
| 21 | C |
| 22 | C |
| 23 | C |
| 24 | C |
| 25 | C |

-continued

| Cmpd # | IC$_{50}$ |
|---|---|
| 26 | C |
| 27 | C |
| 28 | C |
| 29 | C |
| 30 | C |
| 31 | C |
| 32 | C |
| 33 | C |
| 34 | B |
| 35 | B |
| 36 | C |
| 37 | C |
| 38 | C |
| 39 | C |
| 40 | C |
| 41 | B |
| 42 | B |
| 43 | B |
| 44 | B |
| 45 | C |
| 46 | C |
| 47 | C |
| 48 | C |
| 49 | C |
| 50 | C |
| 51 | C |
| 52 | C |
| 53 | C |
| 54 | C |
| 55 | C |
| 56 | B |
| 57 | B |
| 58 | B |
| 59 | B |
| 60 | C |
| 61 | B |
| 62 | C |
| 63 | C |
| 64 | C |
| 65 | C |
| 66 | C |
| 67 | C |
| 68 | C |
| 69 | C |
| 70 | C |
| 71 | C |
| 72 | C |
| 73 | C |
| 74 | C |
| 75 | C |
| 76 | C |
| 77 | C |
| 78 | C |
| 79 | C |
| 80 | C |
| 81 | C |
| 82 | C |
| 83 | C |
| 84 | C |
| 85 | C |
| 86 | C |
| 87 | C |
| 88 | C |
| 89 | C |
| 90 | C |
| 91 | C |
| 92 | C |
| 93 | C |
| 94 | C |
| 95 | C |
| 96 | C |
| 97 | C |
| 98 | C |
| 99 | C |
| 100 | C |
| 101 | C |
| 102 | C |

-continued

| Cmpd # | IC$_{50}$ |
|---|---|
| 103 | C |
| 104 | C |
| 105 | C |
| 106 | C |
| 107 | C |
| 108 | C |
| 109 | C |
| 110 | C |
| 111 | C |
| 112 | C |
| 113 | C |
| 114 | C |
| 115 | C |
| 116 | C |
| 117 | C |
| 118 | C |
| 119 | C |
| 120 | C |
| 121 | C |
| 122 | C |
| 123 | C |
| 124 | C |
| 125 | C |
| 126 | C |
| 127 | C |
| 128 | C |
| 129 | C |
| 130 | C |
| 131 | C |
| 132 | C |
| 133 | C |
| 134 | C |
| 135 | C |
| 136 | C |
| 137 | C |
| 138 | C |
| 139 | C |
| 140 | C |
| 141 | C |
| 142 | C |
| 143 | C |
| 144 | A |
| 145 | A |
| 146 | A |
| 147 | A |
| 148 | A |
| 149 | C |
| 150 | C |
| 151 | C |
| 152 | C |
| 153 | C |
| 154 | C |
| 155 | C |
| 156 | B |
| 157 | B |
| 158 | C |
| 159 | C |
| 160 | C |
| 161 | C |
| 162 | C |
| 163 | C |
| 164 | B |
| 165 | C |
| 166 | C |
| 167 | C |
| 168 | B |
| 169 | C |
| 170 | C |
| 171 | C |
| 172 | C |
| 173 | C |
| 174 | B |
| 175 | B |
| 176 | C |
| 177 | C |
| 178 | C |
| 179 | C |

-continued

| Cmpd # | IC$_{50}$ |
|---|---|
| 180 | B |
| 181 | C |
| 182 | C |
| 183 | C |
| 184 | C |
| 185 | C |
| 186 | C |
| 187 | C |
| 188 | C |
| 189 | C |
| 190 | C |
| 191 | C |
| 192 | B |
| 193 | C |
| 194 | nd |
| 195 | C |
| 196 | C |
| 197 | B |
| 198 | C |
| 199 | B |
| 200 | B |
| 201 | B |
| 202 | B |
| 203 | A |
| 204 | B |
| 205 | B |
| 206 | A |
| 207 | B |
| 208 | A |
| 209 | B |
| 210 | B |
| 211 | B |
| 212 | B |
| 213 | B |
| 214 | B |
| 215 | B |
| 216 | B |
| 217 | B |
| 218 | B |
| 219 | A |
| 220 | A |
| 221 | A |
| 222 | A |
| 223 | A |
| 224 | A |
| 225 | A |
| 226 | A |
| 227 | A |
| 228 | A |
| 229 | A |
| 230 | A |
| 231 | A |
| 232 | A |
| 233 | A |
| 234 | A |
| 235 | A |
| 236 | A |
| 237 | A |
| 238 | A |
| 239 | A |
| 240 | A |
| 241 | A |
| 242 | A |
| 243 | A |
| 244 | A |
| 245 | A |
| 246 | A |
| 247 | A |
| 248 | A |
| 249 | A |
| 250 | A |
| 251 | A |
| 252 | A |
| 253 | A |
| 254 | A |
| 255 | A |
| 256 | A |

-continued

| Cmpd # | IC$_{50}$ |
|---|---|
| 257 | A |
| 258 | A |
| 259 | A |
| 260 | A |
| 261 | A |
| 262 | A |
| 263 | A |
| 264 | A |
| 265 | A |
| 266 | A |
| 267 | A |
| 268 | A |
| 269 | A |
| 270 | A |
| 271 | A |
| 272 | A |
| 273 | A |
| 274 | A |
| 275 | A |
| 276 | A |
| 277 | A |
| 278 | A |
| 279 | A |
| 280 | A |
| 281 | A |
| 282 | A |
| 283 | A |
| 284 | A |
| 285 | A |
| 286 | A |
| 287 | A |
| 288 | A |
| 289 | A |
| 290 | A |
| 291 | A |
| 292 | A |
| 293 | A |
| 294 | A |
| 295 | A |
| 296 | A |
| 297 | A |
| 298 | A |
| 299 | A |
| 300 | A |
| 301 | A |
| 302 | A |
| 303 | A |
| 305 | A |
| 306 | A |
| 305 | A |
| 307 | A |
| 308 | A |
| 309 | A |
| 310 | A |
| 311 | A |
| 312 | A |
| 313 | A |
| 314 | A |
| 315 | A |
| 316 | A |
| 317 | A |
| 318 | A |
| 319 | B |
| 320 | B |
| 321 | B |
| 322 | A |
| 323 | B |
| 324 | B |
| 325 | B |
| 326 | A |
| 327 | A |
| 328 | A |
| 329 | A |
| 330 | C |
| 331 | C |
| 332 | C |
| 333 | C |

-continued

| Cmpd # | IC$_{50}$ |
|---|---|
| 334 | C |
| 335 | C |
| 336 | A |
| 337 | A |
| 338 | A |
| 339 | C |
| 340 | C |
| 341 | C |
| 342 | C |
| 343 | C |
| 344 | C |
| 345 | A |
| 346 | A |
| 347 | A |
| 348 | C |
| 349 | C |
| 350 | C |
| 351 | C |
| 352 | C |
| 353 | C |
| 354 | C |
| 355 | nd |
| 356 | nd |
| 357 | nd |
| 358 | A |
| 359 | A |
| 360 | C |
| 361 | C |
| 362 | C |
| 363 | C |
| 364 | B |
| 365 | B |
| 366 | C |
| 367 | C |
| 368 | C |
| 369 | C |
| 370 | C |
| 371 | B |
| 372 | C |
| 373 | C |
| 374 | C |
| 375 | B |
| 376 | C |
| 377 | nd |
| 378 | nd |
| 379 | nd |
| 380 | C |
| 381 | nd |
| 382 | nd |
| 383 | nd |
| 384 | nd |
| 385 | nd |
| 386 | C |
| 387 | C |
| 388 | nd |
| 389 | nd |
| 390 | C |
| 391 | C |
| 392 | nd |
| 393 | C |
| 394 | C |
| 395 | C |
| 396 | nd |
| 398 | C |
| 399 | nd |
| 400 | nd |
| 401 | nd |
| 402 | nd |
| 403 | C |
| 404 | C |
| 405 | C |
| 406 | C |
| 407 | C |
| 408 | C |
| 409 | B |
| 410 | B |
| 411 | A |

-continued

| Cmpd # | IC$_{50}$ |
|---|---|
| 412 | B |
| 413 | B |
| 414 | B |
| 415 | B |
| 416 | B |

Table abbreviations: A — <50 nm; B — 50 nm–10µm; C — >10 µm; nd — not determined. All compounds tested in this table demonstrated an IC$_{50}$ < 1 mM.

Example 54

Direct Binding of VLA4-Presenting Cells to VCAM-IgG

We next examined the ability of the compounds of this invention to inhibit VCAM/VLA4 binding, utilizing a VCAM-IgG-alkaline phosphatase conjugate. To carry out this assay, we used the Millipore Multiscreen Assay System (Millipore Corp., Bedford, Mass.) to wash the cells efficiently.

1. Preparation of VCAM-IgG-AP Conjugates

The construction of VCAM 2D-IgG expression vectors, transfection of CHO cells with those constructs and purification of the resulting expression product is described in PCT publication WO 90/13300, the disclosure of which is herein incorporated by reference.

1.2 ml of purified VCAM 2D-IgG (5 mg/ml in 10 mM HEPES, pH 7.5) was reacted with 44 µl of Traut's reagent (2-iminothiolane, 20 mg/ml in water; Pierce Chemical, Rockford, Ill.) at room temperature for 30 minutes. The sameple was desalted on a 15 ml Sephadex G-25 column equilibrated with 100 mM NaCl, 10 mM MES, pH 5.0. One ml fractions were collected and absorbance at 280 nm was determined. The two peak fractions were pooled.

One ml of calf intestinal alkaline phosphatase (19 mg/ml; Pierce Chemical, Rockford, Ill.) was reacted with 100 µl of sulfo-SMCC (30 mg/ml in water) and 100 µl 1 M HEPES, pH 7.5 for 35 minutes at room temperature. The reaction mix was desalted on a 12 ml Sephadex G-25 column equilibrated with 150 mM NaCl, 10 mM HEPES, pH 6.0. One ml fractions were collected and absorbance at 280 nm was determined. The two peak fractions were pooled and stored on ice.

The alkaline phosphatase-SMCC and VCAM 2D-IgG-iminothilane adducts were cross-linked at a molar ratio of 2:1 in Tris-HCL, pH 7.5 by incubation at room temperature for 30 minutes. Extent of cross-linking was determined by SDS-PAGE. The cross-linked products were stabilized by the addition of 2 mM MgCl$_2$ and 0.25 mM ZnCl$_2$ and stored at 4° C.

2. Binding Assay

We first blocked a 96-well filtration plate for by adding 275 µL of PBS containing 0.1% Tween 20 and 2% BSA ("blocking buffer") to each well and incubating for 1 hour at room temperature. The plate was then placed onto a vacuum manifold and the blocking buffer was drained through the bottom of the filtration wells into a waste collection tray. Then we washed the wells three times with 200–250 µL of Tris-buffered saline, containing 0.1% BSA, 2 mM glucose and 1 mM HEPES, pH 7.5 ("assay buffer") to wash out any remaining blocking buffer. We then drained the plates and blotted them on paper towels to remove buffer on the underside of the plate.

We then prepared a stock solution of VCAM-IgG-AP (4 µg/mL in assay buffer) and filtered it through a 0.2 µ low protein binding syringe filter (Gelman Sciences, Ann Arbor, Mich. #4454). This solution was then diluted 1:10 in assay buffer and 25 µL was added to every well of the washed plate.

We diluted the cell adhesion inhibitor being tested to 2× final concentration in assay buffer and added 25 µL of each dilution to triplicate wells in the plate. Final concentrations used ranged from 0.01 nM–10 µM. Control wells for total binding and non-specific binding received 25 µL of assay buffer, instead of inhibitor. Total binding wells contained cells and VCAM-IgG-AP in assay buffer. Non-specific binding wells contained only VCAM-IgG-AP in assay buffer.

Jurkat cells were washed once in assay buffer to remove growth medium and resuspended at 8×10$^6$/mL in assay buffer containing 2 mM MnCl$_2$. We added 50 µl of Jurkat cells to every well, except the non-specific binding wells, which received 50 µL of assay buffer to maintain a final assay volume of 100 µL per well. We gently mixed the contents of the wells by tapping the sides of the plate. The plate was then allowed to incubate undisturbed for 60 minutes at room temperature.

At the end of the 60 minute incubation, we placed the plate on the vacuum manifold to drain the wells. We carefully added 100 µL of assay buffer containing 1 mM MnCl$_2$ (wash buffer) to each well so as not to disturb the cells on the bottom. The wash buffer was removed by vacuum and the plate was washed again with 150 µL of wash buffer. After draining the wash buffer again, the underside of the plate was blotted on paper towels.

Next, we prepared a 10 mg/mL solution of 4-nitrophenylphosphate in 0.1 M glycine, 1 mM ZnCl$_2$, pH 10.5 (substrate buffer) and added 100 µL immediately added to each well. The plate was incubated for 30 minutes at room temperature to allow the calorimetric reaction to proceed. We stopped the reaction by adding 100 µL of 3 N NaOH to each well.

The contents of the 96-well filtration plate was then transferred directly into a 96-well flat bottom plate using the vacuum manifold. The plate was read at a wavelength of 405 nm to determine the amount of VCAM conjugate bound to the cells. Percent binding is calculated by the formula:

$$[(A_{TB}-A_{NS})-(A^I-A_{NS})]/[(A_{TB}-A_{NS})\times 100=\% \text{ binding},$$

where $A_{TB}$ is the absorbance at 405 nm of CS1-containing wells without added inhibitor; $A_{NS}$ is the absorbance at 405 nm in wells lacking CS1; and $A_I$ is absorbance at 405 nm in wells containing an inhibitor of this invention We assayed other compounds of this invention in the same assay. The IC50 values are comparable to those derived from the CS1 binding assay described in the previous example, although certain compounds demonstrated up to 10-fold greater binding in this assay than in the previous assay.

Example 55

Inhibition of Mouse Contact Hypersensitivity

We anesthetized 20-g female Balb/c mice (Jackson Laboratories, Bar Harbor, Me.) with sodium pentobarbital (90 mg/kg, i.p.). A 3 cm$^2$ patch of abdominal skin was then exposed by closely shaving the fur. The skin was then scrubbed with 70% ethanol, followed by application of 25 µL of 0.5% DNFB in 4:1 v/v acetone:olive oil onto the bare abdominal skin. We then lightly scratched the skin with the applying pipet tip to encourage mild inflammation. Twenty four hours after the initial sensitization we again sensitized the mouse with 25 µL of 0.5% DNFB at same abdominal skin location, again followed by light scratching with the pipet tip. The second sensitization was performed while restraining the unanesthetized mouse.

On Day 5 (120 hours after the initial sensitization), we anesthetized the mice with 90:10 mg/kg ketamine:xylazine, i.p. and applied a sub-irritant dose of 10 μL of 0.2% DNFB to the dorsal surface of the left ear. The right ear received a similar application of the 4:1 v/v acetone:olive oil vehicle.

Four hours after challenging the immune response, we administered various concentrations of the inhibitors of this invention to the mice in 100 μL 0.5% sodium phosphate buffer, pH 8.8, and 3% v/v DMSO by subcutaneous (s.c.) injection. Less soluble inhibitors occasionally required up to 30% DMSO addition the highest concentrations tested. Groups of 8 mice were used for each treatment tested. Positive (PS2 anti-mouse VLA-4 antibody, 8 mg/kg, i.v.), and negative control (phosphate-buffered physiological saline, PBS, 100 μL i.v.; DMSO in PBS, 100 μL s.c.) groups were routinely tested for comparison as part of the assay of test compounds.

Twenty four hours after challenge mice were again anesthetized with ketamine:xylazine and the ear thickness of both ears measured with an engineer's micrometer to an accuracy of $10^{-4}$ inches. The ear swelling response for each mouse was the difference between its control- and DNFB-challenged ear thickness. Typical uninhibited ear swelling responses were 65–75×10−4 in. Inhibition of the ear swelling response was judged by comparison of treated groups with their negative control group. Percent inhibition was calculated as:

$$\left[ \frac{\text{(mean negative control group ear swelling)} - \text{(mean test group ear swelling)}}{\text{mean negative control group ear swelling}} \times 100 \right]$$

Statistical significance of the difference among treatment groups was evaluated using one-way analysis of variance followed by computation of the Tukey-Kramer Honestly Significant Difference (JMP, SAS Institute) using $p<0.05$.

The inhibitors of this invention cause a statistically significant reduction in the ear swelling response of DNFB-treated mice as compared to uninhibited control animals.

Example 56

Inhibition of Ascaris Antigen-induced Late Phase Airway Sensitivity in Allergic Sheep Sheep which had previously been shown to develop both early and late bronchial responses to *Ascaris suum* antigen were used in this study. The protocol used for the experiment was that described in W. M. Abraham et al., *J. Clin. Invest.*, 93, pp. 776–87 (1994), except that the VLA-4 inhibitors of this invention were administered to the animals was dissolved in 3–4 ml of 50% aqueous ethanol and delivered by aerosol spray.

The results showed that all of the VLA-4 inhibitors of this invention inhibited the airway responses associated with administration of *Ascaris suum* antigen.

While we have hereinbefore presented a number of embodiments of this invention, it is apparent that our basic construction can be altered to provide other compounds and methods which utilize the compounds of this invention. Therefore, it will be appreciated that the scope of this invention is to be defined by the claims appended hereto rather than the specific embodiments which have been presented hereinbefore by way of example.

We claim:

1. A cell adhesion inhibitory compound of formula (I),

$$Z-(Y^1)-(Y^2)-(Y^3)_n-X \qquad (I)$$

or a pharmaceutically acceptable derivative thereof, wherein:

Z is selected from the group consisting of aliphatic acyl substituted with N-arylamido; heterocycloyl; substituted aralkylcarbonyl; heterocycloalkylcarbonyl; cycloalkylcarbonyl optionally fused with aryl; heterocycloalkoxycarbonyl; alkylaminocarbonyl; arylaminocarbonyl optionally substituted with bis(alkylsulfonyl)amino, alkoxycarbonylamino or alkenyl; aralkylaminocarbonyl optionally substituted with bis(alkylsulfonyl)amino, alkoxycarbonylamino or alkenyl; alkylsulfonyl; aralkylsulfonyl; arylsulfonyl; cycloalkylsulfonyl optionally fused with aryl; heterocyclylsulfonyl; heterocyclylalkylsulfonyl; aryloxycarbonyl; cycloalkyloxycarbonyl; heterocyclyloxycarbonyl; heterocyclylalkoxycarbonyl; mono or di-alkylaminocarbonyl optionally substituted with aryl; (alkyl)(aralkyl)aminocarbonyl; mono- or di-aralkylaminocarbonyl; mono- or di-arylaminocarbonyl; (aryl)(alkyl)aminocarbonyl; mono- or di-cycloalkylaminocarbonyl; heterocyclylaminocarbonyl; heterocyclylalkylaminocarbonyl; (alkyl)(heterocyclyl)aminocarbonyl; (alkyl)(heterocyclylalkyl)aminocarbonyl; (aralkyl)(heterocyclyl)aminocarbonyl; (aralkyl)(heterocyclylalkyl)aminocarbonyl; alkenoyl optionally substituted with aryl; alkenylsulfonyl optionally substituted with aryl; alkynoyl optionally substituted with aryl; alkynylsulfonyl optionally substituted with aryl; cycloalkenylcarbonyl; cycloalkenylsulfonyl; cycloalkylalkylsulfonyl; arylaroyl; biarylsulfonyl; alkoxysulfonyl; aralkoxysulfonyl; alkylaminosulfonyl; aryloxysulfonyl; arylaminosulfonyl; N-arylurea-substituted alkanoyl; N-arylurea-substituted alkylsulfonyl; cycloalkenyl-substituted carbonyl; cycloalkenyl-substituted sulfonyl; alkenoxycarbonyl optionally substituted with aryl; alkenoxysulfonyl optionally substituted with aryl; alkynoxycarbonyl optionally substituted with aryl; alkynoxysulfonyl optionally substituted with aryl; alkynylaminocarbonyl optionally substituted with aryl; alkenylaminocarbonyl optionally substituted with aryl; alkenylaminosulfonyl optionally substituted with aryl; alkynylaminosulfonyl optionally substituted with aryl; acylamino-substituted alkanoyl; acylamino-substituted alkylsulfonyl; aminocarbonyl-substituted alkanoyl; carbamoyl-substituted alkanoyl; carbamoyl-substituted alkylsulfonyl; heterocyclylaminosulfonyl; carboxyalkyl-substituted aralkoyl; carboxyalkyl-substituted aralkylsulfonyl; oxocarbocyclyl-fused aroyl; oxocarbocyclyl fused arylsulfonyl; heterocyclylalkanoyl; N',N'-alkyl arylhydrazinocarbonyl; aryloxy-substituted alkanoyl; and heterocyclylalkylsulfonyl;

$Y^1$ is —N($R^1$)—C($R^2$)($A^1$)—C(O)—;

$Y^2$ is —N($R^1$)—C($R^2$)($A^2$)—C(O)—;

each $Y^3$ is represented by the formula —N($R^1$)—C($R^2$)($A^3$)—C(O)—;

$A^1$ is selected from the group consisting of
- amino acid side chains and corresponding protected derivatives,
- cycloalkyl, and
- alkyl optionally substituted with amino, acylamino, amino-substituted acylamino, alkoxycarbonylamino, aryl, cycloalkyl, carboxy, alkoxy, aralkyloxy, alkoxycarbonyl, aralkoxycarbonyl, aminocarbonyl, alkylaminocarbonyl, dialkylaminocarbonyl, (alkyl)(aralkyl)aminocarbonyl, aralkylaminocarbonyl, diaralkylaminocarbonyl, hydroxyl, carboxyalkylaminocarbonyl, hydroxylaminocarbonyl, mercapto, thioalkoxy or heterocycyl;

$A^2$ is selected from the group consisting of acidic functional groups and alkyl optionally substituted with an acidic functional group, a protected acidic functional group or aryl;

each $A^3$, independently, is selected from the group consisting of
- amino acid side chains and corresponding protected derivatives,
- aryl,
- cycloalkyl, and
- alkyl optionally substituted with amino, acylamino, amino substituted acylamino, aryl, cycloalkyl, carboxy, alkoxy, aralkyloxy, alkoxycarbonyl, aralkoxycarbonyl, aminocarbonyl, alkylaminocarbonyl, dialkylaminocarbonyl, (alkyl)(aralkyl)aminocarbonyl, aralkylaminocarbonyl, diaralkylaminocarbonyl, hydroxyl, carboxyalkylaminocarbonyl, hydroxylaminocarbonyl, mercapto, thioalkoxy or heterocycle;

each $R^1$, independently, is selected from the group consisting of hydrogen, alkyl, aralkyl, alkenyl, alkynyl, cycloalkyl, cycloalkenyl, cycloalkylalkyl, aryl, aminoalkyl, mono or di-alkyl-substituted aminoalkyl, mono- or di-aralkyl-substituted aminoalkyl, hydroxyalkyl, alkoxyalkyl, mercaptoalkyl, and thioalkoxyalkyl;

or $R^1$ and any A are taken together with the atoms to which they are attached form a 3- to 6- membered ring heterocycle;

each $R^2$, independently, is selected from the group consisting of hydrogen and alkyl;

n is an integer from 0 to 8; and

X is selected from the group consisting of
- alkoxy,
- aryloxy,
- aralkyloxy,
- hydroxyl,
- amino,
- alkylamino optionally substituted with hydroxy, aminocarbonyl, N-alkylaminocarbonyl, carboxy or alkoxycarbonyl,
- dialkylamino,
- cycloalkylamino,
- dicycloalkylamino,
- cycloalkylalkylamino,
- (alkyl)(aryl)amino,
- aralkylamino optionally substituted with carboxy,
- diaralkylamino,
- arylamino,
- heterocycle,
- (mono- or bis-carboxylic acid)-substituted alkylamine,
- heterocyclylamino, and
- heterocyclyl-substituted alkylamino;

provided that the compound of formula I is expressly not N-carboxymethyl-N-(phenylacetyl-L-leucyl-L-aspartyl-L phenylalanyl-L-prolyl)piperazine and expressly not phenylacetyl L leucyl-L-aspartyl-L-phenylalanyl-D-proline amide; and provided that Z is not pyridylcarbonyl, pyridylacetyl, phthalimido, 3-quinolinoyl, pyrazolylcarbonyl, or 2-pyrazinylcarbonyl, when $Y^2$ is D, $Y^3$ is V, I, F, P, W, Y, or L, and n is 1; and also provided that Z is not pyridylcarbonyl, pyridylacetyl, phthalimido, 3-quinolinoyl, pyrazolylcarbonyl, or 2-pyrazinylcarbonyl, when both $Y^2$ is D and n is 0.

2. The cell adhesion inhibitory compound according to claim 1, wherein:

Z is selected from the group consisting of
- aliphatic acyl substituted with N-arylamido,
- heterocycloyl,
- arylsulfonyl,
- alkylsulfonyl,
- substituted aralkylcarbonyl,
- heterocycloalkylcarbonyl,
- cycloalkylcarbonyl optionally fused with aryl,
- heterocycloalkoxycarbonyl,
- alkylaminocarbonyl,
- arylaminocarbonyl optionally substituted with bis(alkylsulfonyl)amino, alkoxycarbonylamino, or alkenyl, and
- aralkylaminocarbonyl optionally substituted with bis-(alkylsulfonyl)amino, alkoxycarbonylamino, or alkenyl;

each $R^1$, independently, is selected from the group consisting of hydrogen, alkyl, and aralkyl; and X is selected from the group consisting of
- alkoxy,
- aryloxy,
- aralkyloxy,
- hydroxyl,
- amino,
- alkylamino optionally substituted with hydroxy, aminocarbonyl, N-alkylaminocarbonyl, carboxy or alkoxycarbonyl,
- dialkylamino,
- cycloalkylamino,
- dicycloalkylamino,
- cycloalkylalkylamino,
- (alkyl)(aryl)amino,
- aralkylamino optionally substituted with carboxy,
- diaralkylamino,
- arylamino,
- heterocycle, and
- (mono- or bis-carboxylic acid)-substituted alkylamine.

3. The cell adhesion inhibitory compound according to claim 1, wherein $A^1$ is cycloalkyl, alkyl optionally substituted with amino, acylamino, amino-substituted acylamino, aryl, carboxy, cycloalkyl, hydroxy, alkoxy, aralkyloxy, alkoxycarbonyl, aralkoxycarbonyl, aminocarbonyl, alkylaminocarbonyl, dialkylaminocarbonyl, (alkyl)(aralkyl) aminocarbonyl, aralkylaminocarbonyl, diaralkylaminocarbonyl, alkoxycarbonylamino, mercapto, thioalkoxy, heterocycle, or A¹ and R¹ taken together with atoms to which they are attached form a heterocycle.

4. The cell adhesion inhibitory compound according to claim 3, wherein A¹ is aminocarbonylethyl, benzyl, n-butyl, isobutyl, carboxyethyl, cyclohexyl, 1-hydroxyethyl, hydroxymethyl, mercaptomethyl, 1-methylpropyl, methylthioethyl, n-propyl, isopropyl, methoxycarbonylaminobutyl, 6-aminohexanoylaminobutyl, or A¹ and R¹ taken together with atoms to which they are attached form an azetidine, aziridine, pyrrolidine, or piperidine.

5. The cell adhesion inhibitory compound according to claim 4, wherein A¹ is selected from the group consisting of benzyl, n-butyl, isobutyl, methylthioethyl, cyclohexyl, 1-methylpropyl, n-propyl and isopropyl.

6. The cell adhesion inhibitory compound according to claim 4, wherein A¹ and R¹ taken together with atoms to which they are attached form a pyrrolidine.

7. The cell adhesion inhibitory compound according to claim 1, wherein A² is
  alkyl optionally substituted with amino, aminocarbonyl, aryl, alkoxycarbonyl, aralkyloxycarbonyl, hydroxylaminocarbonyl, carboxy, NH-containing heterocycle, hydroxy, mercapto,
  aralkyl optionally substituted with amino, aminocarbonyl, carboxy, NH-containing heterocycle, hydroxy, mercapto, or
  A² and R¹ taken together with atoms to which they are attached form a heterocycle.

8. The cell adhesion inhibitory compound according to claim 7 wherein A² is carboxymethyl, 2-carboxyethyl, 1-carboxyethyl, hydroxylaminocarbonylmethyl, hydroxymethyl, mercaptomethyl, imidazolylmethyl, N-Bn-imidazolylmethyl, phenyl, carbomethoxymethyl, carbobenzyloxymethyl, or A² and R¹ taken together with atoms to which they are attached form an azetidine, aziridine, pyrrolidine or piperidine.

9. The cell adhesion inhibitory compound according to claim 8 wherein A² is selected from the group consisting of carboxymethyl, 2-carboxyethyl, 1-carboxyethyl, hydroxylaminocarbonylmethyl, hydroxymethyl, mercaptomethyl and imidazolylmethyl.

10. The cell adhesion inhibitory compound according to claim 1, wherein each A³, independently, is selected from the group consisting of amino acid side chains and corresponding protected derivatives,
  cycloalkyl, and
  alkyl optionally substituted with aryl, cycloalkyl, carboxy, hydroxylaminocarbonyl, alkoxy, aralkyloxy, mercapto, N-containing heterocycle, carboxyalkylaminocarbonyl or amino-substituted acylamino group.

11. The cell adhesion inhibitory compound according to claim 10, wherein each A³, independently, is selected from the group consisting of
  amino acid side chains and corresponding protected derivatives,
  cyclohexyl, and
  alkyl optionally substituted with phenyl, cyclohexyl, carboxy, hydroxylaminocarbonyl, methoxy, benzyloxy, mercapto, N-benzylimidazolyl, biotinyl, tetrazolyl, valinyl-N-carbonyl or 6-aminohexanoylamino.

12. The cell adhesion inhibitory compound according to claim 1, wherein each Y³, independently, is selected from the group consisting of amino acids and corresponding protected derivatives of the amino acid.

13. The cell adhesion inhibitory compound according to claim 1, wherein:

n is 2;
Y¹ is leucinyl;
Y² is aspartyl; and
Y³ is valinylprolinyl.

14. The cell adhesion inhibitory compound according to claim 1, wherein X is selected from the group consisting of
  alkoxy,
  aryloxy,
  aralkyloxy,
  hydroxyl,
  amino,
  mono- and dialkylamino optionally substituted with hydroxy, aminocarbonyl, N-alkylaminocarbonyl, carboxy or alkoxycarbonyl,
  dialkylamino,
  cycloalkylamino,
  cycloalkylalkylamino,
  dicycloalkylamino,
  (alkyl)(aryl)amino,
  aralkylamino optionally substituted with carboxy,
  diaralkylamino,
  arylamino,
  N-containing heterocycle,
  bis-carboxylic acid substituted alkylamine, and
  (mono- or bis-carboxy)methylaminocarbonyl-substituted-N-containing heterocycle.

15. The cell adhesion inhibitory compound according to claim 14, wherein X is selected from the group consisting of amino, methylamino, isopropylamino, isobutylamino, n-butylamino, t-butylamino, isoamyl, isopentylamino, hexylamino, cyclohexylamino, cyclohexylmethylamino, methylphenylamino, phenylmethylamino, phenylamino, 4-methoxyphenylmethylamino, dimethylamino, diisopropylanino, diisobutylamino, hydroxy, methoxy, n-butoxy, t-butoxy, benzyloxy, 2-piperidinecarboxylic acid, N'-(α,α'-bis-carboxymethyl)-2-piperidinecarboxamide, N'-carboxymethyl-2-piperidinecarboxamide, 1-hydroxymethyl-2-methylpropylamino, 1-N'-methylamido-1-methylethylamino, 3,3-dimethylbutylamino, 1-N'-methylamidobutylamino, 1-amido-2-methylbutylamino, 1-carbomethoxy-2-methylbutylamino, 1-N'-methylamido-2-methylbutylamino, 1-carboxy-1-phenylmethylamino, morpholino, piperidinyl, N-phenylpiperazinyl, pipecolinyl, and piperazinyl.

16. The cell adhesion inhibitory compound according to claim 1, wherein Z is selected from the group consisting of aliphatic acyl substituted with N-arylamido, substituted aralkylcarbonyl, heterocycloyl, and heterocycloalkylcarbonyl.

17. The cell adhesion inhibitory compound according to claim 2 selected from the group consisting of
  compound 1 (L-Proline, 1-[N-[N-[N-[[4-[[phenylamino]carbonyl]amino](3-methoxyphenyl)]acetyl]-L-leucyl]-L-α-aspartyl]-L-valyl]-),
  compound 2 (L-Proline, 1-[N-[N-[N-[[4-[[phenylamino]carbonyl]amino](3-methoxyphenyl))acetyl]-L-methionyl]-L-α-aspartyl]-L-valyl]-),
  compound 144 (L-Proline, 1-[N-[N-[N-[[4-[[(2-hydroxy)phenylamino]carbonyl]amino]phenyl]acetyl]-L-leucyl]-L-α-aspartyl]-L-valyl]-),
  compound 145 (L-Proline, 1-[N-[N-[N-[[4-[[phenylamino]carbonyl]amino]phenyl]acetyl]-L-leucyl]-L-α-aspartyl]-L-valyl]-), compound 146 (L-Proline, 1-[N-[N-[N-[[4-[[(2-hydroxy)phenylamino]carbonyl]amino]phenyl]acetyl]-L-methionyl]-L-α-aspartyl]-L-valyl]-), compound 147 (L-Prolinamide, 1-[N-[N-[N-[[4-[[phenylamino]carbonyl]amino](3-methoxyphenyl)]acetyl]-L-leucyl]-L-α-aspartyl]-L-valyl]-), compound 148 (L-Prolinamide, 1-[N-[N-[N-[[4-[[(2-methylphenyl)amino]carbonyl]amino]phenyl]acetyl]-L-leucyl]-L-α-aspartyl]-L-valyl]-), compound 206 (L-Proline, 1-[N-[N-[N-[[4-[[(2-methylphenyl)amino]carbonyl]amino]phenyl]acetyl]-L-leucyl]-L-α-aspartyl]-L-valyl]-), compound 315 (L-Proline, 1-[N-[N-[N-[[4-[[(2-methylphenyl)amino]carbonyl]amino]phenyl]acetyl]-L-methionyl]-L-α-aspartyl]-L-valyl]-), compound 316 (L-Proline, 1-[N-[N-[N-[[4-[[2-pyridylamino]carbonyl]amino]phenyl]acetyl]-L-leucyl]-L-α-aspartyl]-L-valyl]-), compound 317 (L-Prolinamide, 1-[N-[N-[N-[[4-[[(2-methylphenyl)amino]carbonyl]amino](3-methoxyphenyl)]acetyl]-L-leucyl]-L-α-aspartyl]-L-valyl]-), compound 337 (L-Serine, 1-[N-[N-[N-[N-[[4-[[(2-methylphenyl)amino]carbonyl]amino]phenyl]acetyl]-L-leucyl]-L-α-aspartyl]-L-valyl]-L-prolyl]-), compound 338 (L-Threonine, 1-[N-[N-[N-[N-[N-[[4-[[(2-methylphenyl)amino]carbonyl]amino]phenyl]acetyl]-L-leucyl]-L-α-aspartyl]-L-valyl]-L-prolyl]-L-seryl]-), compound 345 (L-Valine, 1-[N-[N-[[4-[[(2-methylphenyl)amino]carbonyl]amino]phenyl]acetyl]-L-leucyl]-L-α-aspartyl]-), compound 346 (L-Proline, 1-[N-[N-[N-[[4-[[(6-methyl-2-pyridyl)amino]carbonyl]amino]phenyl]acetyl]-L-leucyl]-L-α-aspartyl]-L-valyl]-), compound 347 (L-Proline, 1-[N-[N-[N-[[4-[[(2-fluorophenyl)amino]carbonyl]amino]phenyl]acetyl]-L-leucyl]-L-α-aspartyl]-L-valyl]-), compound 357 (L-Prolinamide, 1-[N-[N-[N-[[4-[[(2-pyridyl)amino]carbonyl]amino]phenyl]acetyl]-L-leucyl]-L-α-aspartyl]-L-valyl]-), compound 358 (L-Proline, 1-[N-[N-[N-[[4-[[(2-methylphenyl)amino]carbonyl]amino]phenyl]acetyl]-L-leucyl]-L-α-aspartyl]-L-valyl]-, compound with 2 equivalents of 2-amino-2-(hydroxymethyl)-1,3-propanediol), and compound 359 (L-Proline, 1-[N-[N-[N-[[4-[[(2-methylphenyl)amino]carbonyl]amino]phenyl]acetyl]-L-leucyl]-L-α-aspartyl]-L-valyl]-, disodium salt).

18. The cell adhesion inhibitory compound according to claim 17 selected from the group consisting of compound 1 (L-Proline, 1-[N-[N-[N-[[4-[[phenylamino]carbonyl]amino](3-methoxyphenyl)]acetyl]-L-leucyl]-L-α-aspartyl]-L-valyl]-), compound 206 (L-Proline, 1-[N-[N-[N-[[4-[[(2-methylphenyl)ammo]carbonyl]amino]phenyl]acetyl]-L-leucyl]-L-α-aspartyl]-L-valyl]-), compound 316 (L-Proline, 1-[N-[N-[N-[[2-pyridylamino]carbonyl]amino]phenyl]acetyl]-L-leucyl]-L-α-aspartyl]-L-valyl]-), compound 358 (L-Proline, 1-[N-[N-[N-[[4-[[(2-methylphenyl)amino]carbonyl]amino]phenyl]acetyl]-L-leucyl]-L-α-aspartyl]-L-valyl]-, compound with 2 equivalents of 2-amino-2-(hydroxymethyl)-1,3-propanediol), and compound 359 (L-Proline, 1-[N-[N-[N-[[4-[[(2-methylphenyl)amino]carbonyl]amino]phenyl]acetyl]-L-leucyl]-L-α-aspartyl]-L-valyl]-, disodium salt).

19. The cell adhesion inhibitory compound according to claim 18 is compound 358 (L-Proline, 1-[N-[N-[N-[[4-[[(2-methylphenyl)amino]carbonyl]amino]phenyl]acetyl]-L-leucyl]-L-α-aspartyl]-L-valyl]-, compound 358 with 2 equivalents of 2-amino-2-(hydroxymethyl)-1,3-propanediol).

20. A pharmaceutical composition comprising a compound according to claim 1 in an amount effective for prevention, inhibition or suppression of cell adhesion and a pharmaceutically acceptable carrier.

21. The pharmaceutical composition according to claim 20, further comprising an agent selected from the group consisting of corticosteroids, bronchodilators, antiasthmatics, antiinflammatories, antirheumatics, immunosuppressants, antimetabolites, immunomodulators, antipsoriatics, and antidiabetics.

22. A cell adhesion inhibitory compound of formula (I),

or a pharmaceutically acceptable derivative thereof; wherein:

Z is a (N—Ar'-urea)-para-substituted aralkylcarbonyl group;

$Y^1$ is —N($R^1$)—C($R^2$)($A^1$)—C(O)—;

$Y^2$ is —N($R^1$)—C($R^2$)($A^2$)—C(O)—;

each $Y^3$ is represented by the formula —N($R^1$)—C($R^2$)($A^3$)—C(O)—;

$A^1$ is selected from the group consisting of
  amino acid side chains and corresponding protected derivatives,
  cycloalkyl, and
  alkyl optionally substituted with amino, acylamino, amino substituted acylamino, alkoxycarbonylamino, aryl, cycloalkyl, carboxy, alkoxy, aralkyloxy, alkoxycarbonyl, aralkoxycarbonyl, aminocarbonyl, alkylaminocarbonyl, dialkylaminocarbonyl, (alkyl)(aralkyl)aminocarbonyl, aralkylaminocarbonyl, diaralkylaminocarbonyl, hydroxyl, carboxyalkylaminocarbonyl, hydroxylaminocarbonyl, mercapto, thioalkoxy or heterocycle;

$A^2$ is selected from the group consisting of
  acidic functional groups, and
  alkyl optionally substituted with an acidic functional group, protected acidic functional group or aryl;

each $A^3$, independently, is selected from the group consisting of
  amino acid side chains and corresponding protected derivatives,
  aryl,
  cycloalkyl, and
  alkyl optionally substituted with amino, acylamino, amino-substituted acylamino, aryl, cycloalkyl, carboxy, alkoxy, aralkyloxy, alkoxycarbonyl, aralkoxycarbonyl, aminocarbonyl, alkylaminocarbonyl, dialkylaminocarbonyl, (alkyl)(aralkyl)aminocarbonyl, aralkylaminocarbonyl, diaralkylaminocarbonyl, hydroxyl, carboxyalkylaminocarbonyl, hydroxylaminocarbonyl, mercapto, thioalkoxy or heterocycle;

each $R^1$, independently, is selected from the group consisting of hydrogen, alkyl, aralkyl, alkenyl, alkynyl, cycloalkyl, cycloalkenyl, cycloalkylalkyl, aryl, aminoalkyl, mono- or di-alkyl substituted aminoalkyl, mono- or di-aralkyl-substituted aminoalkyl, hydroxyalkyl, alkoxyalkyl, mercaptoalkyl; and thioalkoxyalkyl, or $R^1$ and any A taken together with the atoms to which they are attached form a 3- to 6-membered ring heterocycle;

each $R^2$ independently, is selected from the group consisting of hydrogen and alkyl;

n is an integer from 0 to 8; and

X is selected from the group consisting of
alkoxy,
aryloxy,
aralkyloxy,
hydroxyl,
amino,
alkylamino optionally substituted with hydroxy, aminocarbonyl, N-alkylaminocarbonyl, carboxy or alkoxycarbonyl,
dialkylamino,
cycloalkylamino,
dicycloalkylamino,
cycloalkylalkylamino,
(alkyl)(aryl)amino,
aralkylamino optionally substituted with carboxy,
diaralkylamino,
arylamino,
heterocycle,
(mono or bis-carboxylic acid)substituted alkylamine,
heterocyclylamino, and
heterocyclyl-substituted alkylamino.

23. The cell adhesion inhibitory compound according to claim 22, wherein each $Y^3$ is independently selected from the group consisting of amino acids and corresponding protected derivatives of the amino acids.

24. The cell adhesion inhibitory compound according to claim 22, wherein:
$Y^1$ is leucinyl;
$Y^2$ is aspartyl; and
$Y^3$ is valinylprolinyl.

25. The cell adhesion inhibitory compound according to claim 22, wherein Z is a (N—Ar'-urea)-para-substituted-phenylmethylcarbonyl.

26. The cell adhesion inhibitory compound according to claim 22, wherein:
Z is a (N—Ar'-urea)-para-substituted aralkylcarbonyl group;
each $R^1$, independently, is selected from the group consisting of hydrogen, alkyl, and aralkyl; and
X is selected from the group consisting of
alkoxy,
aryloxy,
aralkyloxy,
hydroxyl,
amino,
alkylamino optionally substituted with hydroxy, aminocarbonyl, N-alkylaminocarbonyl, carboxy or alkoxycarbonyl,
dialkylamino,
cycloalkylamino,
dicycloalkylamino,
cycloalkylalkylamino,
(alkyl)(aryl)amino,
aralkylamino optionally substituted with carboxy,
diaralkylamino,
arylamino,
heterocycle, and
(mono- or bis-carboxylic acid)-substituted alkylamine.

27. The cell adhesion inhibitory compound according to claim 22, wherein $A^1$ is
cycloalkyl,
alkyl optionally substituted with amino, acylamino, amino-substituted acylamino, aryl, carboxy, cycloalkyl, hydroxy, alkoxy, aralkyloxy, alkoxycarbonyl, aralkoxycarbonyl, aminocarbonyl, alkylaminocarbonyl, dialkylaminocarbonyl, (alkyl)(aralkyl)aminocarbonyl, aralkylaminocarbonyl, diaralkylaminocarbonyl, alkoxycarbonylamino, mercapto, thioalkoxy, or heterocycle,
or A and R' taken together with atoms to which they are attached form a heterocycle.

28. The cell adhesion inhibitory compound according to claim 27, wherein $A^1$ is aminocarbonylethyl benzyl, n-butyl, isobutyl, carboxyethyl, cyclohexyl, 1-hydroxyethyl, hydroxymethyl, mercaptomethyl, 1-methylpropyl, methylthioethyl, n-propyl, isopropyl, methoxycarbonylaminobutyl, 6-aminohexanoylaminobutyl, or $A^1$ and $R^1$ taken together with atoms to which they are attached form an azetidine, aziridine, pyrrolidine, or piperidine.

29. The cell adhesion inhibitory compound according to claim 28, wherein $A^1$ is selected from the group consisting of benzyl, n-butyl, isobutyl, methylthioethyl, cyclohexyl, 1-methylpropyl, n-propyl, and isopropyl.

30. The cell adhesion inhibitory compound according to claim 28, wherein $A^1$ and $R^1$ taken together with atoms to which they are attached form a pyrrolidine.

31. The cell adhesion inhibitory compound according to claim 22, wherein $A^2$ is alkyl optionally substituted with amino, aminocarbonyl, aryl, alkoxycarbonyl, aralkyloxycarbonyl, hydroxylaminocarbonyl, carboxy, NH-containing heterocycle, hydroxy, mercapto, aralkyl optionally substituted with amino, aminocarbonyl, carboxy, NH-containing heterocycle, hydroxy, mercapto, or $A^2$ and $R^1$ taken together with atoms to which they are attached form a heterocycle.

32. The cell adhesion inhibitory compound according to claim 31, wherein $A^2$ is carboxymethyl, 2-carboxyethyl, 1-carboxyethyl, hydroxylaminocarbonylmethyl, hydroxymethyl, mercaptomethyl, imidazolylmethyl, N-Bn-imidazolylmethyl, phenyl, carbomethoxymethyl, carbobenzyloxymethyl, or $A^2$ and $R^1$ taken together with atoms to which they are attached form an azetidine, aziridine, pyrrolidine or piperidine.

33. The cell adhesion inhibitory compound according to claim 32, wherein $A^2$ is selected from the group consisting of carboxymethyl, 2-carboxyethyl, 1-carboxyethyl, hydroxylaminocarbonylmethyl, hydroxymethyl, mercaptomethyl, and imidazolylmethyl.

34. The cell adhesion inhibitory compound according to claim 22, wherein $A^3$ is, independently, selected from the group consisting of amino acid side chains and corresponding protected derivatives; cycloalkyl; and alkyl optionally substituted with aryl, cycloalkyl, carboxy, hydroxylaminocarbonyl, alkoxy, aralkyloxy, mercapto, N-containing heterocycle, carboxyalkylaminocarbonyl, or amino-substituted acylamino group.

35. The cell adhesion inhibitory compound according to claim 34, wherein $A^3$ is independently selected from the group consisting of
amino acid side chains and corresponding protected derivatives, cyclohexyl, and alkyl optionally substituted with phenyl, cyclohexyl, carboxy, hydroxylaminocarbonyl, methoxy, benzyloxy, mercapto, N-benzylimidazolyl, biotinyl, tetrazolyl, valinyl-N-carbonyl, or 6-aminohexanoylamino group.

36. A pharmaceutical composition comprising a compound according to claim 22 in an amount effective for prevention, inhibition or suppression of cell adhesion and a pharmaceutically acceptable carrier.

37. The pharmaceutical composition according to claim 36 further comprising an agent selected from the group consisting of corticosteroids, bronchodilators, antiasthmatics, antiinflammatories, antirheumatics, immunosuppressants, antimetabolites, immunomodulators, antipsoriatics and antidiabetics.

38. The cell adhesion inhibitory compound according to claim 18 is compound 359 (L-Proline, 1-[N-[N-[N-[[4-[[(2-methylphenyl)amino]carbonyl]amino]phenyl]acetyl]-L-leucyl]-L-α-aspartyl]-L-valyl]-, disodium salt).

* * * * *

SEQUENCE LISTING

<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 1

Glu Ile Leu Asp Val Pro Ser Thr
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 2

Glu Ile Leu Asp Val
1               5

<210> SEQ ID NO 3

```
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 3

Leu Asp Val Pro Ser
1               5

<210> SEQ ID NO 4
<211> LENGTH: 27
<212> TYPE: PRT
<213> ORGANISM: Artificial Sequence
<220> FEATURE:
<223> OTHER INFORMATION: Synthetically generated peptide

<400> SEQUENCE: 4

Cys Tyr Asp Glu Leu Pro Gln Leu Val Thr Leu Pro His Pro Asn Leu
1               5                   10                  15

His Gly Pro Glu Ile Leu Asp Val Pro Ser Thr
            20                  25

<210> SEQ ID NO 5
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 4
<223> OTHER INFORMATION: Xaa = 4-thioproline

<400> SEQUENCE: 5

Arg Cys Asp Xaa Cys
1               5
```